(12) United States Patent
Schmitz et al.

(10) Patent No.: US 8,729,077 B2
(45) Date of Patent: May 20, 2014

(54) ANTI-VIRAL COMPOUNDS, COMPOSITIONS, AND METHODS OF USE

(75) Inventors: Frank Ulrich Schmitz, Durham, NC (US); Roopa Rai, Durham, NC (US); Christopher Don Roberts, Durham, NC (US); Wieslaw Kazmierski, Durham, NC (US); Richard Grimes, Durham, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 476 days.

(21) Appl. No.: 13/130,118

(22) PCT Filed: Nov. 19, 2009

(86) PCT No.: PCT/US2009/065042
§ 371 (c)(1),
(2), (4) Date: May 19, 2011

(87) PCT Pub. No.: WO2010/062821
PCT Pub. Date: Jun. 3, 2010

(65) Prior Publication Data
US 2011/0224211 A1    Sep. 15, 2011

Related U.S. Application Data

(60) Provisional application No. 61/200,479, filed on Nov. 28, 2008.

(51) Int. Cl.
| | |
|---|---|
| *A61K 31/4178* | (2006.01) |
| *A61K 31/438* | (2006.01) |
| *C07D 403/14* | (2006.01) |
| *C07D 413/14* | (2006.01) |
| *C07D 417/14* | (2006.01) |
| *C07D 498/10* | (2006.01) |

(52) U.S. Cl.
USPC ............ 514/235.8; 514/252.11; 514/278; 514/341; 514/374; 514/397; 544/121; 544/133; 544/137; 544/357; 544/369; 546/19; 546/209; 548/201; 548/216; 548/313.1

(58) Field of Classification Search
None
See application file for complete search history.

(56) References Cited

U.S. PATENT DOCUMENTS

| | | | |
|---|---|---|---|
| 7,659,270 B2 * | 2/2010 | Bachand et al. | ........... 514/235.8 |
| 2008/0044379 A1 | 2/2008 | Bachand et al. | |
| 2008/0044380 A1 | 2/2008 | Bachand et al. | |

* cited by examiner

*Primary Examiner* — Kamal Saeed
(74) *Attorney, Agent, or Firm* — Robert H. Brink

(57) ABSTRACT

Disclosed are compounds, stereoisomers, tautomers, or pharmaceutically acceptable salts thereof, their preparation, use, and compositions thereof for treating an infection mediated at least in part by a virus in the Flaviviridae family of viruses.

4 Claims, No Drawings

ANTI-VIRAL COMPOUNDS, COMPOSITIONS, AND METHODS OF USE

CROSS-REFERENCE TO RELATED APPLICATIONS

This application is filed pursuant to 35 USC 371 as a United States National Phase Application of International Patent Application Serial No. PCT/US2010/065042 filed on Nov. 19, 2009, which claims priority from 61/200,479 filed on Nov. 28, 2008 in the United States.

BACKGROUND OF THE INVENTION

Field of the Invention

The invention relates to the field of pharmaceutical chemistry, in particular to compounds, their preparation, compositions, and uses thereof for treating viral infections in patients mediated, at least in part, by a virus in the Flaviviridae family of viruses.

REFERENCES

The following publications are cited in this application as superscript numbers:
1. Szabo, et al., *Pathol. Oncol. Res.* 2003, 9:215-221.
2. Hoofnagle J H, *Hepatology* 1997, 26:15S-20S.
3. Thomson B J and Finch R G, *Clin Microbial Infect.* 2005, 11:86-94.
4. Moriishi K and Matsuura Y, *Antivir. Chem. Chemother.* 2003, 14:285-297.
5. Fried, et al. *N. Engl. J Med* 2002, 347:975-982.
6. Ni, Z. J. and Wagman, A. S. *Curr. Opin. Drug Discov. Devel.* 2004, 7, 446-459.
7. Beaulieu, P. L. and Tsantrizos, Y. S. *Curr. Opin. Investig. Drugs* 2004, 5, 838-850.
8. Griffith, et al., *Ann. Rep. Med. Chem* 39, 223-237, 2004.
9. Watashi, et al, Molecular Cell, 19, 111-122, 2005
10. Horsmans, et al, Hepatology, 42, 724-731, 2005

All of the above publications are herein incorporated by reference in their entirety to the same extent as if each individual publication was specifically and individually indicated to be incorporated by reference in its entirety.

STATE OF THE ART

Chronic infection with HCV is a major health problem associated with liver cirrhosis, hepatocellular carcinoma and liver failure. An estimated 170 million chronic carriers worldwide are at risk of developing liver disease.[1,2] In the United States alone 2.7 million are chronically infected with HCV, and the number of HCV-related deaths in 2000 was estimated between 8,000 and 10,000, a number that is expected to increase significantly over the next years. Infection by HCV is insidious in a high proportion of chronically infected (and infectious) carriers who may not experience clinical symptoms for many years. Liver cirrhosis can ultimately lead to liver failure. Liver failure resulting from chronic HCV infection is now recognized as a leading cause of liver transplantation.

HCV is a member of the Flaviviridae family of RNA viruses that affect animals and humans. The genome is a single ~9.6-kilobase strand of RNA, and consists of one open reading frame that encodes for a polyprotein of ~3000 amino acids flanked by untranslated regions at both 5' and 3' ends (5'- and 3'-UTR). The polyprotein serves as the precursor to at least 10 separate viral proteins critical for replication and assembly of progeny viral particles. The organization of structural and non-structural proteins in the HCV polyprotein is as follows: C-E1-E2-p7-NS2-NS3-NS4a-NS4b-NS5a-NS5b. Because the replicative cycle of HCV does not involve any DNA intermediate and the virus is not integrated into the host genome, HCV infection can theoretically be cured. While the pathology of HCV infection affects mainly the liver, the virus is found in other cell types in the body including peripheral blood lymphocytes.[3,4]

At present, the standard treatment for chronic HCV is interferon alpha (IFN-alpha) in combination with ribavirin and this requires at least six (6) months of treatment. IFN-alpha belongs to a family of naturally occurring small proteins with characteristic biological effects such as antiviral, immunoregulatory and antitumoral activities that are produced and secreted by most animal nucleated cells in response to several diseases, in particular viral infections. IFN-alpha is an important regulator of growth and differentiation affecting cellular communication and immunological control. Treatment of HCV with interferon has frequently been associated with adverse side effects such as fatigue, fever, chills, headache, myalgias, arthralgias, mild alopecia, psychiatric effects and associated disorders, autoimmune phenomena and associated disorders and thyroid dysfunction. Ribavirin, an inhibitor of inosine 5'-monophosphate dehydrogenase (IMPDH), enhances the efficacy of IFN-alpha in the treatment of HCV. Despite the introduction of ribavirin, more than 50% of the patients do not eliminate the virus with the current standard therapy of interferon-alpha (IFN) and ribavirin. By now, standard therapy of chronic hepatitis C has been changed to the combination of pegylated IFN-alpha plus ribavirin. However, a number of patients still have significant side effects, primarily related to ribavirin. Ribavirin causes significant hemolysis in 10-20% of patients treated at currently recommended doses, and the drug is both teratogenic and embryotoxic. Even with recent improvements, a substantial fraction of patients do not respond with a sustained reduction in viral load[5] and there is a clear need for more effective antiviral therapy of HCV infection.

A number of approaches are being pursuit to combat the virus. They include, for example, application of antisense oligonucleotides or ribozymes for inhibiting HCV replication. Furthermore, low-molecular weight compounds that directly inhibit HCV proteins and interfere with viral replication are considered as attractive strategies to control HCV infection. Among the viral targets, the NS3/4A protease/helicase and the NS5b RNA-dependent RNA polymerase are considered the most promising viral targets for new drugs.[6-8]

Besides targeting viral genes and their transcription and translation products, antiviral activity can also be achieved by targeting host cell proteins that are necessary for viral replication. For example, Watashi et al.[9] show how antiviral activity can be achieved by inhibiting host cell cyclophilins. Alternatively, a potent TLR7 agonist has been shown to reduce HCV plasma levels in humans.[10]

However, none of the compounds described above have progressed beyond clinical trials.[6,8]

Notwithstanding the above, the discovery of new compounds active against one or more members of the Flaviviridae family of viruses would be beneficial particularly in view of the difficulty currently faced in treating diseases mediated, at least in part, by one or more of such viruses.

SUMMARY OF THE INVENTION

This invention is directed to compounds, their preparation, compositions, and uses thereof for treating viral infections mediated, at least in part, by a virus in the Flaviviridae family of viruses. In one embodiment, provided is compound of Formula (I)

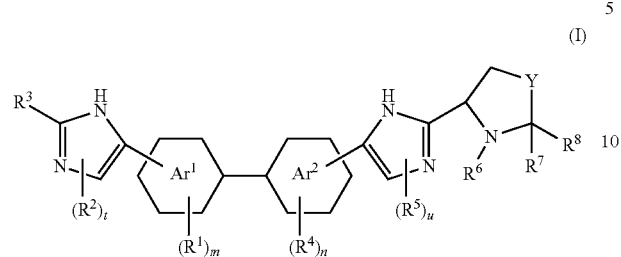

or a pharmaceutically acceptable salt thereof, wherein:
Ar$^1$ and Ar$^2$ are independently phenyl or a 6-member aromatic ring of 1 to 3 ring nitrogen atoms;
Y is X or XCR$^9$R$^9$;
X is selected from a bond, O, S, S(O), SO$_2$, and CR$^9$R$^9$;
each of R$^1$ and R$^4$ are independently selected from the group consisting of halo, alkyl, substituted alkyl, hydroxy, alkoxy, substituted alkoxy, acyl, COOH, carboxy ester, amino, substituted amino, acylamino, and amino carbonyl;
each of R$^2$ and R$^5$ are attached to a carbon or nitrogen ring atom and are independently selected from the group consisting of alkyl, substituted alkyl, carboxy ester, COOH, and amino carbonyl;
R$^3$ is selected from the group consisting of cycloalkyl, substituted cycloalkyl, heterocyclic, substituted heterocyclic, and

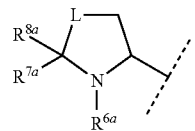

wherein L is X$^a$ or X$^a$CR$^{9a}$R$^{9a}$; X$^a$ is selected from a bond, O, S, S(O), SO$_2$, and CR$^{9a}$R$^{9a}$; an R$^{7a}$ and R$^{8a}$ are independently selected from the group consisting of hydrogen, halo, alkyl, substituted alkyl, hydroxy, alkoxy, substituted alkoxy, amino, substituted amino and COOH, or R$^{7a}$ and R$^{8a}$ together with the carbon atom to which they are attached form a cycloalkyl, substituted cycloalkyl, heterocyclic, or substituted heterocyclic ring;
R$^6$ and R$^{6a}$ are independently -D-W where D is C(O), C(S), or SO$_2$ and W is independently R$^{10}$, CHR$^{12}$NR$^{10}$R$^{11}$, OR$^{10}$, OCH$_2$R$^{10}$, or NR$^{10}$R$^{11}$;
R$^7$ and R$^8$ together with the carbon atom to which they are attached form a cycloalkyl, substituted cycloalkyl, heterocyclic, or substituted heterocyclic ring, or one of R$^7$ and R$^8$ is hydrogen or alkyl and the other of R$^7$ and R$^8$ is cycloalkyl, substituted cycloalkyl, heterocyclic, substituted heterocyclic, or alkyl substituted with amino, substituted amino, aminocarbonylamino, carboxy, carboxy ester, aminocarbonyl, acylamino, heterocyclic, or substituted heterocyclic;
each of R$^9$ and R$^{9a}$ are independently selected from the group consisting of hydrogen, halo, alkyl, substituted alkyl, hydroxy, alkoxy, substituted alkoxy, amino, substituted amino and COOH;
R$^{10}$ is independently selected from the group consisting of alkyl, substituted alkyl, acyl, carboxy ester, cycloalkyl, substituted cycloalkyl, heterocyclic, substituted heterocyclic, aryl, substituted aryl, heteroaryl, and substituted heteroaryl;
R$^{11}$ is independently selected from the group consisting of hydrogen, alkyl, and substituted alkyl;
R$^{12}$ is selected from the group consisting of hydrogen, alkyl, substituted alkyl, phenyl, and substituted phenyl;
m and n are independently 0, 1, 2, 3, or 4; and
t and u are independently 0, 1, or 2.
In one embodiment, provided is compound of Formula (II)

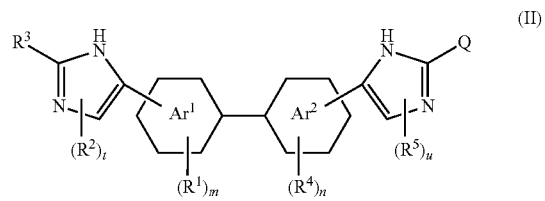

or a pharmaceutically acceptable salt thereof, wherein:
Ar$^1$ and Ar$^2$ are independently phenyl or 6-member aromatic ring of 1 to 3 ring nitrogen atoms;
each of R$^1$ and R$^4$ are independently selected from the group consisting of halo, alkyl, substituted alkyl, hydroxy, alkoxy, substituted alkoxy, acyl, COOH, carboxy ester, amino, substituted amino, acylamino, and amino carbonyl;
each of R$^2$ and R$^5$ are independently selected from the group consisting of alkyl, substituted alkyl, carboxy ester, COOH, and amino carbonyl;
R$^3$ is selected from the group consisting of cycloalkyl, substituted cycloalkyl, heterocyclic, substituted heterocyclic, and

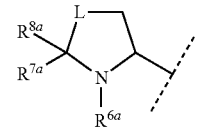

wherein L is X$^a$ or X$^a$CR$^{9a}$R$^{9a}$; X$^a$ is selected from a bond, O, S, S(O), SO$_2$, and CR$^{9a}$R$^{9a}$; and R$^{7a}$ and R$^{8a}$ are independently selected from the group consisting of hydrogen, halo, alkyl, substituted alkyl, hydroxy, alkoxy, substituted alkoxy, amino, substituted amino and COOH, or R$^{7a}$ and R$^{8a}$ together with the carbon atom to which they are attached form a cycloalkyl, substituted cycloalkyl, heterocyclic, or substituted heterocyclic ring;
Q is selected from the group consisting of cycloalkyl, substituted cycloalkyl, and

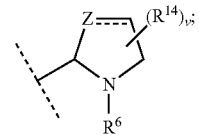

Z is selected from the group consisting of a bond, O, S, CH$_2$NR$^{13}$, CH, and CR$^{14}$;
when Z is a bond, O, S, or NR$^{13}$, then === represents a single bond;
when Z is CH or CR$^{14}$, then === represents a double bond;

$R^6$ and $R^{6a}$ are independently -D-W where D is C(O), C(S), or $SO_2$ and W is independently $R^{10}$, $CHR^{12}NR^{10}R^{11}$, $OR^{10}$, $OCH_2R^{10}$, or $NR^{10}R^{11}$;

$R^{9a}$ is independently selected from the group consisting of hydrogen, halo, alkyl, substituted alkyl, hydroxy, alkoxy, substituted alkoxy, amino, substituted amino and COOH;

$R^{10}$ is independently selected from the group consisting of alkyl, substituted alkyl, acyl, cycloalkyl, substituted cycloalkyl, heterocyclic, substituted heterocyclic, aryl, substituted aryl, heteroaryl, and substituted heteroaryl;

$R^{11}$ is independently selected from the group consisting of hydrogen, alkyl, and substituted alkyl;

$R^{12}$ is selected from the group consisting of hydrogen, alkyl, substituted alkyl, phenyl, and substituted phenyl;

$R^{13}$ is selected from the group consisting of hydrogen, alkyl, substituted alkyl, acyl, and substituted sulfonyl;

$R^{14}$ is independently selected from the group consisting of halo, alkyl, substituted alkyl, hydroxy, alkoxy, substituted alkoxy, amino, substituted amino, cycloalkyl, substituted cycloalkyl, aryl, substituted aryl, heteroaryl, substituted heteroaryl, heterocyclyl, and substituted heterocyclyl, or two $R^{14}$ together with the carbon atom to which they are attached form a cycloalkyl, substituted cycloalkyl, heterocyclic, or substituted heterocyclic ring;

m and n are independently 0, 1, 2, 3, or 4;

t and u are independently 0, 1, or 2; and v is 0, 1, 2, 3, or 4.

In other embodiments provided are pharmaceutical compositions comprising a pharmaceutically acceptable carrier and a therapeutically effective amount of a compound of Formula (I) or Formula (II) or a pharmaceutically acceptable salt thereof.

In other embodiments provided are uses of a compound of Formula (I) or Formula (II) or a pharmaceutically acceptable salt thereof for treating a viral infection mediated at least in part by a virus in the Flaviviridae family of viruses. In some aspects, the viral infection is mediated by hepatitis C virus.

DETAILED DESCRIPTION

Definitions

As used herein, the following definitions shall apply unless otherwise indicated.

"Alkyl" refers to monovalent saturated aliphatic hydrocarbyl groups having from 1 to 10 carbon atoms and, in some embodiments, from 1 to 6 carbon atoms. "$C_{x-y}$alkyl" refers to alkyl groups having from x to y carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3$)($CH_3CH_2$)CH—), t-butyl (($CH_3)_3C$—), n-pentyl ($CH_3CH_2CH_2CH_2CH_2$—), and neopentyl (($CH_3)_3CCH_2$—).

"Substituted alkyl" refers to an alkyl group having from 1 to 5 and, in some embodiments, 1 to 3 or 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, spirocycloalkyl, $SO_3H$, substituted sulfonyl, sulfonyloxy, thioacyl, thiocyanate, thiol, alkylthio, and substituted alkylthio, wherein said substituents are as defined herein.

"Alkylidene" or "alkylene" refers to divalent saturated aliphatic hydrocarbyl groups having from 1 to 10 carbon atoms and, in some embodiments, from 1 to 6 carbon atoms. "$(C_{x-y})$alkylene" refers to alkylene groups having from x to y carbon atoms. The alkylidene and alkylene groups include branched and straight chain hydrocarbyl groups. For example "$(C_{1-6})$alkylene" is meant to include methylene, ethylene, propylene, 2-methylpropylene, pentylene, and the like.

"Substituted alkylidene" or "substituted alkylene" refers to an alkylidene group having from 1 to 5 and, in some embodiments, 1 to 3 or 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, oxo, thione, spirocycloalkyl, $SO_3H$, substituted sulfonyl, sulfonyloxy, thioacyl, thiocyanate, thiol, alkylthio, and substituted alkylthio, wherein said substituents are as defined herein.

"Alkenyl" refers to a linear or branched hydrocarbyl group having from 2 to 10 carbon atoms and in some embodiments from 2 to 6 carbon atoms or 2 to 4 carbon atoms and having at least 1 site of vinyl unsaturation (>C=C<). For example, ($C_x$-$C_y$)alkenyl refers to alkenyl groups having from x to y carbon atoms and is meant to include for example, ethenyl, propenyl, 1,3-butadienyl, and the like.

"Substituted alkenyl" refers to alkenyl groups having from 1 to 3 substituents and, in some embodiments, 1 to 2 substituents selected from the group consisting of alkoxy, substituted alkoxy, acyl, acylamino, acyloxy, alkyl, substituted alkyl, alkynyl, substituted alkynyl, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy or thiol substitution is not attached to a vinyl (unsaturated) carbon atom.

"Alkynyl" refers to a linear monovalent hydrocarbon radical or a branched monovalent hydrocarbon radical containing at least one triple bond. The term "alkynyl" is also meant to include those hydrocarbyl groups having one triple bond and one double bond. For example, $(C_2-C_6)$alkynyl is meant to include ethynyl, propynyl, and the like.

"Substituted alkynyl" refers to alkynyl groups having from 1 to 3 substituents and, in some embodiments, from 1 to 2 substituents selected from the group consisting of alkoxy, substituted alkoxy, acyl, acylamino, acyloxy, alkyl, substituted alkyl, alkenyl, substituted alkenyl, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are as defined herein and with the proviso that any hydroxy or thiol substitution is not attached to an acetylenic carbon atom.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is as defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, substituted hydrazino-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, substituted hydrazino, heteroaryl, substituted heteroaryl, heterocyclic, and substituted heterocyclic are as defined herein. Acyl includes the "acetyl" group $CH_3C(O)$—.

"Acylamino" refers to the groups —NR$^{20}$C(O)alkyl, —NR$^{20}$C(O)substituted alkyl, —NR$^{20}$C(O)cycloalkyl, —NR$^{20}$C(O)substituted cycloalkyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic wherein R$^{20}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Amino" refers to the group —NH$_2$.

"Substituted amino" refers to the group —NR$^{21}$R$^{22}$ where R$^{21}$ and R$^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cylcoalkyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic and wherein R$^{21}$ and R$^{22}$ are optionally joined together with the nitrogen bound thereto to form a heterocyclic or substituted heterocyclic group, provided that R$^{21}$ and R$^{22}$ are both not hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein. When R$^{21}$ is hydrogen and R$^{22}$ is alkyl, the substituted amino group is sometimes referred to herein as alkylamino. When R$^{21}$ and R$^{22}$ are alkyl, the substituted amino group is sometimes referred to herein as dialkylamino. When referring to a monosubstituted amino, it is meant that either R$^{21}$ or R$^{22}$ is hydrogen but not both. When referring to a disubstituted amino, it is meant that neither R$^{21}$ nor R$^{22}$ are hydrogen.

"Hydroxyamino" refers to the group —NHOH.

"Alkoxyamino" refers to the group —NHO-alkyl wherein alkyl is defined herein.

"Aminocarbonyl" refers to the group —C(O)NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic, and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Aminothiocarbonyl" refers to the group —C(S)NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Aminocarbonylamino" refers to the group —NR$^{20}$C(O)NR$^{23}$R$^{24}$ where R$^{20}$ is hydrogen or alkyl and R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Aminothiocarbonylamino" refers to the group —$NR^{20}C(S)NR^{23}R^{24}$ where $R^{20}$ is hydrogen or alkyl and $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Aminocarbonyloxy" refers to the group —O—C(O)$NR^{23}R^{24}$ where $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Aminosulfonyl" refers to the group —$SO_2NR^{23}R^{24}$ where $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Aminosulfonyloxy" refers to the group —O—$SO_2NR^{23}R^{24}$ where $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Aminosulfonylamino" refers to the group —$NR^{20}$—$SO_2NR^{23}R^{24}$ where $R^{20}$ is hydrogen or alkyl and $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Amidino" refers to the group —$C(=NR^{25})NR^{23}R^{24}$ where $R^{25}$, $R^{23}$, and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Aryl" refers to an aromatic group of from 6 to 14 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "aryl" applies when the point of attachment is at an aromatic carbon atom (e.g., 5,6,7,8 tetrahydronaphthalene-2-yl is an aryl group as its point of attachment is at the 2-position of the aromatic phenyl ring).

"Substituted aryl" refers to aryl groups which are substituted with 1 to 8 and, in some embodiments, 1 to 5, 1 to 3, or 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiocyanate, thiol, alkylthio, and substituted alkylthio, wherein said substituents are defined herein.

"Aryloxy" refers to the group —O-aryl, where aryl is as defined herein, that includes, by way of example, phenoxy and naphthyloxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Azido" refers to the group —$N_3$.

"Hydrazino" refers to the group —$NHNH_2$.

"Substituted hydrazino" refers to the group —NR$^{26}$NR$^{27}$R$^{28}$ where R$^{26}$, R$^{27}$, and R$^{28}$ are independently selected from the group consisting of hydrogen, alkyl, substituted alkyl, alkenyl, substituted alkenyl, alkynyl, substituted alkynyl, aryl, substituted aryl, carboxyl ester, cycloalkyl, substituted cycloalkyl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cylcoalkyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic and wherein R$^{27}$ and R$^{28}$ are optionally joined, together with the nitrogen bound thereto to form a heterocyclic or substituted heterocyclic group, provided that R$^{27}$ and R$^{28}$ are both not hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Cyano" or "carbonitrile" refers to the group —CN.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)amino" refers to the group —NR$^{20}$—C(O)O-alkyl, —NR$^{20}$—C(O)O-substituted alkyl, —NR$^{20}$—C(O)O-alkenyl, —NR$^{20}$—C(O)O-substituted alkenyl, —NR$^{20}$—C(O)O-alkynyl, —NR$^{20}$—C(O)O-substituted alkynyl, —NR$^{20}$—C(O)O-aryl, —NR$^{20}$—C(O)O-substituted aryl, —NR$^{20}$—C(O)O-cycloalkyl, —NR$^{20}$—C(O)O-substituted cycloalkyl, —NR$^{20}$—C(O)O-heteroaryl, —NR$^{20}$—C(O)O-substituted heteroaryl, —NR$^{20}$—C(O)O-heterocyclic, and —NR$^{20}$—C(O)O-substituted heterocyclic wherein R$^{20}$ is alkyl or hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Cycloalkyl" refers to a saturated or partially saturated cyclic group of from 3 to 14 carbon atoms and no ring heteroatoms and having a single ring or multiple rings including fused, bridged, and spiro ring systems. For multiple ring systems having aromatic and non-aromatic rings that have no ring heteroatoms, the term "cycloalkyl" applies when the point of attachment is at a non-aromatic carbon atom (e.g. 5,6,7,8,-tetrahydronaphthalene-5-yl). The term "Cycloalkyl" includes cycloalkenyl groups. Examples of cycloalkyl groups include, for instance, adamantyl, cyclopropyl, cyclobutyl, cyclopentyl, cyclooctyl, and cyclohexenyl. "$C_{x-y}$cycloalkyl" refers to cycloalkyl groups having x to y carbon atoms.

"Cycloalkenyl" refers to a partially saturated cycloalkyl ring having at least one site of >C=C< ring unsaturation.

"Cycloalkylene" refer to divalent cycloalkyl groups as defined herein. Examples of cycloalkyl groups include those having three to six carbon ring atoms such as cyclopropylene, cyclobutylene, cyclopentylene, and cyclohexylene.

"Substituted cycloalkyl" refers to a cycloalkyl group, as defined herein, having from 1 to 8, or 1 to 5, or in some embodiments 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiocyanate, thiol, alkylthio, and substituted alkylthio, wherein said substituents are as defined herein. The term "substituted cycloalkyl" includes substituted cycloalkenyl groups.

"Cycloalkyloxy" refers to —O-cycloalkyl wherein cycloalkyl is as defined herein.

"Substituted cycloalkyloxy" refers to —O-(substituted cycloalkyl) wherein substituted cycloalkyl is as defined herein.

"Cycloalkylthio" refers to —S-cycloalkyl wherein cycloalkyl is as defined herein.

"Substituted cycloalkylthio" refers to —S-(substituted cycloalkyl).

"Guanidino" refers to the group —NHC(=NH)NH$_2$.

"Substituted guanidino" refers to —NR$^{29}$C(=NR$^{29}$)N(R$^{29}$)$_2$ where each R$^{29}$ is independently selected from the group consisting of hydrogen, alkyl, substituted alkyl, aryl, substituted aryl, heteroaryl, substituted heteroaryl, heterocyclyl, and substituted heterocyclyl and two R$^{29}$ groups attached to a common guanidino nitrogen atom are optionally joined together with the nitrogen bound thereto to form a heterocyclic or substituted heterocyclic group, provided that at least one R$^{29}$ is not hydrogen, and wherein said substituents are as defined herein.

"Halo" or "halogen" refers to fluoro, chloro, bromo, and iodo.

"Haloalkyl" refers to substitution of alkyl groups with 1 to 5 or in some embodiments 1 to 3 halo groups.

"Haloalkoxy" refers to substitution of alkoxy groups with 1 to 5 or in some embodiments 1 to 3 halo groups.

"Hydroxy" or "hydroxyl" refers to the group —OH.

"Heteroaryl" refers to an aromatic group of from 1 to 14 carbon atoms and 1 to 6 heteroatoms selected from the group consisting of oxygen, nitrogen, and sulfur and includes single ring (e.g. imidazolyl) and multiple ring systems (e.g. benzimidazol-2-yl and benzimidazol-6-yl). For multiple ring systems, including fused, bridged, and spiro ring systems having aromatic and non-aromatic rings, the term "heteroaryl" applies if there is at least one ring heteroatom and the point of attachment is at an atom of an aromatic ring (e.g. 1,2,3,4-tetrahydroquinolin-6-yl and 5,6,7,8-tetrahydroquinolin-3-yl). In one embodiment, the nitrogen and/or the sulfur ring atom(s) of the heteroaryl group are optionally oxidized to provide for the N-oxide (N→O), sulfinyl, or sulfonyl moieties. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyridazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, quinazolinonyl, benzimidazolyl, benzisoxazolyl, or benzothienyl.

"Substituted heteroaryl" refers to heteroaryl groups that are substituted with from 1 to 8 or in some embodiments 1 to 5, or 1 to 3, or 1 to 2 substituents selected from the group consisting of the substituents defined for substituted aryl.

"Heteroaryloxy" refers to —O-heteroaryl wherein heteroaryl is as defined herein.

"Substituted heteroaryloxy refers to the group —O-(substituted heteroaryl) wherein substituted heteroaryl is as defined herein.

"Heteroarylthio" refers to the group —S-heteroaryl wherein heteroaryl is as defined herein.

"Substituted heteroarylthio" refers to the group —S-(substituted heteroaryl) wherein substituted heteroaryl is as defined herein.

"Heterocyclic" or "heterocycle" or "heterocycloalkyl" or "heterocyclyl" refers to a saturated or partially saturated cyclic group having from 1 to 14 carbon atoms and from 1 to 6 heteroatoms selected from the group consisting of nitrogen, sulfur, or oxygen and includes single ring and multiple ring systems including fused, bridged, and spiro ring systems. For multiple ring systems having aromatic and/or non-aromatic rings, the terms "heterocyclic", "heterocycle", "heterocycloalkyl", or "heterocyclyl" apply when there is at least one ring heteroatom and the point of attachment is at an atom of a non-aromatic ring (e.g. 1,2,3,4-tetrahydroquinoline-3-yl, 5,6,7,8-tetrahydroquinoline-6-yl, and decahydroquinolin-6-yl). In one embodiment, the nitrogen and/or sulfur atom(s) of the heterocyclic group are optionally oxidized to provide for the N-oxide, sulfinyl, sulfonyl moieties. More specifically the heterocyclyl includes, but is not limited to, tetrahydropyranyl, piperidinyl, N-methylpiperidin-3-yl, piperazinyl, N-methylpyrrolidin-3-yl, 3-pyrrolidinyl, 2-pyrrolidon-1-yl, morpholinyl, and pyrrolidinyl. A prefix indicating the number of carbon atoms (e.g., $C_3$-$C_{10}$) refers to the total number of carbon atoms in the portion of the heterocyclyl group exclusive of the number of heteroatoms.

"Substituted heterocyclic" or "Substituted heterocycle" or "substituted heterocycloalkyl" or "substituted heterocyclyl" refers to heterocyclic groups, as defined herein, that are substituted with from 1 to 5 or in some embodiments 1 to 3 of the substituents as defined for substituted cycloalkyl.

"Heterocyclyloxy" refers to the group —O-heterocycyl wherein heterocyclyl is as defined herein.

"Substituted heterocyclyloxy" refers to the group —O-(substituted heterocycyl) wherein substituted heterocyclyl is as defined herein.

"Heterocyclylthio" refers to the group —S-heterocycyl wherein heterocyclyl is as defined herein.

"Substituted heterocyclylthio" refers to the group —S-(substituted heterocycyl) wherein substituted heterocyclyl is as defined herein.

Examples of heterocycle and heteroaryl groups include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —$NO_2$.

"Oxo" refers to the atom (=O).

"Oxide" refers to products resulting from the oxidation of one or more heteroatoms. Examples include N-oxides, sulfoxides, and sulfones.

"Spiro ring systems" refers to bicyclic cycloalkyl and/or heterocyclic ring systems that have only a single ring atom common to both rings.

"Spirocycloalkyl" refers to a 3 to 10 member cyclic substituent formed by replacement of two hydrogen atoms at a common carbon atom with an alkylene group having 2 to 9 carbon atoms, as exemplified by the following structure wherein the methylene group shown here attached to bonds marked with wavy lines is substituted with a spirocycloalkyl group:

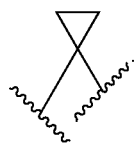

"Sulfonyl" refers to the divalent group —$S(O)_2$—.

"Substituted sulfonyl" refers to the group —$SO_2$-alkyl, —$SO_2$-substituted alkyl, —$SO_2$-alkenyl, —$SO_2$-substituted alkenyl, —$SO_2$-alkynyl, —$SO_2$-substituted alkynyl, —$SO_2$-cycloalkyl, —$SO_2$-substituted cylcoalkyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfonyl includes groups such as methyl-$SO_2$—, phenyl-$SO_2$—, and 4-methylphenyl-$SO_2$—.

"Sulfonyloxy" refers to the group —$OSO_2$-alkyl, —$OSO_2$-substituted alkyl, —$OSO_2$-alkenyl, —$OSO_2$-substituted alkenyl, —$OSO_2$-cycloalkyl, —$OSO_2$-substituted cylcoalkyl, —$OSO_2$-aryl, —$OSO_2$-substituted aryl, —$OSO_2$-heteroaryl, —$OSO_2$-substituted heteroaryl, —$OSO_2$-heterocyclic, —$OSO_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiol" refers to the group —SH.

"Alkylthio" refers to the group —S-alkyl wherein alkyl is as defined herein.

"Substituted alkylthio" refers to the group —S-(substituted alkyl) wherein substituted alkyl is as defined herein.

"Thiocarbonyl" refers to the divalent group —C(S)— which is equivalent to —C(=S)—.

"Thione" refers to the atom (=S).

"Thiocyanate" refers to the group —SCN.

"Compound" and "compounds" as used herein refers to a compound encompassed by the generic formulae disclosed herein, any subgenus of those generic formulae, and any forms of the compounds within the generic and subgeneric formulae, including the stereoisomers, racemates, and tautomers and salts of the compound or compounds.

"Stereoisomer" or "stereoisomers" refer to compounds that differ in the chirality of one or more stereocenters. Stereoisomers include enantiomers and diastereomers.

"Racemates" refers to a mixture of enantiomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

"Patient" refers to mammals and includes humans and non-human mammals.

"Therapeutically effective amount" is an amount sufficient to treat a specified disorder or disease.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to-substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

The follow features relate to compounds of Formula (I).

In some aspects, provided is a compound that is

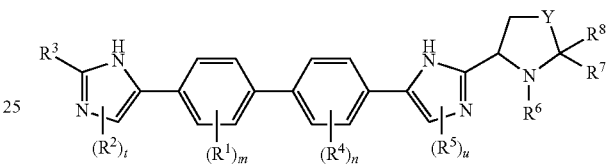

or a pharmaceutically acceptable salt thereof, wherein $R^1$, $R^2$, $R^3$, $R^4$, $R^5$, $R^6$, $R^7$, $R^8$, Y, m, n, t, and u are previously defined for Formula (I).

In some aspects, at least one of $R^1$ or $R^4$ is alkyl or halo. In some such aspects at least one of $R^1$ or $R^4$ is methyl or fluoro.

In some aspects, at least one of $R^2$ or $R^5$ is alkyl or substituted alkyl.

In some aspects, $R^6$ is C(O)W. In some such aspects $R^6$ is $C(O)CHR^{12}NR^{10}R^{11}$. In certain aspects, $R^{10}$ and $R^{11}$ are independently H or methyl.

In some aspects, Y is O or S.

In some aspects, $R^7$ and $R^8$ form a $C_3$-$C_6$ cycloalkyl group or a $C_5$-$C_6$ heterocyclic group having one ring heteroatom selected from O and $NR^a$, wherein $R^a$ is H, alkyl, substituted alkyl, acyl, or substituted sulfonyl.

In some aspects, $R^7$ is hydrogen and $R^8$ is alkyl substituted with amino, substituted amino, aminocarbonylamino, carboxy, carboxy ester, aminocarbonyl, acylamino, heterocyclic, or substituted heterocyclic.

In some aspects, $R^3$ is

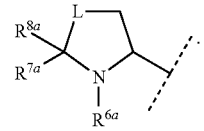

In some aspects, provided is a compound selected from the group consisting of

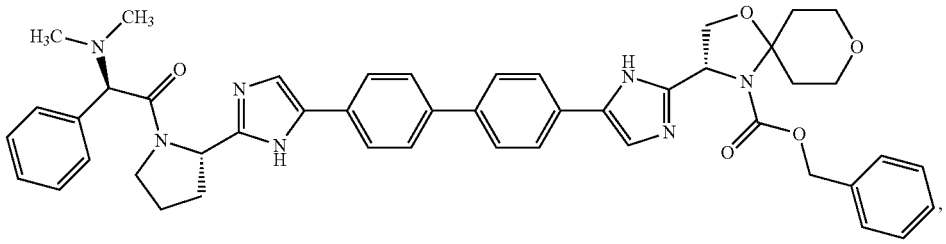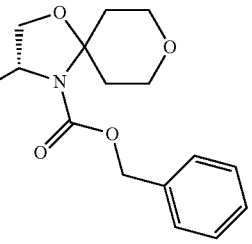

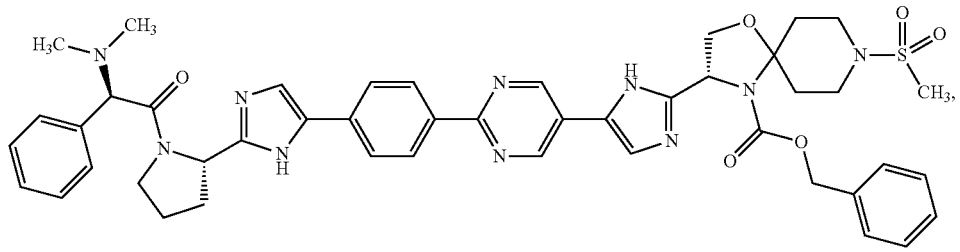
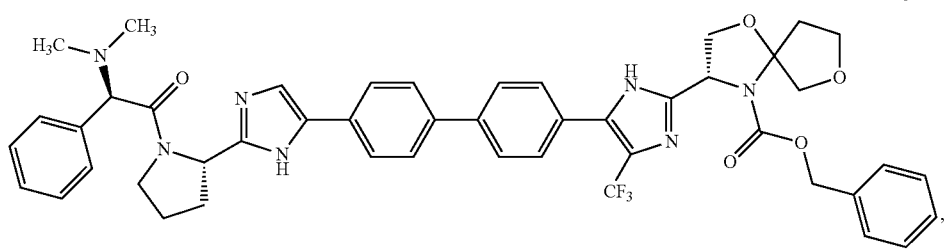
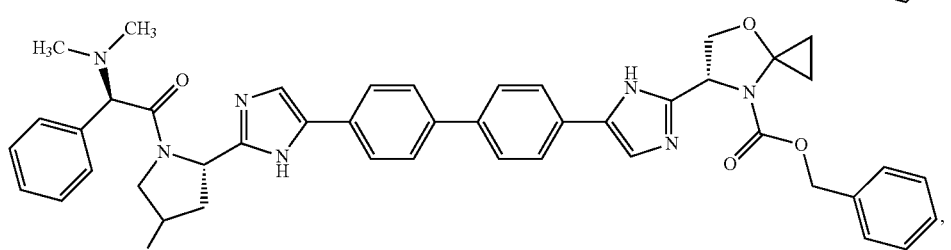
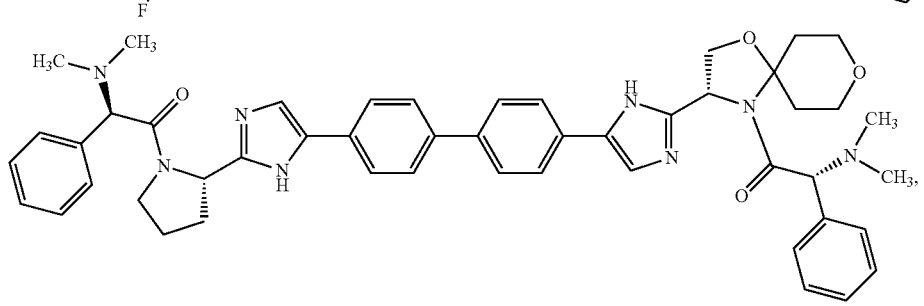
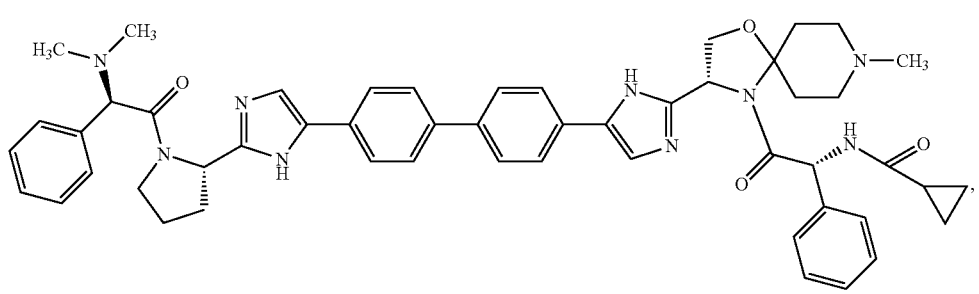
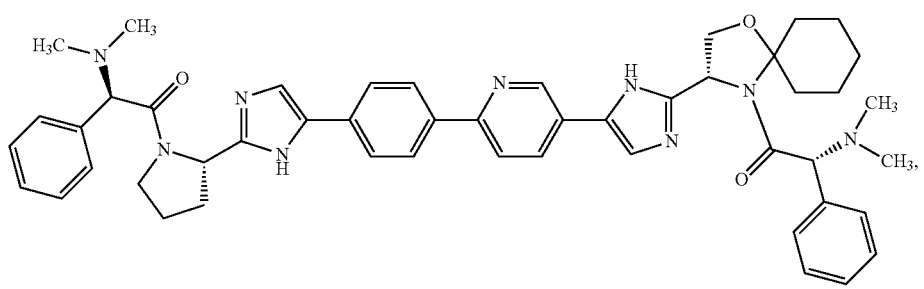

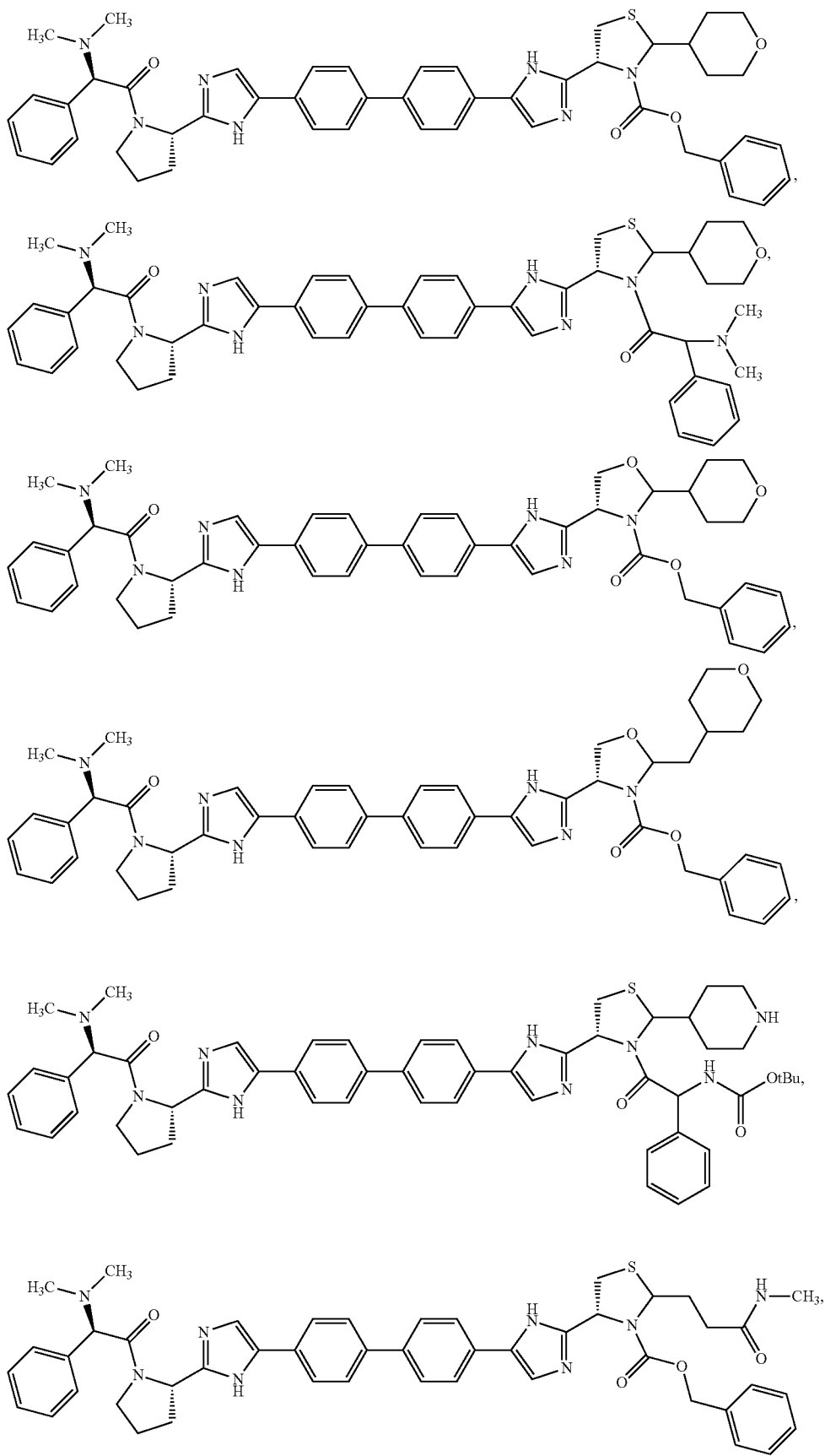

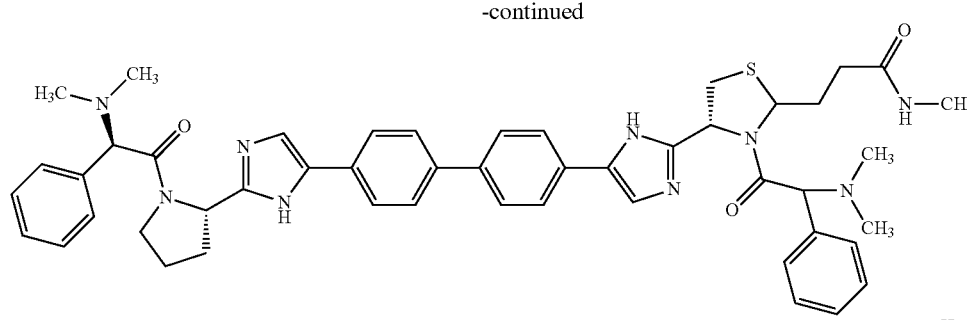

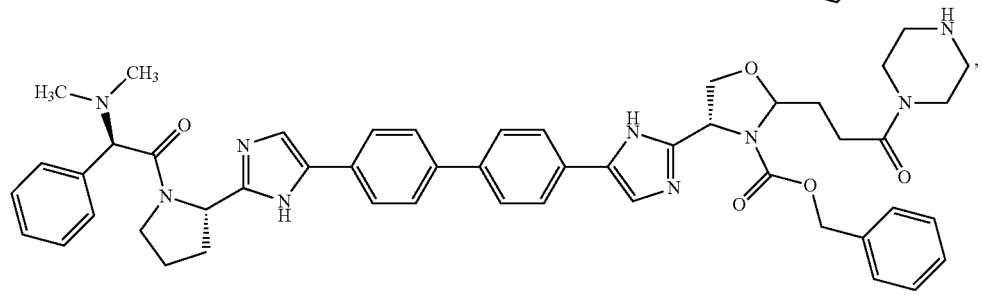

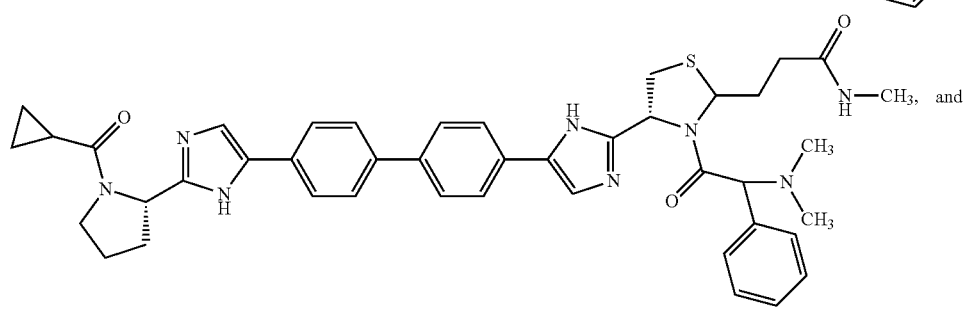

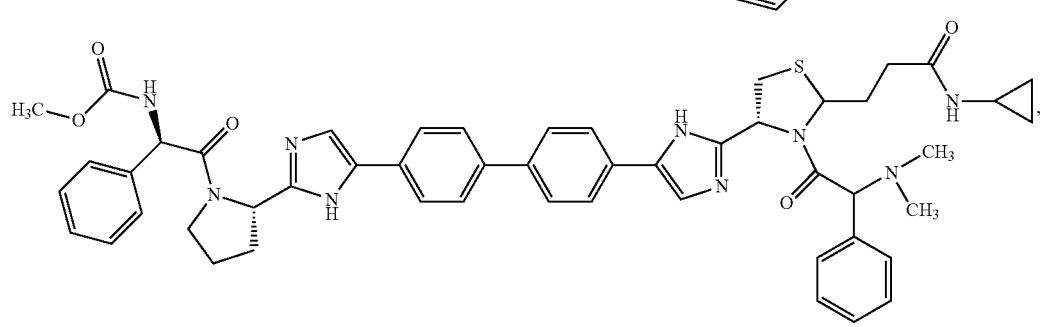

or a pharmaceutically acceptable salt thereof.

The follow features relate to compounds of Formula (II).

In some aspects, provided is a compound that is

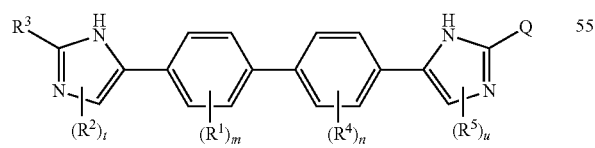

or a pharmaceutically acceptable salt thereof, wherein $R^1$, $R^2$, $R^3$, $R^4$, $R^5$, Q, m, n, t, and u are previously defined for Formula (II).

In some aspects, Q is selected from the group consisting of:

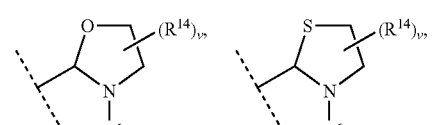

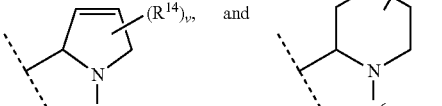

wherein $R^{15}$ is selected from the group consisting of hydrogen, alkyl, substituted alkyl, acyl, and substituted sulfonyl.

In some aspects provided is a compound selected from the group consisting of selected from O and $NR^{16}$ wherein $R^{16}$ is H, alkyl, substituted alkyl, acyl, or substituted sulfonyl.

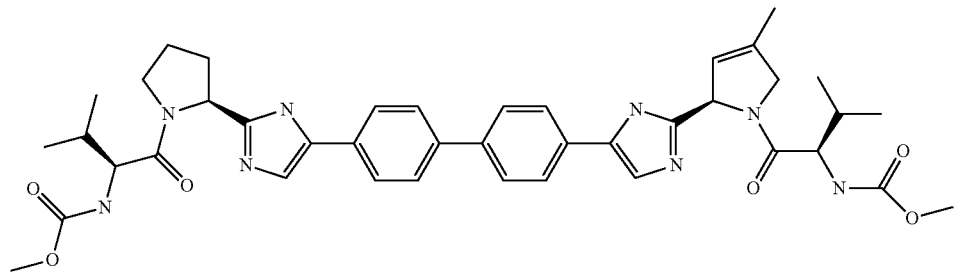

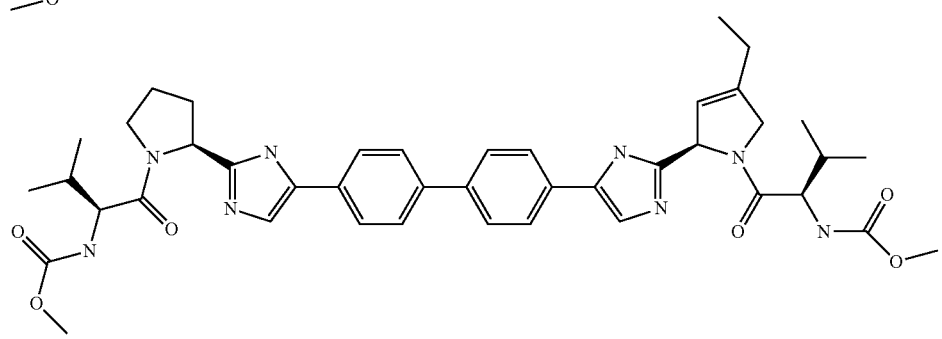

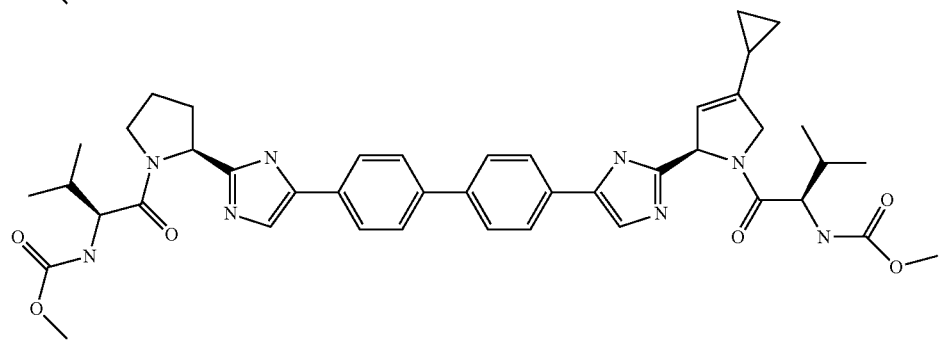

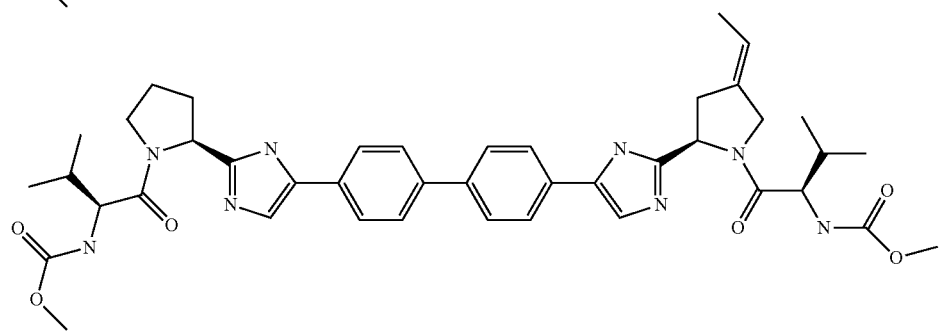

In some aspects, Q is selected from group consisting of cyclopropyl, cyclobutyl, cyclopentyl, cyclopentenyl, cyclohexyl, and cyclohexenyl, wherein each of the aforementioned groups are substituted with $(R^{14})_y$.

In some aspects, at least one of $R^1$ or $R^4$ is alkyl or halo. In some such aspects at least one of $R^1$ or $R^4$ is methyl or fluoro.

In some aspects, at least one of $R^2$ or $R^5$ is alkyl or substituted alkyl.

In some aspects, $R^6$ is C(O)W. In some such aspects $R^6$ is $C(O)CHR^{12}NR^{10}R^{11}$. In certain aspects, $R^{10}$ and $R^{11}$ are independently H or methyl.

In some aspects, two of $R^{14}$ together with a carbon atom to which both are attached form a $C_3$-$C_6$ cycloalkyl group or a $C_5$-$C_6$ heterocyclic group having one ring heteroatom In some aspects, one of $R^{14}$ is alkyl substituted with carboxy, carboxy ester, aminocarbonyl, acylamino, heterocyclic, or substituted heterocyclic.

In some aspects, $R^3$ is

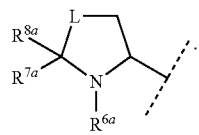

In some aspects, provided is a compound selected from the group consisting of
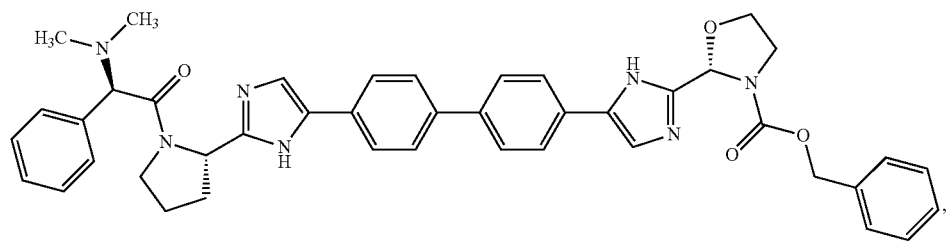
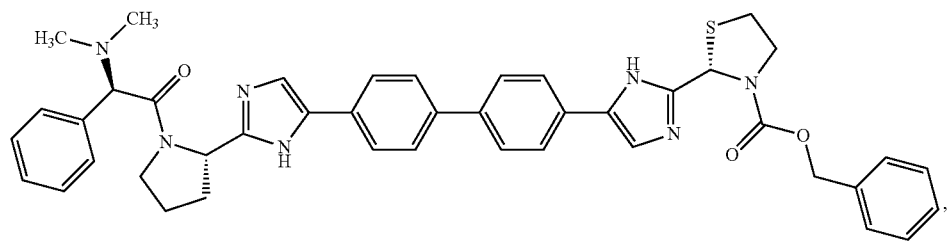
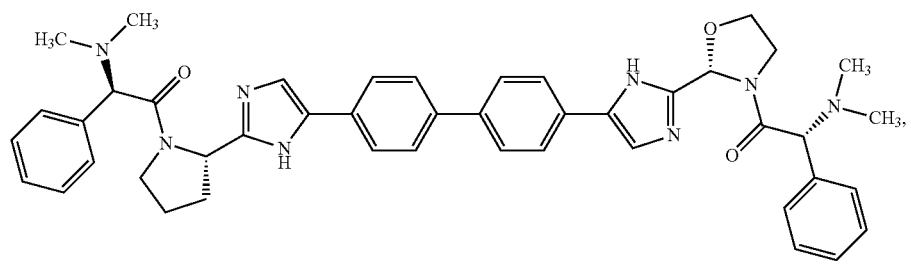
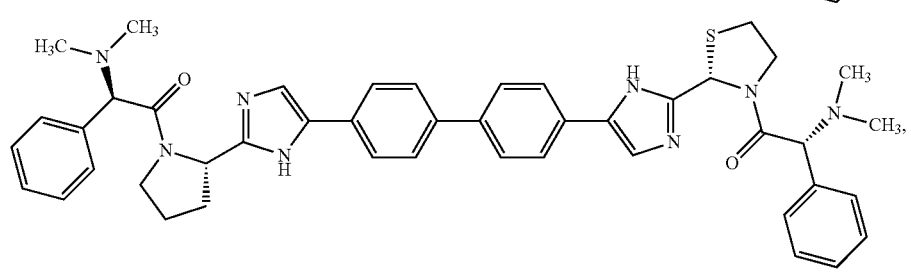
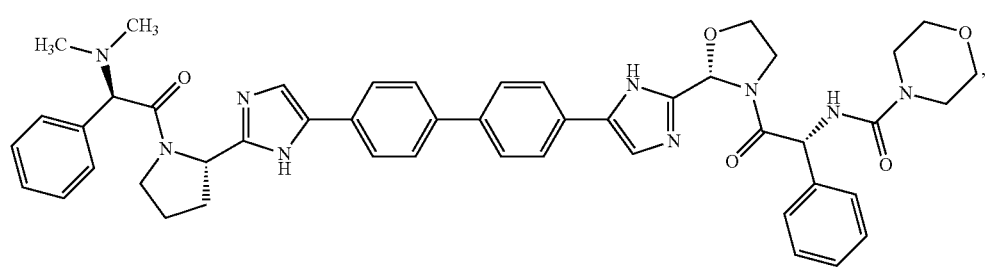
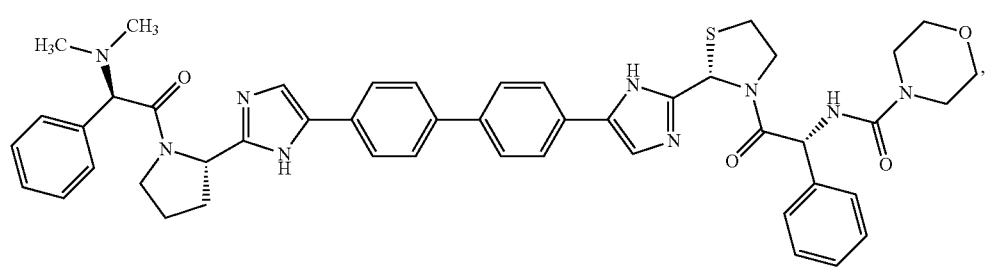

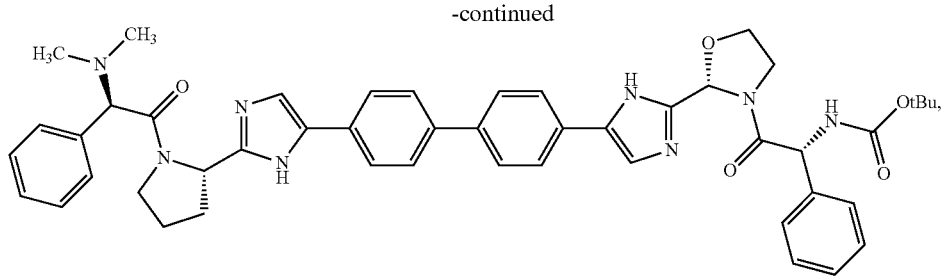
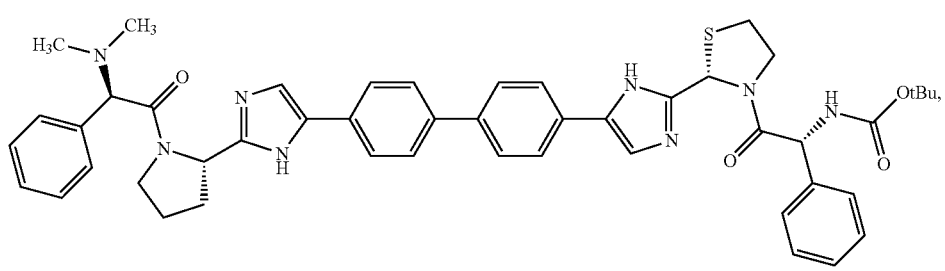
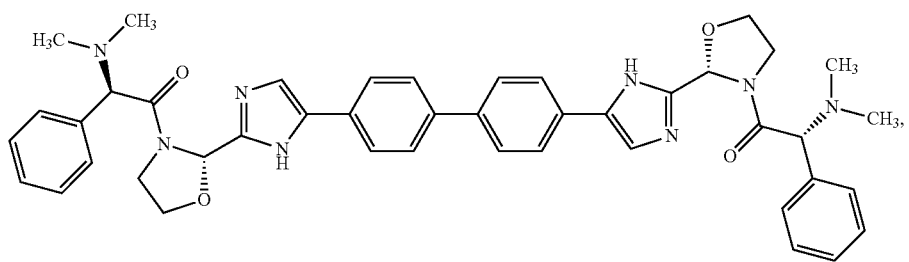
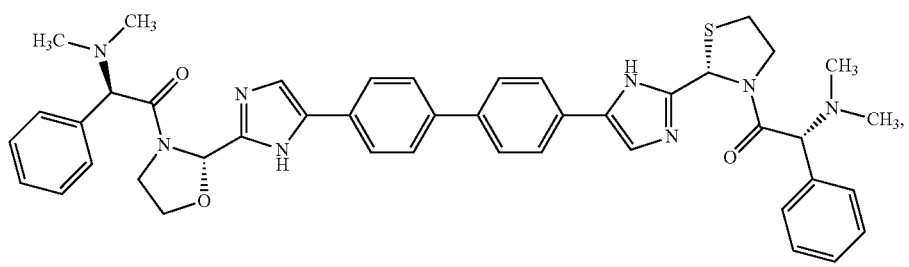
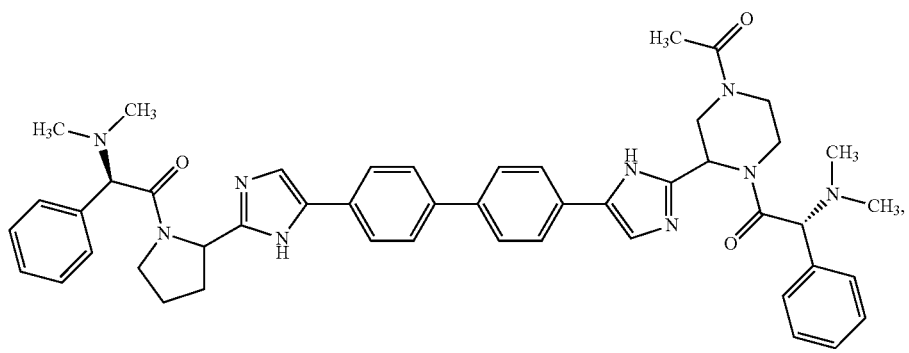

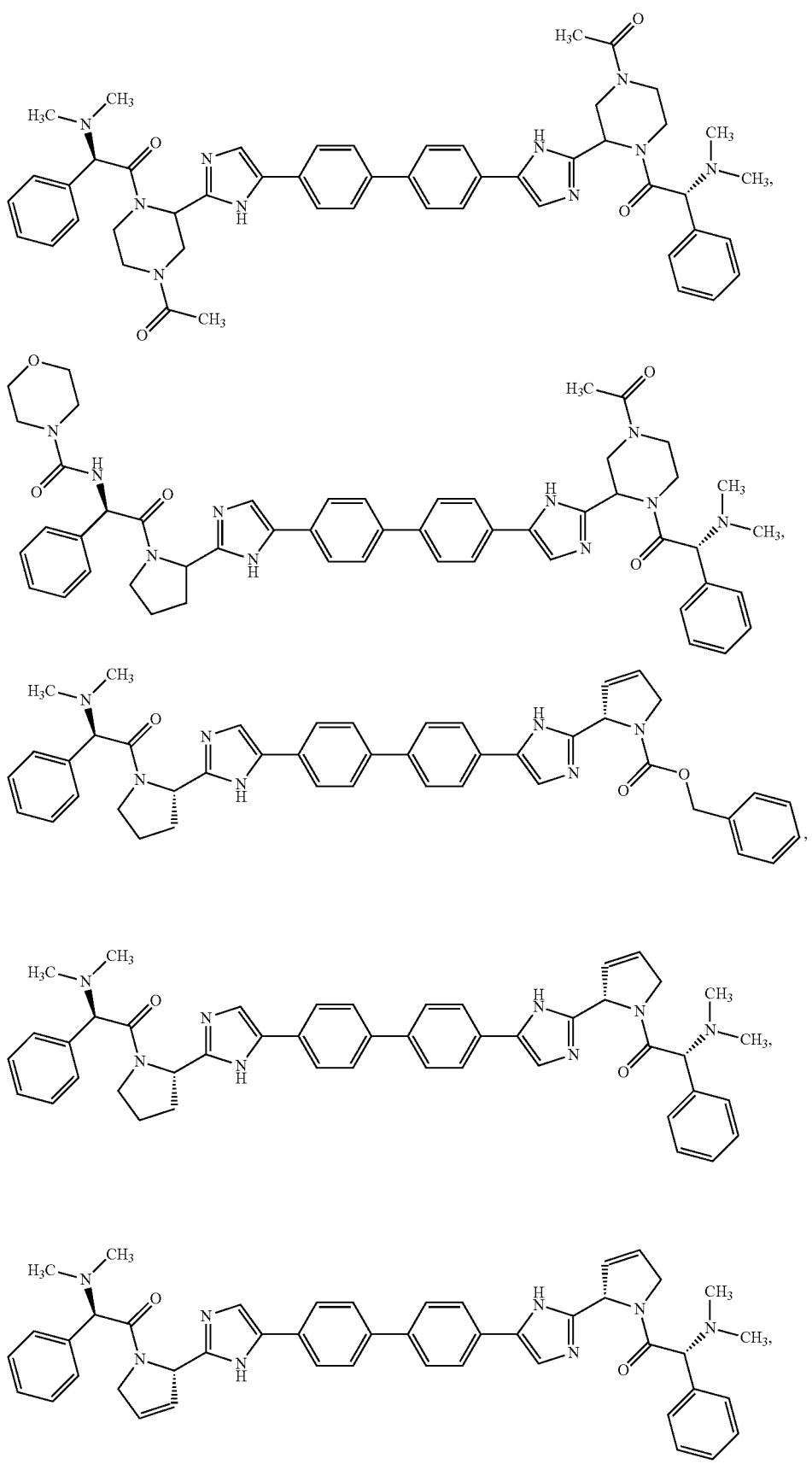

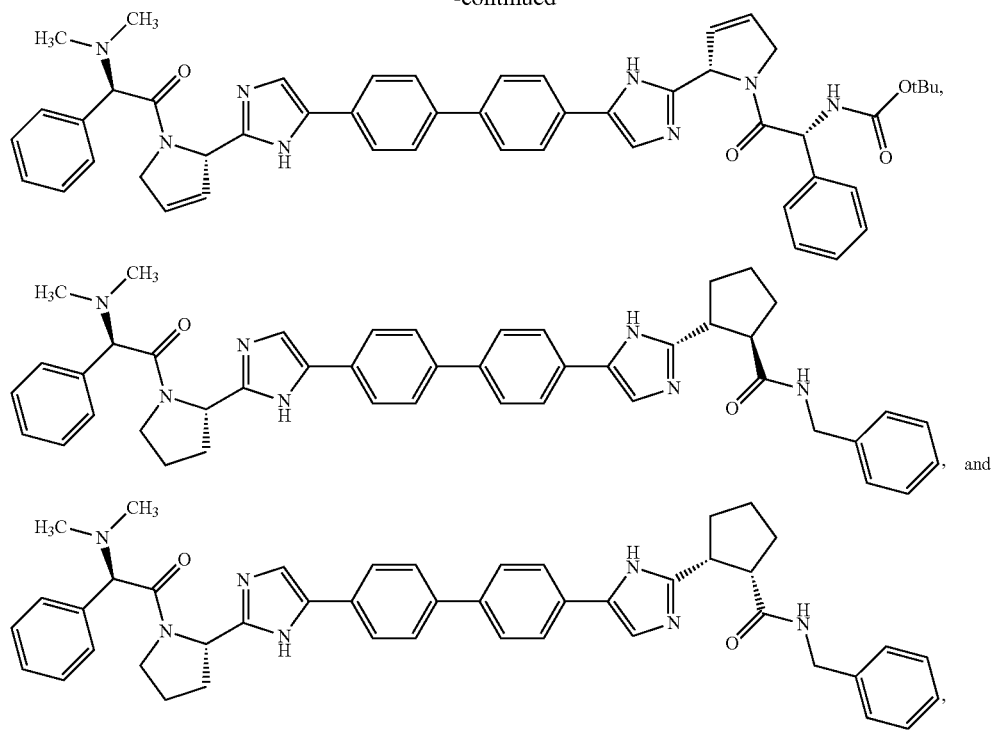

or a pharmaceutically acceptable salt thereof.

In one embodiment provided is a pharmaceutical composition comprising a pharmaceutically acceptable carrier and a therapeutically effective amount of a compound, stereoisomer, tautomer, or pharmaceutically acceptable salt of any one of Formula (I) or (II). In another embodiment provided is a method for treating a viral infection in a patient mediated at least in part by a virus in the Flaviviridae family of viruses, comprising administering to said patient such compositions. In some aspects, the viral infection is mediated by hepatitis C virus.

In other aspects, the administration of a therapeutically effective amount of the compounds and/or compositions of the invention are used in combination with one or more agents active against hepatitis C virus. These agents include an inhibitor of HCV proteases, HCV polymerase, HCV helicase, HCV NS4B protein, HCV entry, HCV assembly, HCV egress, HCV NS5A protein, or inosine 5'-monophosphate dehydrogenase. In other embodiments, the agent is interferon.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day. All of these factors are within the skill of the attending clinician.

Therapeutically effective amounts of compounds of Formula (I) or (II) may range from approximately 0.05 to 50 mg per kilogram body weight of the recipient per day; preferably about 0.1-25 mg/kg/day, more preferably from about 0.5 to 10 mg/kg/day. Thus, for administration to a 70 kg person, the dosage range would most preferably be about 35-70 mg per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration and bioavailability of the drug substance. For delivery via inhalation the compound can be formulated with a carrier as a liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula (I) or (II) in combination with a pharmaceutically acceptable carrier. Acceptable carriers are non-toxic, aid administration, and do not adversely affect the therapeutic benefit of the compound of Formula (I) or (II). Such carriers include any solid, liquid, semi-solid or, in the case of an aerosol composition, gaseous excipients that are generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01-99.99 wt % of a compound of Formula (I) or (II) based on the total formulation, with the balance being one or more suitable pharmaceutical excipients. Preferably, the compound is present at a level of about 1-80 wt %. Representative pharmaceutical formulations containing a compound of Formula (I) or (II) are described below.

Additionally, the present invention is directed to a pharmaceutical composition comprising a therapeutically effective amount of a compound of the present invention in combination with a therapeutically effective amount of another active agent against RNA-dependent RNA virus and, in particular, against HCV.

References herein to agents active against HCV include, but are not limited to, ribavirin, levovirin, viramidine, thymosin alpha-1, an inhibitor of HCV NS3 serine protease, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as Roferon interferon available from Hoffman-LaRoche, Nutley, N.J.), interferon-α2b (such as Intron-A interferon available from Schering Corp., Kenilworth, N.J., USA), a consensus interferon, and a purified interferon-α product. For a discussion of ribavirin and its activity against HCV, see J. O, Saunders and S. A. Raybuck, "Inosine Monophosphate Dehydrogenase: Consideration of Structure, Kinetics and Therapeutic Potential," *Ann. Rep. Med. Chem.*, 35:201-210 (2000).

The agents active against hepatitis C virus also include agents that inhibit HCV proteases, HCV polymerase, HCV helicase, HCV NS4B protein, HCV entry, HCV assembly, HCV egress, HCV NS5A protein, and inosine 5'-monophosphate dehydrogenase. Other agents include nucleoside analogs for the treatment of an HCV infection. Still other compounds include those disclosed in WO 2004/014313 and WO 2004/014852 and in the references cited therein. The patent applications WO 2004/014313 and WO 2004/014852 are hereby incorporated by references in their entirety.

Specific antiviral agents include Omega IFN (BioMedicines Inc.), BILN-2061 (Boehringer Ingelheim), Summetrel (Endo Pharmaceuticals Holdings Inc.), Roferon A (F. Hoffman-La Roche), Pegasys (F. Hoffman-La Roche), Pegasys/Ribaravin (F. Hoffman-La Roche), CellCept (F. Hoffman-La Roche), Wellferon (GlaxoSmithKline), Albuferon-α (Human Genome Sciences Inc.), Levovirin (ICN Pharmaceuticals), IDN-6556 (Idun Pharmaceuticals), IP-501 (Indevus Pharmaceuticals), Actimmune (InterMune Inc.), Infergen A (InterMune Inc.), ISIS 14803 (ISIS Pharmaceuticals Inc.), JTK-003 (Japan Tobacco Inc.), Pegasys/Ceplene (Maxim Pharmaceuticals), Ceplene (Maxim Pharmaceuticals), Civacir (Nabi Biopharmaceuticals Inc.), Intron A/Zadaxin (RegeneRx), Levovirin (Ribapharm Inc.), Viramidine (Ribapharm Inc.), Heptazyme (Ribozyme Pharmaceuticals), Intron A (Schering-Plough), PEG-Intron (Schering-Plough), Rebetron (Schering-Plough), Ribavirin (Schering-Plough), PEG-Intron/Ribavirin (Schering-Plough), Zadazim (SciClone), Rebif (Serono), IFN-β/EMZ701 (Transition Therapeutics), T67 (Tularik Inc.), VX-497 (Vertex Pharmaceuticals Inc.), VX-950/LY-570310 (Vertex Pharmaceuticals Inc.), Omniferon (Viragen Inc.), XTL-002 (XTL Biopharmaceuticals), SCH 503034 (Schering-Plough), isatoribine and its prodrugs ANA971 and ANA975 (Anadys), R1479 (Roche Biosciences), Valopicitabine (Idenix), NIM811 (Novartis), and Actilon (Coley Pharmaceuticals).

In some embodiments, the compositions and methods of the present invention contain a compound of Formula (I) and/or (II) and interferon. In some aspects, the interferon is selected from the group consisting of interferon alpha 2B, pegylated interferon alpha, consensus interferon, interferon alpha 2A, and lymphoblastoid interferon tau.

In other embodiments the compositions and methods of the present invention contain a compound of Formula (I) and/or (II) and a compound having anti-HCV activity is selected from the group consisting of interleukin 2, interleukin 6, interleukin 12, a compound that enhances the development of a type 1 helper T cell response, interfering RNA, anti-sense RNA, Imiquimod, ribavirin, an inosine 5' monophosphate dehydrogenase inhibitor, amantadine, and rimantadine.

General Synthetic Methods

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the compounds of this invention contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley and Sons, 1991), Rodd's *Chemistry of Carbon Compounds*, Volumes 1-5 and Supplementals (Elsevier Science Publishers, 1989), *Organic Reactions*, Volumes 1-40 (John Wiley and Sons, 1991), March's *Advanced Organic Chemistry*, (John Wiley and Sons, 4$^{th}$ Edition), and Larock's *Comprehensive Organic Transformations* (VCH Publishers Inc., 1989).

The various starting materials, intermediates, and compounds of the invention may be isolated and purified where appropriate using conventional techniques such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

A variety of amide coupling reagents may be used to from the amide bond, including the use of carbodiimides such as N—N'-dicyclohexylcarbodiimide (DCC), N—N'-diisopropylcarbodiimide (DIPCDI), and 1-ethyl-3-(3'-dimethylaminopropyl)carbodiimide (EDCI). The carbodiimides may be used in conjunction with additives such as benzotriazoles 7-aza-1-hydroxybenzotriazole (HOAt), 1-hydroxybenzotriazole (HOBt), and 6-chloro-1-hydroxybenzotriazole (Cl-HOBt).

Amide coupling reagents also include aminimum and phosphonium based reagents. Aminium salts include N-[(dimethylamino)-1H-1,2,3-triazolo[4,5-b]pyridine-1-ylmethylene]-N-methylmethanaminium hexafluorophosphate N-oxide (HATU), N-[(1H-benzotriazol-1-yl)(dimethylamino)methylene]-N-methylmethanaminium hexafluorophosphate N-oxide (HBTU), N-[(1H-6-chlorobenzotriazol-1-yl)(dimethylamino)methylene]-N-methylmethanaminium hexafluorophosphate N-oxide (HCTU), N-[(1H-benzotriazol-1-yl)(dimethylamino)methylene]-N-methylmethanaminium tetrafluoroborate N-oxide (TBTU), and N-[(1H-6-chlorobenzotriazol-1-yl)(dimethylamino)methylene]-N-methylmethanaminium tetrafluoroborate N-oxide (TCTU). Phosphonium salts include 7-azabenzotriazol-1-yl-N-oxy-tris(pyrrolidino)phosphonium hexafluorophosphate (PyAOP) and benzotriazol-1-yl-N-oxy-tris(pyrrolidino) phosphonium hexafluorophosphate (PyBOP).

The amide formation step may be conducted in a polar solvent such as dimethylformamide (DMF) and may also include an organic base such as diisopropylethylamine (DIPEA).

Schemes 1 shows a general synthesis of the compounds of Formula (I). For illustrative purposes, $Ar^1$ and $Ar^2$ are phenyl and u is 0. Amide 1.1 is coupled with acid 1.2 under amide forming conditions to provide 1.3. Treatment of 1.3 with ammonium acetate under ring forming conditions gives imidazole 1.4. Coupling of 1.4 and 1.5 with a suitable metal catalyst such as a Pd(0) catalyst gives the bis-aryl compound 1.6 that can be further functionalized to give 1.7.

Scheme 1

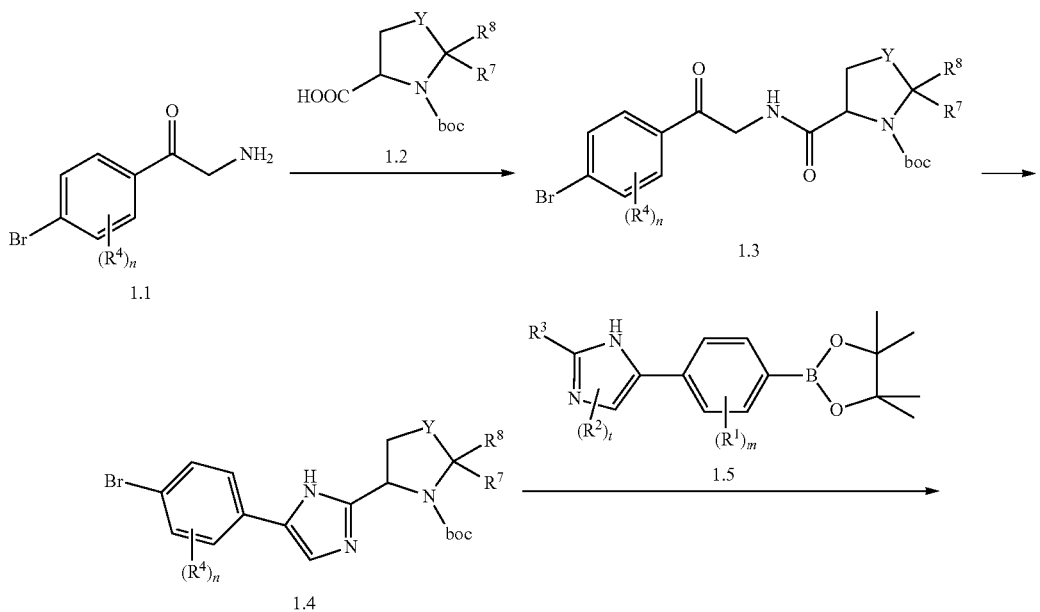

-continued
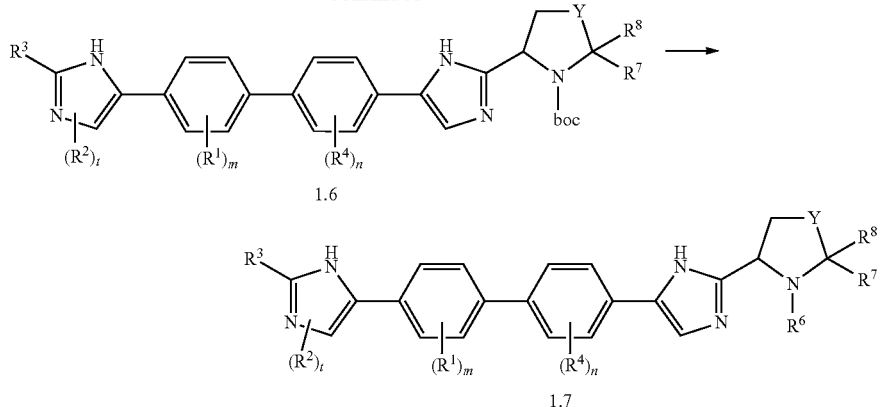
Compounds of Formula (II) may similarly be prepared according to Schemes 2-3 above, replacing 1.2 with the appropriate HOOC-Q group.
Scheme 2
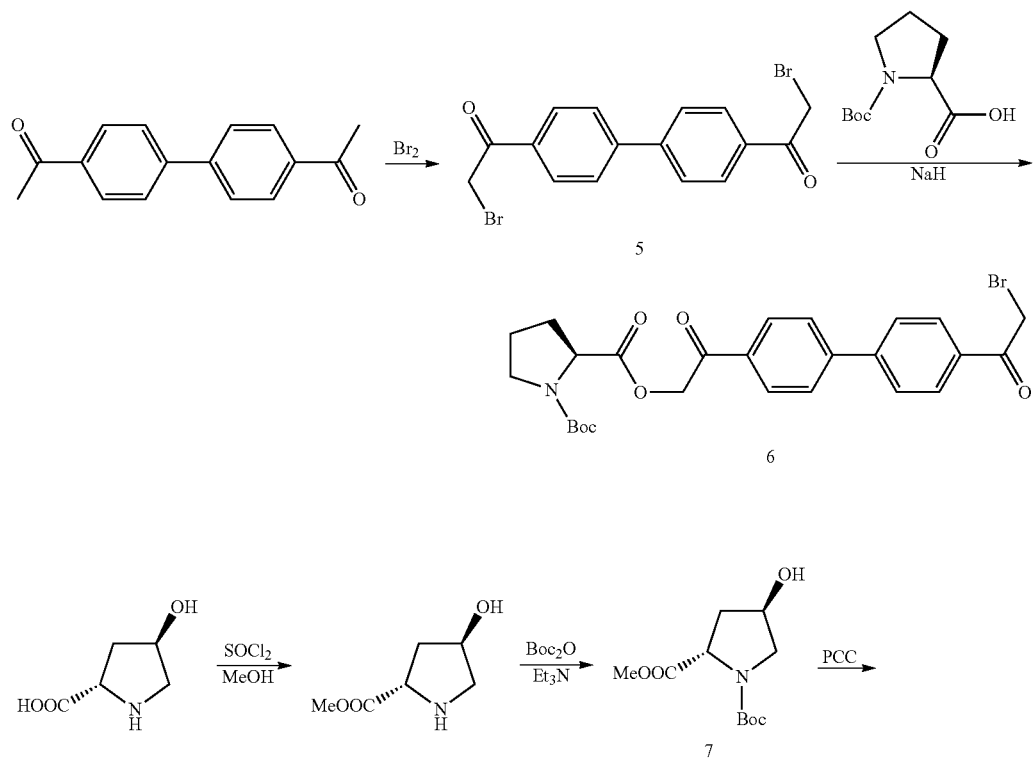
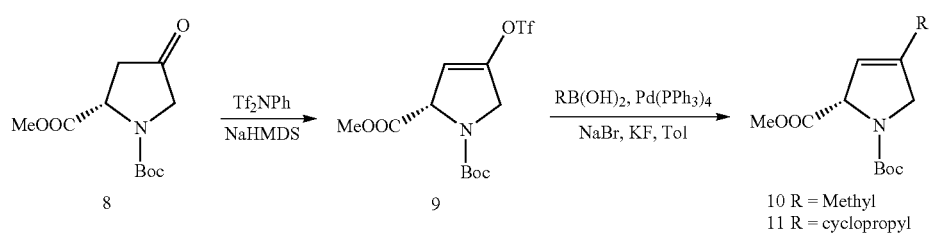

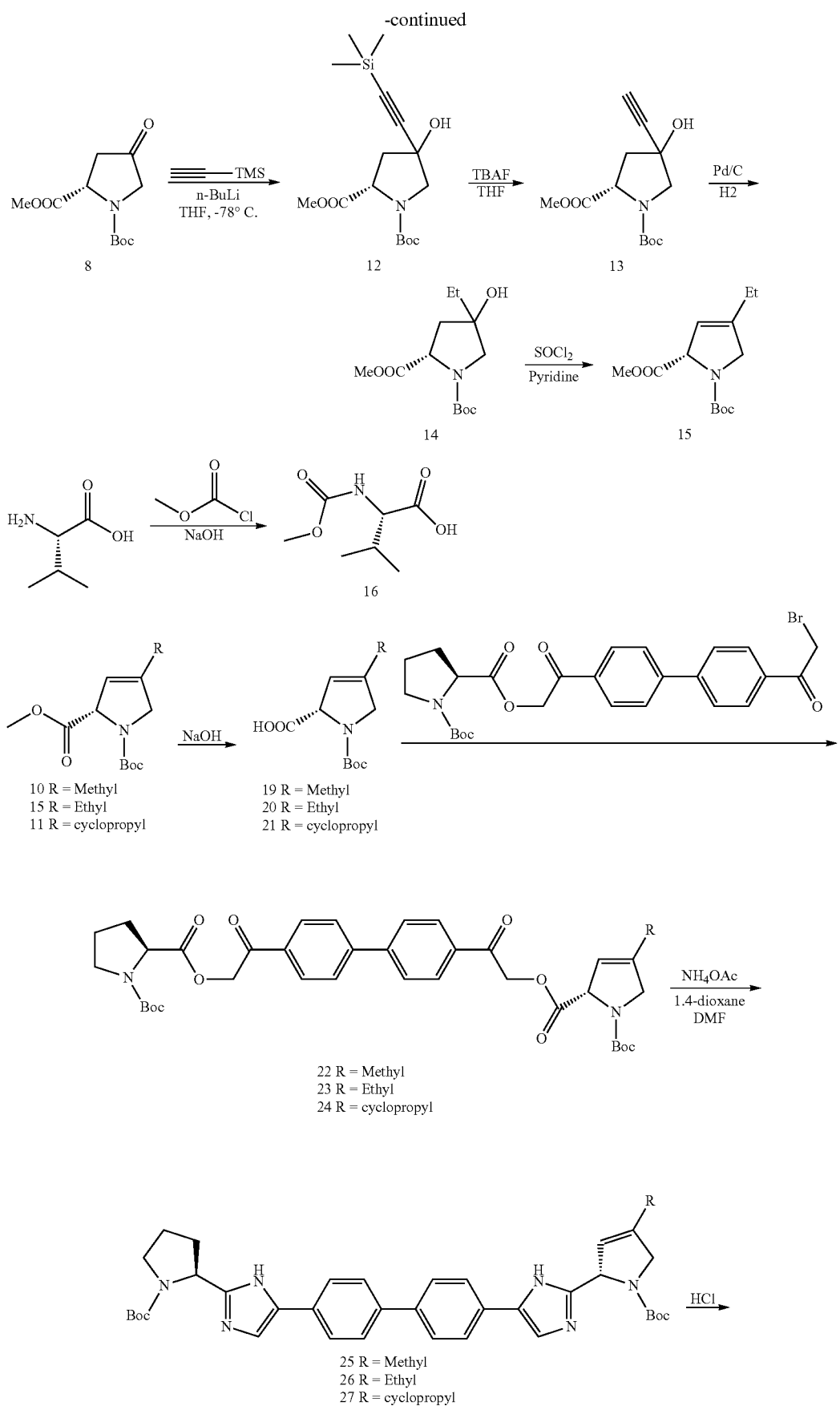

-continued
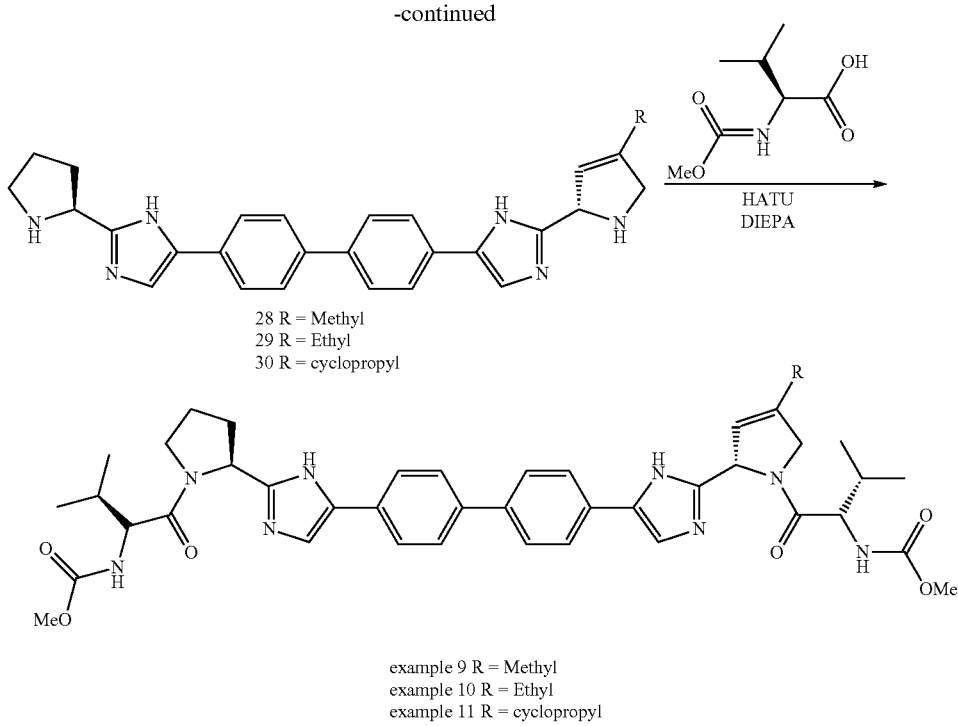
28 R = Methyl
29 R = Ethyl
30 R = cyclopropyl
example 9 R = Methyl
example 10 R = Ethyl
example 11 R = cyclopropyl
Scheme 3
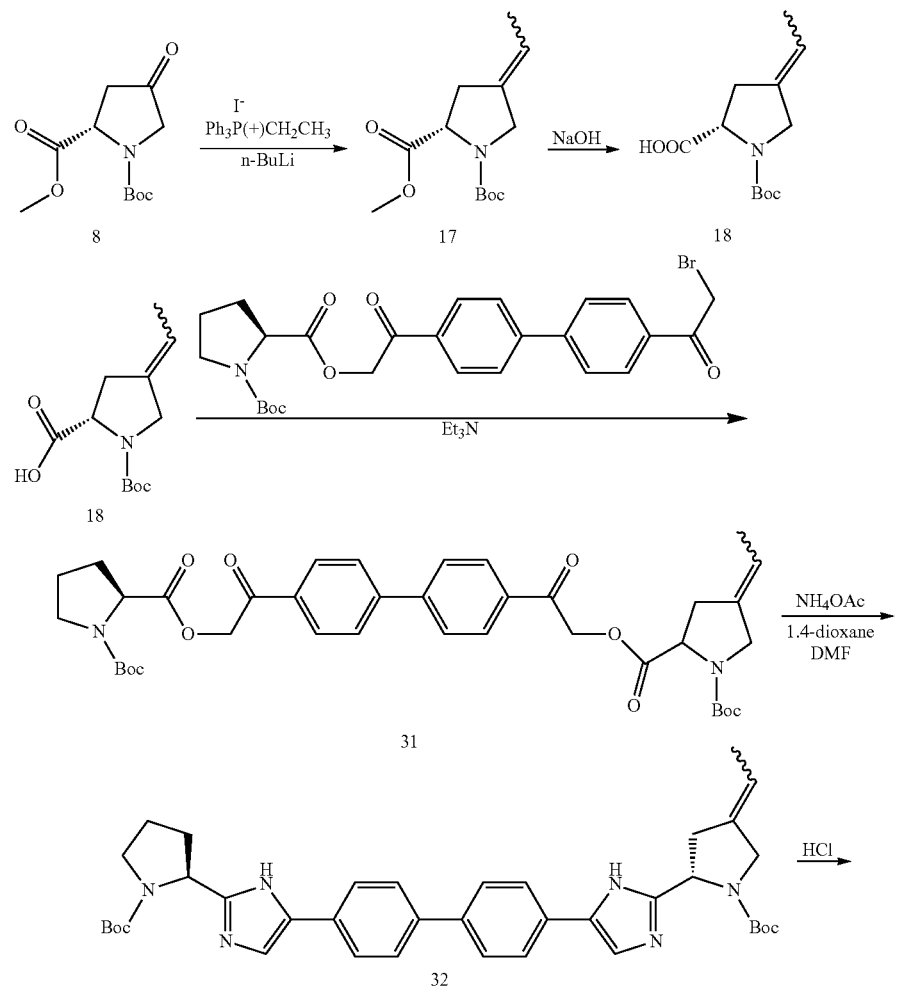

-continued

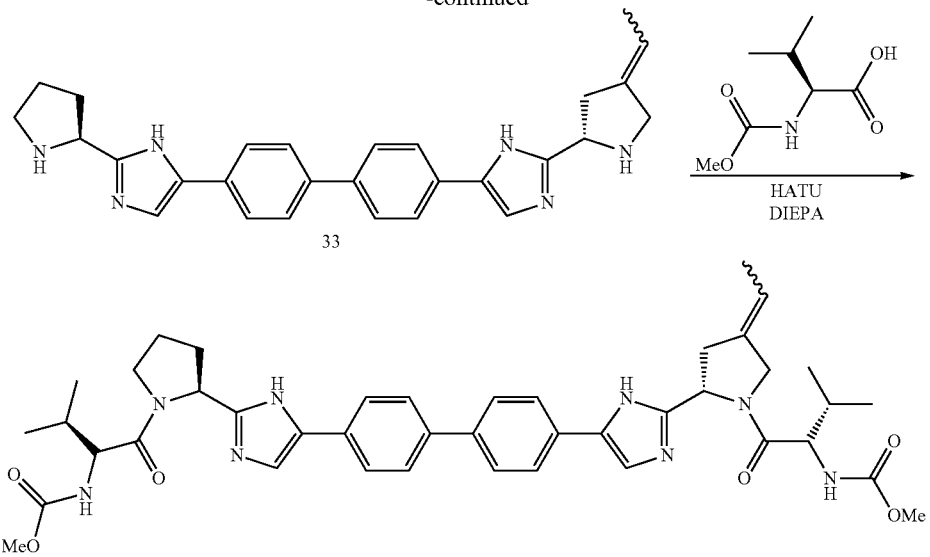

example 12

The forgoing and other aspects of the present invention may be better understood in connection with the following representative examples.

SYNTHETIC EXAMPLES

In the examples below and the synthetic schemes above, the following abbreviations have the following meanings. If an abbreviation is not defined, it has its generally accepted meaning

| aq. | aqueous |
|---|---|
| μL | microliters |
| μM | micromolar |
| NMR | nuclear magnetic resonance |
| boc | tert-butoxycarbonyl |
| br | broad |
| Cbz | benzyloxycarbonyl |
| d | doublet |
| δ | chemical shift |
| ° C. | degrees celcius |
| DCM | dichloromethane |
| dd | doublet of doublets |
| DMEM | Dulbeco's Modified Eagle's Medium |
| DMF | N,N-dimethylformamide |
| DMSO | dimethylsulfoxide |
| EtOAc | ethyl acetate |
| g | gram |
| h or hr | hours |
| HCV | hepatitis C virus |

-continued

| HPLC | high performance liquid chromatography |
|---|---|
| Hz | hertz |
| IU | International Units |
| $IC_{50}$ | inhibitory concentration at 50% inhibition |
| J | coupling constant (given in Hz unless otherwise indicated) |
| m | multiplet |
| M | molar |
| $M + H^+$ | parent mass spectrum peak plus $H^+$ |
| mg | milligram |
| mL | milliliter |
| mM | millimolar |
| mmol | millimole |
| MS | mass spectrum |
| nm | nanomolar |
| ppm | parts per million |
| q.s. | sufficient amount |
| s | singlet |
| sat. | saturated |
| t | triplet |
| TFA | trifluoroacetic acid |
| hr | hour |
| rt | Room temperature |
| ES LC-MS | Electrospray liquid chromatography mass spectroscopy |
| HATU | (O-7-azabenzotriazol-1-yl)-N,N,N',N'-tetramethyluronium hexafluorophosphate) |

Example 1

(R)-3-[4-(4'-{2-[(S)-1-[((R)-2-Dimethylamino-2-phenyl-acetyl)-pyrrolidin-2-yl]-1H-imidazol-4-yl}-biphenyl-4-yl)-1H-imidazol-2-yl]-1,8-dioxa-4-aza-spiro[4.5]decane-4-carboxylic acid benzyl ester

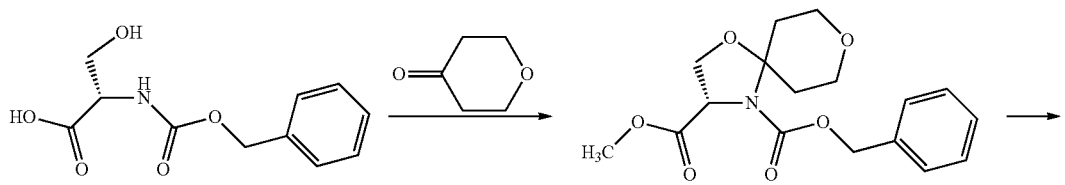

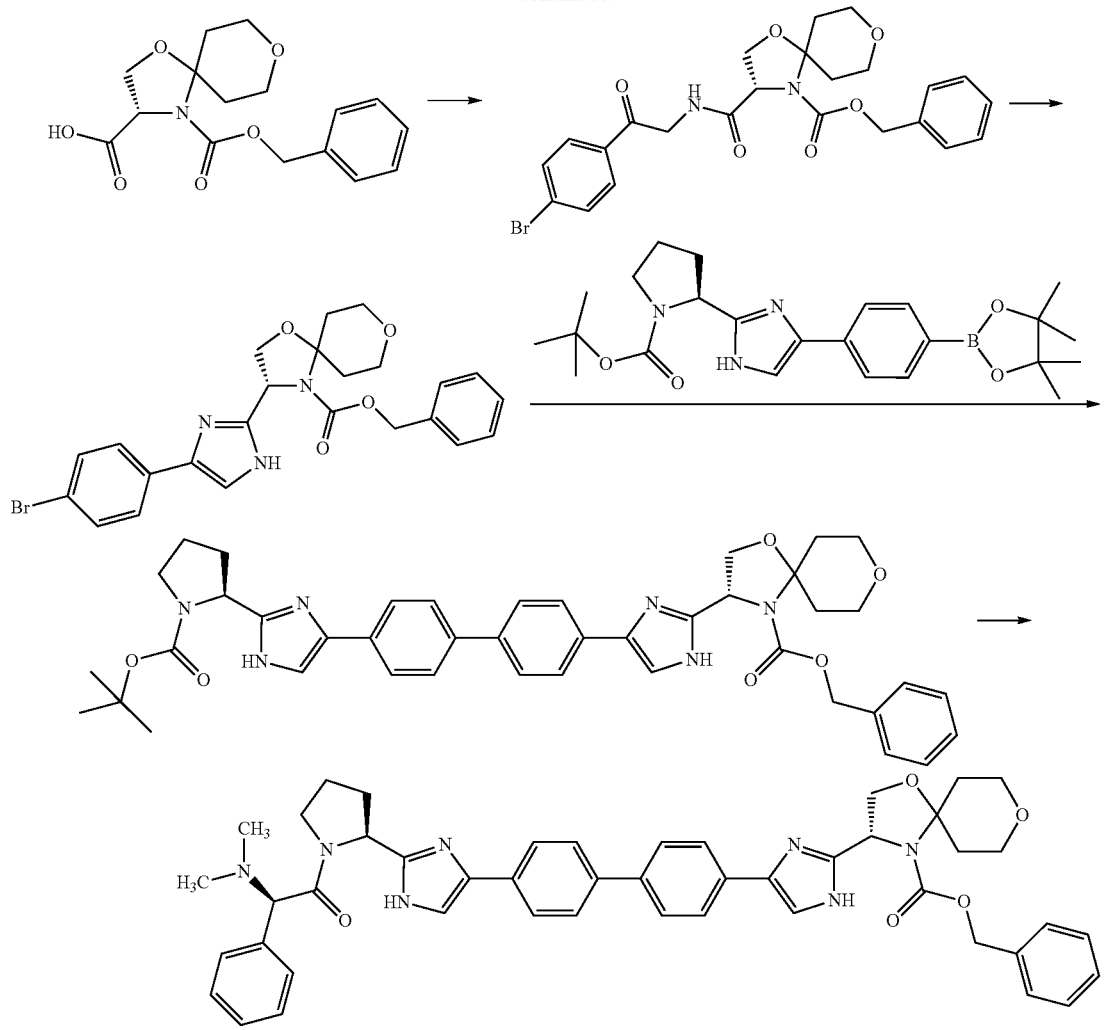

Step 1:
1,8-Dioxa-4-aza-spiro[4.5]decane-3,4-dicarboxylic acid 4-benzyl ester 3-methyl ester Step 2: (S)-3-[2-(4-Bromo-phenyl)-2-oxo-ethylcarbamoyl]-1,8-dioxa-4-aza-spiro[4.5]decane-4-carboxylic acid benzyl ester

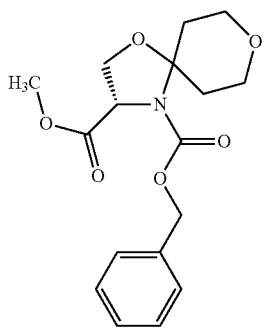 [SMILES: COC(=O)[C@@H]1COC2(CCOCC2)N1C(=O)OCc1ccccc1]

2-Benzyloxycarbonylamino-3-hydroxy-propionic acid methyl ester (2.0 g, 7.9 mmol) was combined with tetrahydropyran-4-one (790 mg, 7.9 mmol). This mixture was dissolved in 120 mL of dry toluene. Catalytic amount (50 mg) of p-toluenesulfonic acid was then added to the reaction mixture which was heated under reflux overnight. It was brought to room temperature, diluted using EtOAc, and extracted using NaHCO₃. Organic phase was isolated, dried over Na₂SO₄ and evaporated. The resulting clear oil was used in the next step without further purification.

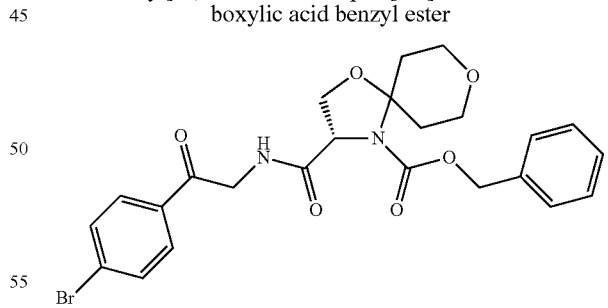

(S)-1,8-Dioxa-4-aza-spiro[4.5]decane-3,4-dicarboxylic acid 4-benzyl ester (1.05 gm, 3.27 mmol) was dissolved in DMF (10 mL) and the HCl salt of 2-amino-1-(4-bromo-phenyl)-ethanone (0.8 gm, 3.21 mmol) and HATU (1.34 gm, 3.5 mmol) were added, followed by diisopropylethyl amine (1.33 gm, 10.27 mmol). The mixture was stirred at room temperature for 3 hours, and then added dropwise into saturated aqueous NaHCO3 solution with stirring. The solid that crashed out was filtered and dried followed by redissolving (DCM) and filtration through a silica plug (eluting with ethyl acetate). This afforded 1.3 gm (78%) of the desired product as beige solid. LCMS: 519.2 (M+2).

Step 3: (R)-3-[4-(4-Bromo-phenyl)-1H-imidazol-2-yl]-1,8-dioxa-4-aza-spiro[4.5]decane-4-carboxylic acid benzyl ester

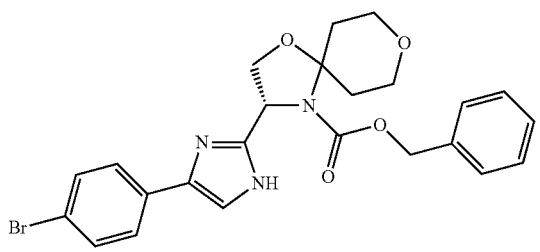 [SMILES: O=C(OCc1ccccc1)N1[C@H](c2nc(-c3ccc(Br)cc3)c[nH]2)COC12CCOCC2]

(S)-3-[2-(4-Bromo-phenyl)-2-oxo-ethylcarbamoyl]-1,8-dioxa-4-aza-spiro[4.5]decane-4-carboxylic acid benzyl ester (1.13 gm, 2.18 mmol) was dissolved in xylenes (11 mL), ammonium acetate (0.84 gm, 10.94 mmol) was added as a solid and the mixture was heated at 140° C. for 24 h. The mixture was diluted with ethyl acetate (50 mL) and the organic layer was washed (aqueous NaHCO3, water, brine) and dried. This crude product was purified by silica gel chromatography (3:2 mixture of EtOAc:hexanes) to afford 0.62 gm (57%) of the title compound. LCMS 500.9 (M+2)

Step 4: (R)-3-(4-{4'-[2-((S)-1-tert-Butoxycarbonyl-pyrrolidin-2-yl)-1H-imidazol-4-yl]-biphenyl-4-yl}-1H-imidazol-2-yl)-1,8-dioxa-4-aza-spiro[4.5]decane-4-carboxylic acid benzyl ester

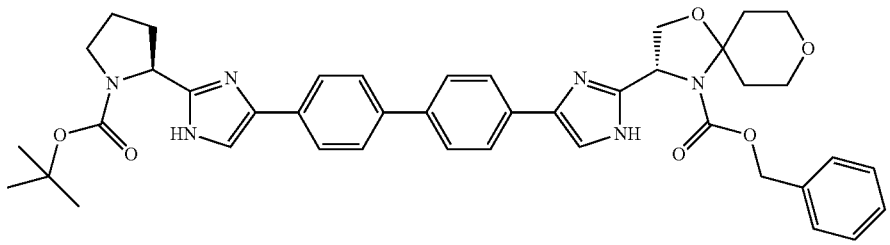 [SMILES: CC(C)(C)OC(=O)N1CCC[C@H]1c1nc(-c2ccc(-c3ccc(-c4c[nH]c([C@@H]5COC6(CCOCC6)N5C(=O)OCc5ccccc5)n4)cc3)cc2)c[nH]1]

(S)-2-{4-[4-(4,4,5,5-Tetramethyl-[1,3,2]dioxaborolan-2-yl)-phenyl]-1H-imidazol-2-yl}-pyrrolidine-1-carboxylic acid tert-butyl ester (0.213 gm, 0.48 mmol, synthesis described in WO0821928) and (R)-3-(4-{4'-[2-((S)-1-tert-butoxycarbonyl-pyrrolidin-2-yl)-1H-imidazol-4-yl]-biphenyl-4-yl}-1H-imidazol-2-yl)-1,8-dioxa-4-aza-spiro[4.5]decane-4-carboxylic acid benzyl ester (0.25 gm, 0.5 mmol) were dissolved in 1,4-dioxane (7 mL) and argon bubbled through briefly. Saturated aqueous NaHCO$_3$ (2 mL) was added followed by tetrakis triphenylphosphine palladium (0.014 gm, 0.03 mmol) and the resulting heterogeneous mixture was heated at 120° C. in the microwave for 10 minutes. The mixture was diluted with EtOAc (30 mL) and washed (water, brine) and dried to afford the crude product. Purification by preparative TLC (7% MeOH in DCM) afforded the desired product (0.04 g, 11%). LCMS 731.1 (M+1).

Step 5: (R)-3-[4-(4'-{2-[(S)-1-((R)-2-Dimethylamino-2-phenyl-acetyl)-pyrrolidin-2-yl]-1H-imidazol-4-yl}-biphenyl-4-yl)-1H-imidazol-2-yl]-1,8-dioxa-4-aza-spiro[4.5]decane-4-carboxylic acid benzyl ester

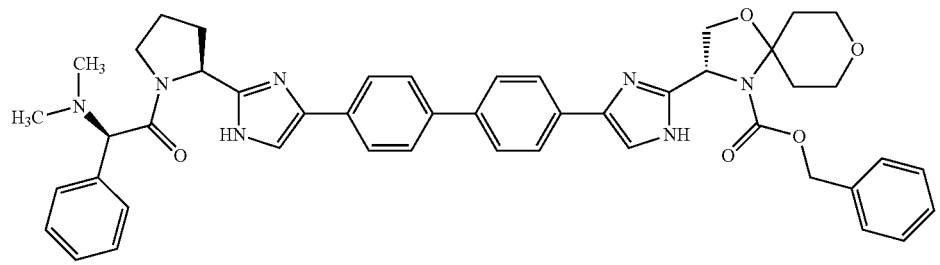 [SMILES: CN(C)[C@@H](C(=O)N1CCC[C@H]1c1nc(-c2ccc(-c3ccc(-c4c[nH]c([C@@H]5COC6(CCOCC6)N5C(=O)OCc5ccccc5)n4)cc3)cc2)c[nH]1)c1ccccc1]

(R)-3-(4-{4'-[2-((S)-1-tert-Butoxycarbonyl-pyrrolidin-2-yl)-1H-imidazol-4-yl]-biphenyl-4-yl}-1H-imidazol-2-yl)-1,8-dioxa-4-aza-spiro[4.5]decane-4-carboxylic acid benzyl ester (0.04 gm, 0.05 mmol) was dissolved in DCM (2 mL), TFA (2 mL) was added and the mixture stirred for 2 hours. The solvent was evaporated, the residue redissolved in EtOAc (20 mL) and the organics washed with aqueous NaHCO$_3$, water and brine. Drying the organic layer afforded (R)-3-{4-[4'-((S)-2-pyrrolidin-2-yl-1H-imidazol-4-yl)-biphenyl-4-yl]-1H-imidazol-2-yl}-1,8-dioxa-4-aza-spiro[4.5]decane-4-carboxylic acid benzyl ester (0.015 gm, 44%). LCMS 631.0 (M+1).

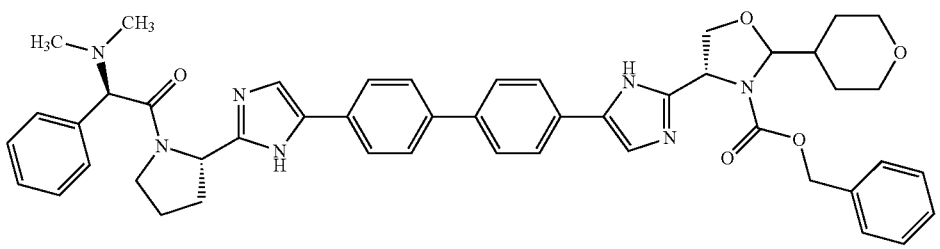

The crude product obtained above was dissolved in DMF (0.3 mL) and (R)-dimethylamino phenyl-acetic acid (0.004 gm, 0.024 mmol, synthesis described in WO0821928) and HBTU (0.01 gm, 0.026 mmol) were added followed by the addition of diisopropylethyl amine (0.011 mL, 0.06 mmol). The mixture was stirred at room temperature for 3 hours, and then added dropwise into saturated aqueous NaHCO$_3$ solution with stirring. The solid that crashed out was filtered, redissolved in a 10:1 mixture 0.01 N HCl and acetonitrile and subjected to purification by reverse phase HPLC to afford the desired product as a TFA salt (0.005 g, 26%).

LCMS 792.0 (M+1); 1H NMR (DMSO-d6) δ (ppm) 7.87 (br s, 10H), 7.60 (br s, 5H), 7.42-7.04 (br m, 6H), 5.43 (s, 1H), 5.35-4.99 (br m, 4H), 4.40-4.21 (br m, 2H), 4.09-3.78 (br m, 4H), 3.49 (br water peak), 3.20-2.61 (br m, 10H), 2.5-1.7 (br m, 10H, overlapping with DMSO peak).

Example 2

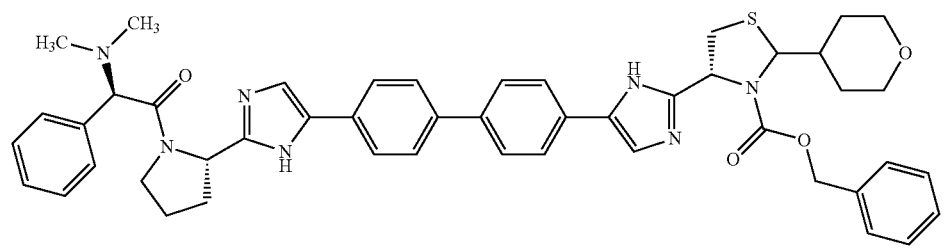

This compound can be similarly prepared according to Example 1 and the following Scheme:

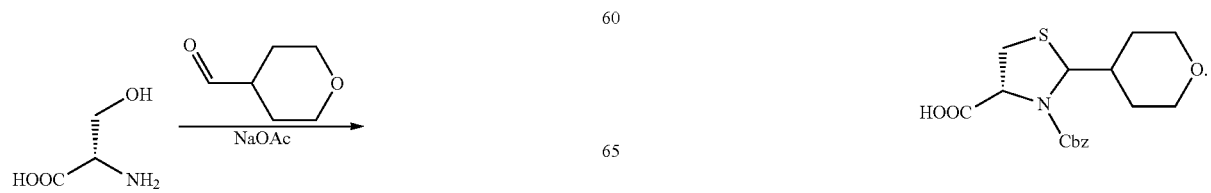

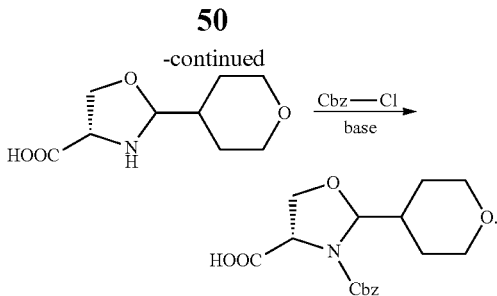

Example 3

This compound can be similarly prepared according to Example 1 and the following Scheme:

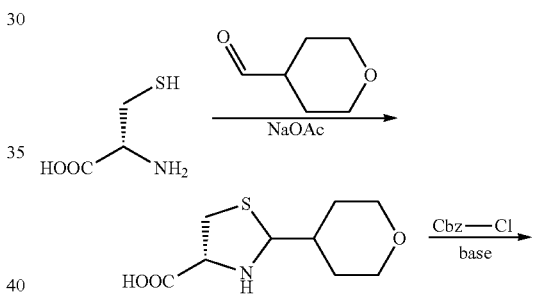

Example 4
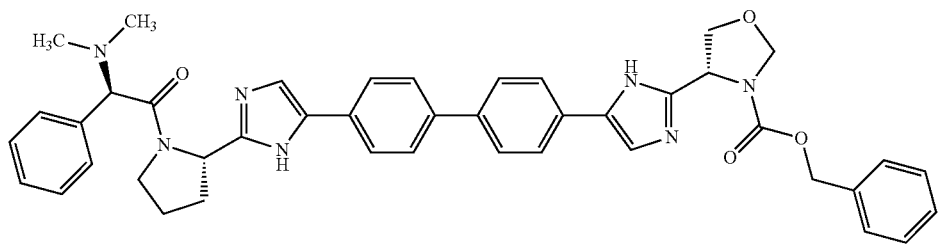 [SMILES: CN(C)[C@@H](C(=O)N1CCC[C@H]1c1ncc(-c2ccc(-c3ccc(-c4cnc([C@@H]5COCN5C(=O)OCc5ccccc5)[nH]4)cc3)cc2)[nH]1)c1ccccc1]
This compound can be similarly prepared according to Example 1 from
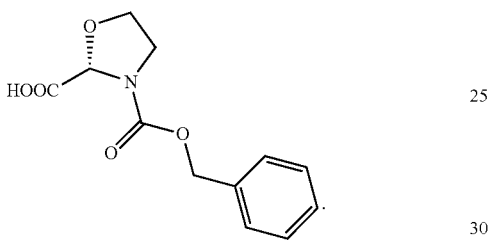
(Key Organics)
Example 5
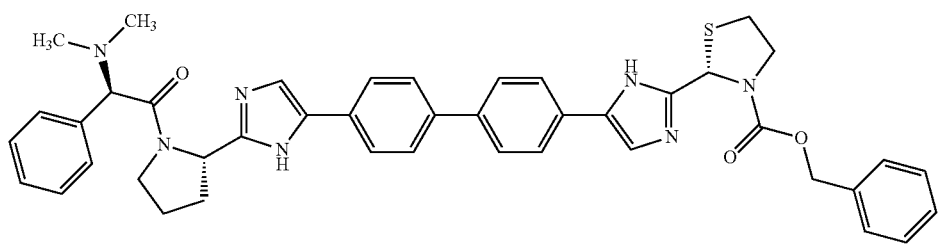 [SMILES: CN(C)[C@@H](C(=O)N1CCC[C@H]1c1ncc(-c2ccc(-c3ccc(-c4cnc([C@@H]5SCCN5C(=O)OCc5ccccc5)[nH]4)cc3)cc2)[nH]1)c1ccccc1]
This compound can be similarly prepared according to Example 1 from
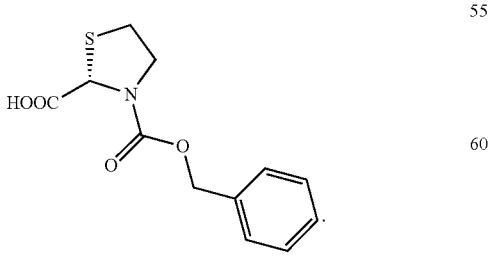
(Alfa Aesar)

Example 6
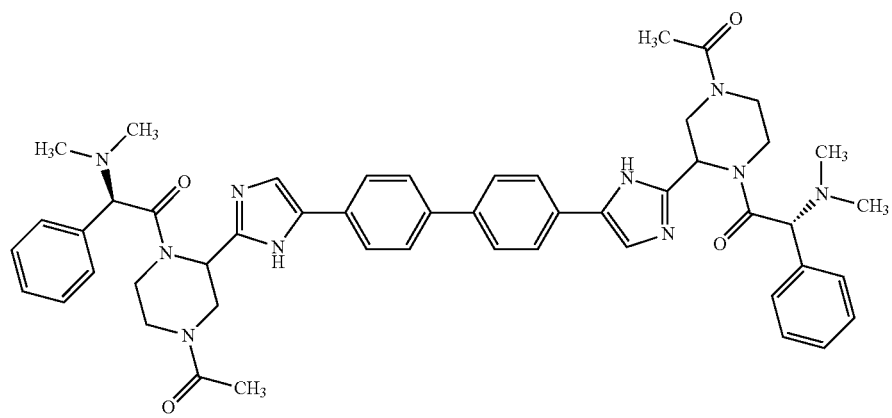 [SMILES: CC(=O)N1CCN(C(=O)[C@@H](c2ccccc2)N(C)C)C(c2ncc(-c3ccc(-c4ccc(-c5cnc(C6CN(C(C)=O)CCN6C(=O)[C@@H](c6ccccc6)N(C)C)[nH]5)cc4)cc3)[nH]2)C1]
This compound can be similarly prepared according to Example 1 from
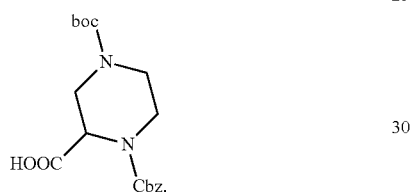
Example 7
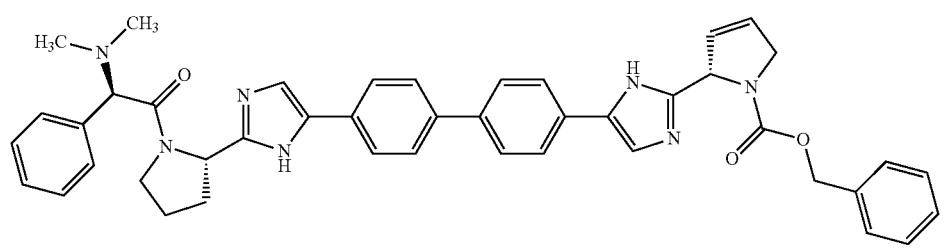 [SMILES: CN(C)[C@@H](C(=O)N1CCC[C@H]1c1ncc(-c2ccc(-c3ccc(-c4cnc([C@@H]5C=CCN5C(=O)OCc5ccccc5)[nH]4)cc3)cc2)[nH]1)c1ccccc1]
This compound can be similarly prepared according to Example 1 from
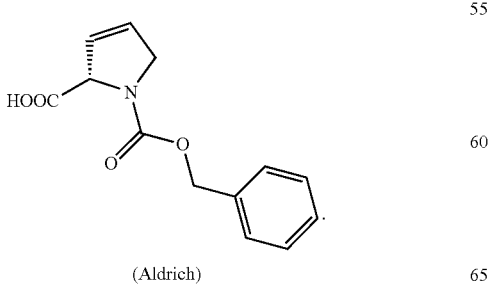
(Aldrich)

Example 8

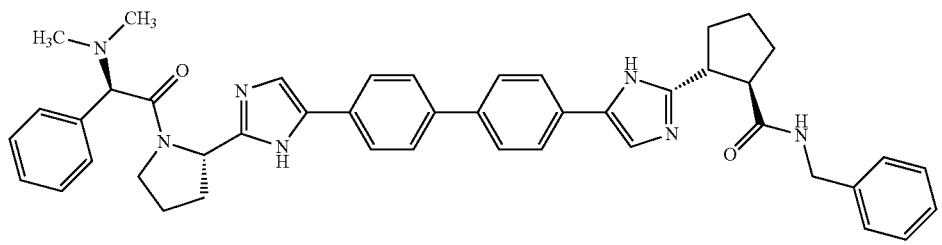

This compound can be similarly prepared according to Example 1 from

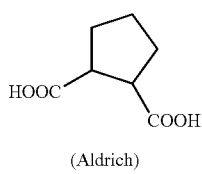 [SMILES: O=C(O)C1CCCC1C(=O)O]

(Aldrich)

and according to the following Scheme:

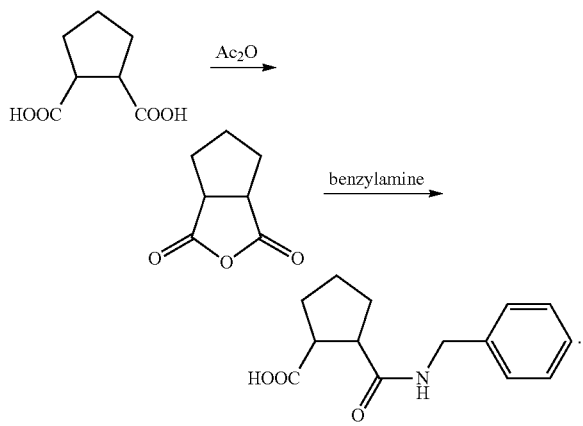

Intermediate 5: 1,1'-(biphenyl-4,4'-diyl)bis(2-bromoethanone)

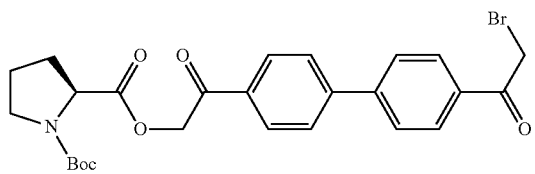

Br₂ (21.6 mL, 420 mmol) in DCM (60 mL) was added dropwise to a suspension of 1,1'-(biphenyl-4,4'-diyl)diethanone (50 g, 210 mmol) in DCM (500 mL). The mixture was stirred overnight, slurry filtered of washed with DCM to give intermediate 5 (67.4 g, yield: 81%) as a off-white solid. ¹H NMR (300 MHz, CDCl₃) δ ppm 8.11 (d, J=8.4 Hz, 4H), 7.76 (d, J=8.4 Hz, 4H), 4.49 (s, 4H).

Intermediate 6: (S)-2-(2-(4'-(2-bromoacetyl)biphenyl-4-yl)-2-oxoethyl) 1-tert-butyl pyrrolidine-1,2-dicarboxylate

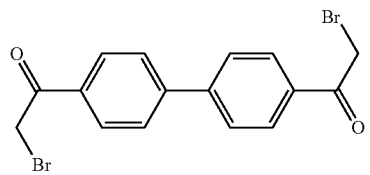 [SMILES: O=C(CBr)c1ccc(-c2ccc(C(=O)CBr)cc2)cc1]

To a stirred solution of (S)-1-(tert-butoxycarbonyl)pyrrolidine-2-carboxylic acid (10.15 g, 47.2 mmol) in DMF (186 mL) was added sodium hydride (1.25 g, 51.9 mmol). The mixture was stirred at rt for 1 h and then added 1,1'-(biphenyl-4,4'-diyl)bis(2-bromoethanone) (intermediate 5) (18.7 g, 47.2 mmol) in DMF (516 mL) in one portion. The mixture was stirred at rt for another 2 h, water (1.3 L) was added and exacted with EtOAc (200 mL×3). Combined organic phase was washed with brine, dried over Na₂SO₄ and concentrated to dryness. The product was purified by silica gel chromatography (petroleum ether/ethyl acetate=10/1 to 1/1) to give 2-{2-[4'-(bromoacetyl)-4-biphenylyl]-2-oxo ethyl}1-(1,1-dimethylethyl) (2S)-1,2-pyrrolidinedicarboxylate (intermediate 6) (9.5 g, yield: 38%) as a white foam. ¹H NMR (300 MHz, CDCl₃) δ ppm 8.00-8.12 (m, 2H), 7.69-7.76 (m, 2H), 5.22-5.64 (m, 2H), 4.41-4.52 (m, 3H), 3.39-3.59 (m, 2H), 2.25-2.38 (m, 2H), 1.93-2.08 (m, 2H), 1.47-1.55 (m, 9H).

Intermediate 7: (2S,4R)-1-tert-butyl 2-methyl 4-hydroxypyrrolidine-1,2-dicarboxylate Thionyl chloride (47 g, 0.393 mol) was added drowise at 0° C. to a stirred solution of (2S,4R)-4-hydroxypyrrolidine-2-carboxylic acid (40 g, 0.31 mol) in methanol (200 mL). The reaction was allowed to proceed overnight, methanol removed, the residue redissolved in DCM (200 mL) and the organic phase was washed with 10% NaHCO₃(aq) (50 mL) and brine. Next, di-tert-butyldicarbonate (86.6 g, 0.393 mol) and triethylamine (46.3 g, 0.46 mol) were added at 0° C. to the organic phase and stirred overnight at room temperature. The mixture was washed with 1N HCl (50 mL) and brine, dried over Na₂SO₄, concentrated to give (2S,4R)-1-tert-butyl 2-methyl 4-hydroxypyrrolidine-1,2-dicarboxylate (intermediate 7) (46 g, yield: 62%) as a white solid. ¹H NMR (300 MHz, CDCl₃) δ ppm 4.50 (br, 1H), 4.39-4.45 (m, 1H), 3.74 (s, 3H), 3.65 (m, 1H), 2.05-2.32 (m, 3H), 1.43-1.47 (m, 9H)

Intermediate 8: (S)-1-tert-butyl 2-methyl 4-oxopyrrolidine-1,2-dicarboxylate

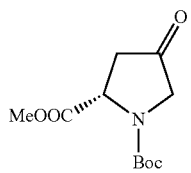

Pyridinium chlorochromate (21 g, 98 mmol) was added portionwise to a stirred solution of (2S,4R)-1-tert-butyl 2-methyl 4-hydroxypyrrolidine-1,2-dicarboxylate (intermediate 7) (12 g, 49 mmol) in DCM (200 mL) and the mixture was stirred at rt for 4 h. Next, the reaction was filtered through celite, filtrate concentrated and purified by silica gel chromatography (petroleum ether/ethyl acetate=2/1) to give (S)-1-tert-butyl 2-methyl 4-oxopyrrolidine-1,2-dicarboxylate (intermediate 8) (10 g, yield: 84%) as a colorless oil. ¹H NMR (300 MHz, CDCl₃) δ ppm 4.74 (m, 1H), 3.85-3.87 (m, 2H), 3.74 (s, 3H), 2.86-2.95 (m, 1H), 2.55 (m, 1H), 1.43 (s, 9H)

Intermediate 9: (S)-1-tert-butyl 2-methyl 4-(trifluoromethylsulfonyloxy)-2H-pyrrole-1,2(5H)-dicarboxylate

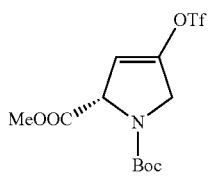

2N NaHMDS (20 mL, 40 mmol) was added to a stirred solution of (S)-1-tert-butyl 2-methyl 4-oxopyrrolidine-1,2-dicarboxylate (intermediate 8) (9.8 g, 40 mmol) in dry THF (50 mL) at −78° C. under nitrogen. After stirring at −78° C. for 30 min, solution of trifluoro-N-phenyl-N-(trifluoromethylsulfonyl)methanesulfonamide (15 g, 42 mmol) in THF (50 mL) was added dropwise and mixture stirred at −78° C. for another 2 h, and then reaction allowed to proceed overnight at ambient temperature. The reaction was quenched with NH₄Cl (aq) and product extracted with EtOAc (100 mL×3). The combined organic phase was washed with brine, dried over Na₂SO₄ and concentrated. Following silica gel purification (petroleum ether/ethyl acetate=20/1) (S)-1-tert-butyl 2-methyl 4-(trifluoromethylsulfonyloxy)-2H-pyrrole-1,2(5H)-dicarboxylate (intermediate 9) (13.6 g, yield: 91%) was obtained as yellow oil. ¹H NMR (300 MHz, CDCl₃) δ ppm 5.72 (dd, J=13.8 Hz, 1.2 Hz, 1H), 4.99-5.07 (m, 1H), 4.28-4.42 (m, 2H), 3.76 (s, 3H), 1.42-1.47 (m, 9H).

Intermediate 10: (S)-1-tert-butyl 2-methyl 4-methyl-2H-pyrrole-1,2(5H)-dicarboxylate

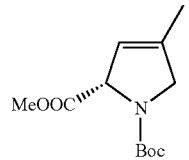 [SMILES: COC(=O)[C@@H]1C=C(C)CN1C(=O)OC(C)(C)C]

Methylboronic acid (0.72 g, 12 mmol), NaBr (0.41 g, 4 mmol), KF (0.77 g, 13.2 mmol) and Pd (PPh₃)₄ (0.23 g, 0.2 mmol) were added to solution of (S)-1-tert-butyl 2-methyl 4-(trifluoromethylsulfonyloxy)-2H-pyrrole-1,2(5H)-dicarboxylate (intermediate 9) (7.5 g, 20 mmol) in toluene (50 mL). The flask was purged with nitrogen (3×) and refluxed for 5 h, then cooled down and filtered. The filtrate was concentrated in vacuo and residue purified by silica gel chromatography (petroleum ether/ethyl acetate=15/1) to give (S)-1-tert-butyl 2-methyl 4-methyl-2H-pyrrole-1,2(5H)-dicarboxylate (intermediate 10) (2.1 g, yield: 44%) as a colorless oil. ¹H NMR (300 MHz, CDCl₃) δ ppm 5.34 (d, J=13.5 Hz, 1H), 4.88-4.98 (m, 1H), 4.04-4.15 (m, 2H), 3.72 (s, 3H), 1.79 (s, 3H), 1.42-1.47 (m, 9H).

Intermediate 11: (S)-1-tert-butyl 2-methyl 4-cyclopropyl-2H-pyrrole-1,2(5H)-dicarboxylate

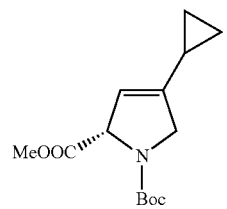 [SMILES: COC(=O)[C@@H]1C=C(C2CC2)CN1C(=O)OC(C)(C)C]

Cyclopropylboronic acid (5.28 g, 60 mmol), NaBr (2.05 g, 20 mmol), KF (3.83 g, 66 mmol) and Pd (PPh₃)₄ (1.15 g, 1 mmol) were added to a solution of (S)-1-tert-butyl 2-methyl 4-(trifluoromethylsulfonyloxy)-2H-pyrrole-1,2(5H)-dicarboxylate (intermediate 9) (1.5 g, 4 mmol) in toluene (20 mL). The flask was purged with nitrogen (3×), refluxed for 16 h, cooled down and filtered. The filtrate was concentrated in vacuo and residue purified by silica gel chromatography (petroleum ether/ethyl acetate=15/1) to yield (S)-1-tert-butyl 2-methyl 4-cyclopropyl-2H-pyrrole-1,2(5H)-dicarboxylate (intermediate 11) (0.32 g, yield: 30%) as a colorless oil. ¹H NMR (300 MHz, CDCl₃) δ ppm 5.29-5.32 (m, 1H), 4.88-4.97 (m, 1H), 3.95-4.13 (m, 2H), 3.70-3.72 (m, 3H), 1.42-1.47 (m, 9H). 1.25-1.32 (m, 1H), 0.73-0.77 (m, 2H), 0.53-0.55 (m, 2H).

Intermediate 12: (2S)-1-tert-butyl 2-methyl 4-hydroxy-4-((trimethylsilyl)ethynyl)pyrrolidine-1,2-dicarboxylate

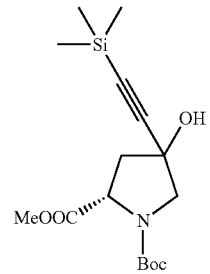

BuLi (1.6 M in hexane, 33 mL, 53.4 mmol) was added dropwise at −78° C. under nitrogen to a stirred solution of ethynyltrimethylsilane (4.8 g, 49.4 mmol) in THF (50 mL). After stirring for 1 h at −78° C. (S)-1-tert-butyl 2-methyl 4-oxopyrrolidine-1,2-dicarboxylate (intermediate 8) (10 g, 41.1 mmol) in THF (5 mL) was added at −78° C. and stirred for 2 h, then stirred for additional 1 hr at −40° C. After quenching with NH₄Cl (aq) and extraction with ethyl acetate (100 mL×3), combined organic phases were washed with brine, dried over sodium sulfate and concentrated to give crude (2S)-1-tert-butyl 2-methyl 4-hydroxy-4-((trimethylsilyl)ethynyl)pyrrolidine-1,2-dicarboxylate (intermediate 12) (9.6 g, yield: 68%), next used without further purification. ES LC-MS m/z=364, (M+Na)+.

Intermediate 13: (2S)-1-tert-butyl 2-methyl 4-ethynyl-4-hydroxypyrrolidine-1,2-dicarboxylate

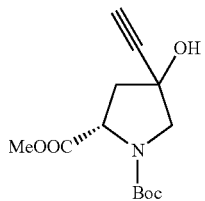 [SMILES: C#CC1(O)C[C@@H](C(=O)OC)N(C(=O)OC(C)(C)C)C1]

To a solution of (2S)-1-tert-butyl 2-methyl 4-hydroxy-4-((trimethylsilyl)ethynyl)pyrrolidine-1,2-dicarboxylate (intermediate 12) (9.6 g, 27.9 mmol) in THF (90 mL) was added TBAF (1 M in THF, 27.9 mL, 27.9 mmol). After stirring at rt for 2 h, the reaction was quench with water. The solution was extracted with EtOAc (150 mL×3) and the combined organic phase was washed with brine, dried over Na₂SO₄ and concentrated to dryness. Silica gel purification (petroleum ether/ethyl acetate=3/1) yielded (2S)-1-tert-butyl 2-methyl 4-ethynyl-4-hydroxypyrrolidine-1,2-dicarboxylate (intermediate 13) (4.1 g, yield: 55%) as a colorless oil. ¹H NMR (300 MHz, CDCl₃) δ ppm 4.41 (m, 1H), 3.67-3.86 (m, 5H), 2.50-2.68 (m, 2H), 2.34 (m, 1H), 1.41-1.46 (m, 9H).

Intermediate 14: (2S)-1-tert-butyl 2-methyl 4-ethyl-4-hydroxypyrrolidine-1,2-dicarboxylate

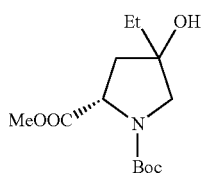 [SMILES: CCC1(O)C[C@@H](C(=O)OC)N(C(=O)OC(C)(C)C)C1]

To a solution of (2S)-1-tert-butyl 2-methyl 4-ethynyl-4-hydroxypyrrolidine-1,2-dicarboxylate (intermediate 13) (4.0 g, 14.8 mmol) in methanol (50 mL) was added Pd/C (0.4 g). After stirring at rt under hydrogen overnight, the reaction mixture was filtered through celite and filtrate concentrated to give (2S)-1-tert-butyl 2-methyl 4-ethyl-4-hydroxypyrrolidine-1,2-dicarboxylate (intermediate 14) (4.0 g, yield: 99%), used without further purification. ¹H NMR (300 MHz, CDCl₃) δ ppm 4.34 (m, 1H), 3.77-3.78 (s, 3H), 3.59-3.67 (m, 1H), 3.26-3.33 (m, 1H), 2.14-2.22 (m, 1H), 1.97-2.05 (m, 1H), 1.64 (q, J=7.2 Hz, 2H), 1.40-1.45 (s, 9H), 0.98 (t, J=7.2 Hz, 3H).

Intermediate 15: (S)-1-tert-butyl 2-methyl 4-ethyl-2H-pyrrole-1,2(5H)-dicarboxylate

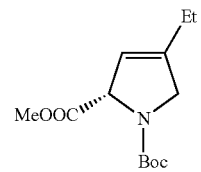 [SMILES: CCC1=C[C@@H](C(=O)OC)N(C(=O)OC(C)(C)C)C1]

Thionyl chloride (9.6 mL, 146 mmol) was added to a solution of (2S)-1-tert-butyl 2-methyl 4-ethyl-4-hydroxypyrrolidine-1,2-dicarboxylate (intermediate 14) (4.0 g, 14.6 mmol) in pyridine (100 mL) and the mixture refluxed for 20 min. After cooling to rt the reaction was quenched with water and extracted with Et₂O (150 mL×3). The combined organic phase was washed with 1N HCl (100 mL), NaHCO₃ (aq) (100 mL) and brine, dried over Na₂SO₄ and concentrated to dryness. Silica gel chromatography purification (petroleum ether/ethyl acetate=10/1) yielded (S)-1-tert-butyl 2-methyl 4-ethyl-2H-pyrrole-1,2(5H)-dicarboxylate (intermediate 15) (2.2 g, yield: 59%) as a colorless oil. ¹H NMR (300 MHz, CDCl₃) δ ppm 5.33 (m, 1H), 4.88-4.98 (m, 1H), 4.06-4.17 (m, 2H), 3.71-3.72 (s, 3H), 2.12 (q, J=7.5 Hz, 2H), 1.41-1.47 (m, 9H), 1.07 (t, J=7.5 Hz, 3H).

Intermediate 16: (S)-2-(methoxycarbonylamino)-3-methylbutanoic acid

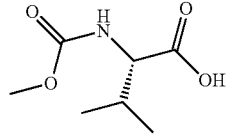

2N aqueous NaOH (1125 mL) and methyl chloroformate (91.8 mL, 1.185 mol) were added to a solution of L-Valine (87.9 g, 750 mmol) in dioxane (440 mL) and the reaction allowed to proceed at rt for 10 h. The mixture was washed with EtOAc (300 mL) and then the aqueous phase was acidified with 3 N HCl to pH=3 and extracted with EtOAc (300 mL×5). The combined organic phase was dried over Na₂SO₄, and concentrated to dryness. Recrytallization from petroleum ether/ethyl acetate=1/1 gave (S)-2-(methoxycarbonylamino)-3-methylbutanoic acid (intermediate 16) (139 g, yield: 70%) as a white solid. ¹H NMR (300 MHz, CDCl₃) δ 5.19 (d, J=8.1 Hz, 1H), 4.34-4.37 (m, 1H), 3.76 (s, 3H), 2.26-2.28 (m, 1H), 1.03 (d, J=6.9 Hz, 3H), 0.96 (d, J=6.9 Hz, 3H). ES LC-MS m/z=198, (M+Na)⁺

Intermediate 17: (S)-1-tert-butyl 2-methyl 4-ethylidenepyrrolidine-1,2-dicarboxylate

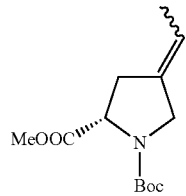

To a suspension of ethyltriphenylphosphonium iodide (20 g, 48 mmol) in toluene (100 mL) was added potassium tert-butyloxide (5.38 g, 48 mmol) and the mixture stirred at rt for 1 h. Following addition of (S)-1-tert-butyl 2-methyl 4-oxopyrrolidine-1,2-dicarboxylate (intermediate 8) (5.838 g, 24 mmol), the mixture was then heated at 65° C. for 40 min. After cooling to rt, the reaction was quenched with NH$_4$Cl (aq), organic phase separated and the aqueous phase exacted with EtOAc (100 mL×2). The combined organic phase was dried over Na$_2$SO$_4$, concentrated to give a residue which was purified by chromatography on silica gel (petroleum ether/ethyl acetate=5/1 to 3/1) to give (S)-1-tert-butyl 2-methyl 4-ethylidenepyrrolidine-1,2-dicarboxylate (intermediate 17) (1.04 g, yield: 17%) as a colorless oil. $^1$H NMR (300 MHz, CDCl$_3$) δ ppm 5.32-5.39 (m, 1H), 4.33-4.43 (m, 1H), 3.95-4.15 (m, 2H), 3.68 (s, 3H), 2.87-2.90 (m, 1H), 2.51-2.60 (m, 1H), 1.56-1.58 (m, 3H), 1.34-1.45 (m, 9H).

Intermediate 18: (S)-1-(tert-butoxycarbonyl)-4-ethylidenepyrrolidine-2-carboxylic acid

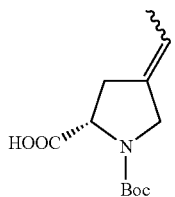

To a solution of (S)-1-tert-butyl 2-methyl 4-ethylidenepyrrolidine-1,2-dicarboxylate (intermediate 17) (0.92 g, 3.6 mmoL) in THF (3.5 mL), water (3.5 mL) and methanol (3.5 mL) was added LiOH (172 mg, 7.2 mmol). The reaction was stirred at rt overnight. The mixture was concentrated in vacuo, water (10 mL) and EtOAc (10 mL) added and acidified with 4 N HCl to pH=4. The aqueous phase was then extracted with DCM (10 mL×4) and combined organic phase was dried over Na$_2$SO$_4$, and concentrated to give (S)-1-(tert-butoxycarbonyl)-4-ethylidenepyrrolidine-2-carboxylic acid (intermediate 18) (0.79 g, yield: 91%) as a colorless oil. ES LC-MS m/z=264, (M+Na)$^+$.

Intermediate 19: (S)-1-(tert-butoxycarbonyl)-4-methyl-2,5-dihydro-1H-pyrrole-2-carboxylic acid

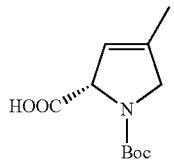

To a solution of (S)-1-tert-butyl 2-methyl 4-methyl-2H-pyrrole-1,2(5H)-dicarboxylate (intermediate 10) (2.1 g, 8.7 mmol) in THF (8 mL), water (8 mL) and methanol (8 mL) was added LiOH (0.42 g, 17.4 mmol). The reaction was stirred at rt overnight. The mixture was concentrated in vacuo and water (20 mL) was added. The solution was washed with EtOAc (20 mL), acidified with 4 N HCl to pH=4. The aqueous phase was extracted with DCM (20 mL×4). The combined organic phase was dried over Na$_2$SO$_4$, concentrated to give (S)-1-(tert-butoxycarbonyl)-4-methyl-2,5-dihydro-1H-pyrrole-2-carboxylic acid (intermediate 19) (1.82 g, yield: 92%) as a colorless oil. ES LC-MS m/z=250, (M+Na)$^+$.

Intermediate 20: (S)-1-(tert-butoxycarbonyl)-4-ethyl-2,5-dihydro-1H-pyrrole-2-carboxylic acid

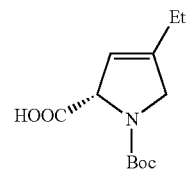 [SMILES: CCC1=C[C@@H](C(=O)O)N(C(=O)OC(C)(C)C)C1]

To a solution of (S)-1-tert-butyl 2-methyl 4-ethyl-2H-pyrrole-1,2(5H)-dicarboxylate (intermediate 15) (1.2 g, 4.98 mmol) in THF (5 mL), water (5 mL) and methanol (5 mL) was added LiOH (0.24 g, 10 mmol). The reaction was stirred at rt overnight. The mixture was concentrated in vacuo and water (20 mL) was added. The solution was washed with EtOAc (10 mL), acidified with 4 N HCl to pH=4. The aqueous phase was extracted with DCM (10 mL×4). The combined organic phase was dried over Na$_2$SO$_4$, concentrated to give (S)-1-(tert-butoxycarbonyl)-4-ethyl-2,5-dihydro-1H-pyrrole-2-carboxylic acid (intermediate 20) (1.0 g, yield: 88%) as a colorless oil. ES LC-MS m/z=264, (M+Na)$^+$ Intermediate 21: (S)-1-(tert-butoxycarbonyl)-4-cyclopropyl-2,5-dihydro-1H-pyrrole-2-carboxylic acid

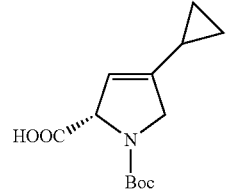 [SMILES: CC(C)(C)OC(=O)N1CC(C2CC2)=C[C@H]1C(=O)O]

LiOH (264 mg, 11 mmol) was added to a solution of (S)-1-tert-butyl 2-methyl 4-cyclopropyl-2H-pyrrole-1,2(5H)-dicarboxylate (intermediate 11) (1.47 g, 5.5 mmol) in THF (5 mL), water (5 mL) and methanol (5 mL) and the mixture stirred at rt overnight. The mixture was then concentrated in vacuo, water (20 mL) added and washed with EtOAc (10 mL) at pH=4 (adjusted with 4 N HCl). The aqueous phase was then extracted with DCM (10 mL×4) and the combined organic phase was dried over Na$_2$SO$_4$, concentrated to give (S)-1-(tert-butoxycarbonyl)-4-cyclopropyl-2,5-dihydro-1H-pyrrole-2-carboxylic acid (intermediate 21) (1.25 g, yield: 90%) as a colorless oil. ES LC-MS m/z=276, (M+Na)$^+$ Intermediate 22: (S)-2-(2-(4'-(2-((S)-1-(tert-butoxycarbonyl)pyrrolidine-2-carbonyloxy)acetyl)biphenyl-4-yl)-2-oxoethyl) 1-tert-butyl 4-methyl-2H-pyrrole-1,2(5H)-dicarboxylate

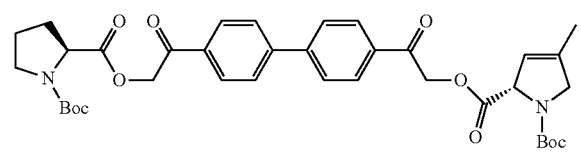 [SMILES: CC1=C[C@@H](C(=O)OCC(=O)c2ccc(-c3ccc(C(=O)COC(=O)[C@@H]4CCCN4C(=O)OC(C)(C)C)cc3)cc2)N(C(=O)OC(C)(C)C)C1]

(S)-2-(2-(4'-(2-bromoacetyl)biphenyl-4-yl)-2-oxoethyl) 1-tert-butyl pyrrolidine-1,2-dicarboxylate (intermediate 6) (0.63 g, 1.18 mmol) and diisopropylethylamine (0.46 g, 3.36 mmol) were added to a solution of (S)-1-(tert-butoxycarbonyl)-4-methyl-2,5-dihydro-1H-pyrrole-2-carboxylic acid (intermediate 19) (0.33 g, 1.42 mmol) in MeCN (15 mL) and the reaction allowed to proceed at rt for 3 h. Crude product was purified by on silica gel (petroleum ether/ethyl acetate=10/1 to 2/1) to give (S)-2-(2-(4'-(2-((S)-1-(tert-butoxycarbonyl)pyrrolidine-2-carbonyloxy)acetyl)biphenyl-4-yl)-2-oxoethyl) 1-tert-butyl 4-methyl-2H-pyrrole-1,2(5H)-dicarboxylate (intermediate 22) (0.55 g, yield: 69%) as a white solid. $^1$H NMR (300 MHz, CDCl$_3$) δ ppm 8.00-8.03 (m, 4H), 7.72-7.75 (m, 4H), 5.09-5.66 (m, 6H), 4.41-4.52 (m, 1H), 4.03-4.23 (m, 2H), 3.39-3.63 (m, 2H), 2.25-2.38 (m, 2H), 1.92-2.11 (m, 2H), 1.83 (s, 3H), 1.45-1.47 (m, 18H). ES LC-MS m/z=699, (M+Na)$^+$.

Intermediate 23: (S)-2-(2-(4'-(2-((S)-1-(tert-butoxycarbonyl)pyrrolidine-2-carbonyloxy)acetyl)biphenyl-4-yl)-2-oxoethyl) 1-tert-butyl 4-ethyl-2H-pyrrole-1,2(5H)-dicarboxylate

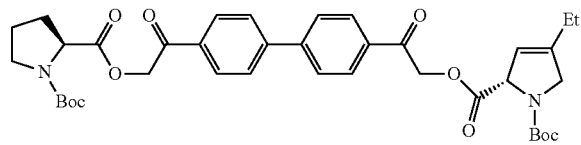 [SMILES: CCC1=C[C@@H](C(=O)OCC(=O)c2ccc(-c3ccc(C(=O)COC(=O)[C@@H]4CCCN4C(=O)OC(C)(C)C)cc3)cc2)N(C(=O)OC(C)(C)C)C1]

To a stirred solution of (S)-1-(tert-butoxycarbonyl)-4-ethyl-2,5-dihydro-1H-pyrrole-2-carboxylic acid (intermediate 20) (1.0 g, 4.4 mmol) in MeCN (40 mL) was added (S)-2-(2-(4'-(2-bromoacetyl)biphenyl-4-yl)-2-oxoethyl) 1-tert-butyl pyrrolidine-1,2-dicarboxylate (intermediate 6) (2.33 g, 4.4 mmol) and triethylamine (1.3 g, 13.2 mmol). The reaction was stirred at rt for 3 h. The resulting solution was concentrated to give a residue which was purified by chromatography on silica gel (petroleum ether/ethyl acetate=10/1 to 2/1) to give (S)-2-(2-(4'-(2-((S)-1-(tert-butoxycarbonyl)pyrrolidine-2-carbonyloxy)acetyl)biphenyl-4-yl)-2-oxoethyl) 1-tert-butyl 4-ethyl-2H-pyrrole-1,2(5H)-dicarboxylate (intermediate 23) (1.6 g, yield: 53%) as a white solid. ES LC-MS m/z=713, (M+Na)$^+$.

Intermediate 24: (S)-2-(2-(4'-(2-((S)-1-(tert-butoxycarbonyl)pyrrolidine-2-carbonyloxy)acetyl)biphenyl-4-yl)-2-oxoethyl) 1-tert-butyl 4-cyclopropyl-2H-pyrrole-1,2(5H)-dicarboxylate

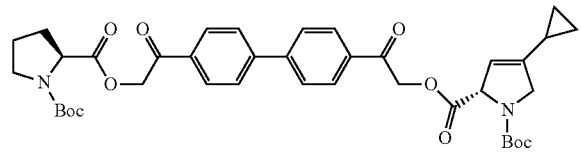 [SMILES: CC(C)(C)OC(=O)N1CC(C2CC2)=C[C@H]1C(=O)OCC(=O)c1ccc(-c2ccc(C(=O)COC(=O)[C@@H]3CCCN3C(=O)OC(C)(C)C)cc2)cc1]

To a stirred solution of (S)-1-(tert-butoxycarbonyl)-4-cyclopropyl-2,5-dihydro-1H-pyrrole-2-carboxylic acid (intermediate 21) (1.25 g, 4.9 mmol) in MeCN (50 mL) was added (S)-2-(2-(4'-(2-bromoacetyl)biphenyl-4-yl)-2-oxoethyl) 1-tert-butyl pyrrolidine-1,2-dicarboxylate (intermediate 6) (2.38 g, 4.5 mmol) and diisopropylethylamine (1.74 g, 13.5 mmol). The reaction was stirred at rt for 3 h. The resulting solution was concentrated to give a residue which was purified by chromatography on silica gel (petroleum ether/ethyl acetate=10/1 to 2/1) to give (S)-2-(2-(4'-(2-((S)-1-(tert-butoxycarbonyl)pyrrolidine-2-carbonyloxy)acetyl)biphenyl-4-yl)-2-oxoethyl) 1-tert-butyl 4-cyclopropyl-2H-pyrrole-1,2(5H)-dicarboxylate (intermediate 24) (1.79 g, yield: 56%) as a white solid. $^1$H NMR (300 MHz, CDCl$_3$) δ ppm 8.00-8.02 (m, 4H), 7.72-7.76 (m, 4H), 5.08-5.63 (m, 6H), 4.40-4.52 (m, 1H), 4.03-4.15 (m, 2H), 3.39-3.61 (m, 2H), 2.27-2.37 (m, 2H), 1.90-2.11 (m, 2H), 1.45-1.47 (m, 18H), 0.89-0.92 (m, 1H), 0.75-0.78 (m, 2H), 0.58-0.59 (m, 2H). ES LC-MS m/z=703, (M+H)$^+$.

Intermediate 31: (S)-2-(2-(4'-(2-((S)-1-(tert-butoxycarbonyl)pyrrolidine-2-carbonyloxy)acetyl)biphenyl-4-yl)-2-oxoethyl) 1-tert-butyl 4-ethylidenepyrrolidine-1,2-dicarboxylate

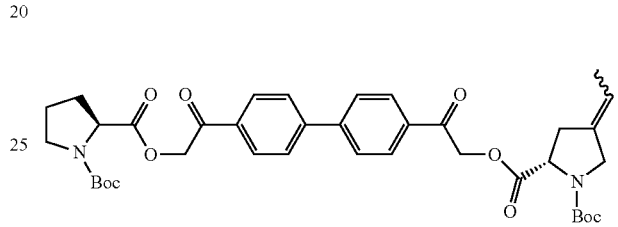

To a stirred solution of (S)-1-(tert-butoxycarbonyl)-4-ethylidenepyrrolidine-2-carboxylic acid (intermediate 18) (0.79 g, 3.27 mmol) in MeCN (30 mL) was added (S)-2-(2-(4'-(2-bromoacetyl)biphenyl-4-yl)-2-oxoethyl) 1-tert-butyl pyrrolidine-1,2-dicarboxylate (intermediate 6) (1.80 g, 3.27 mmol) and diisopropylethylamine (1.26 g, 9.83 mmol). The reaction was stirred at rt for 3 h. The resulting solution was concentrated to give a residue which was purified by chromatography on silica gel (petroleum ether/ethyl acetate=10/1 to 2/1) to give (S)-2-(2-(4'-(2-((S)-1-(tert-butoxycarbonyl)pyrrolidine-2-carbonyloxy)acetyl)biphenyl-4-yl)-2-oxoethyl) 1-tert-butyl 4-ethylidenepyrrolidine-1,2-dicarboxylate (intermediate 31) (677 mg, yield: 30%) as a white solid. $^1$H NMR (300 MHz, CDCl$_3$) δ ppm 7.99-8.01 (m, 4H), 7.71-7.74 (m, 4H), 5.18-5.62 (m, 5H), 4.40-4.66 (m, 2H), 4.01-4.15 (m, 2H), 3.39-3.64 (m, 2H), 2.88-3.04 (m, 2H), 2.25-2.37 (m, 2H), 1.92-2.07 (m, 2H), 1.67-1.70 (m, 3H), 1.45-1.47 (m, 18H). ES LC-MS m/z=713, (M+Na)$^+$ Intermediate 25: (S)-tert-butyl 2-(5-(4'-(2-((S)-1-(tert-butoxycarbonyl)pyrrolidin-2-yl)-1H-imidazol-5-yl)biphenyl-4-yl)-1H-imidazol-2-yl)-4-methyl-2H-pyrrole-1(5H)-carboxylate

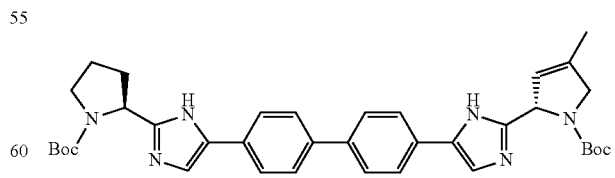

To a solution of (S)-2-(2-(4'-(2-((S)-1-(tert-butoxycarbonyl)pyrrolidine-2-carbonyloxy)acetyl)biphenyl-4-yl)-2-oxoethyl) 1-tert-butyl 4-methyl-2H-pyrrole-1,2(5H)-dicarboxylate (intermediate 22) (1.40 g, 2.1 mmol) in dioxane (7.5 mL) and DMF (2.5 mL) was added ammonium acetate (1.59 g, 21 mmol). The mixture was heated under microwave at 110° C. for 40 minutes. The mixture was concentrated and purified by flash chromatography (Ethyl Acetate:Petroleum Ether=1:1) to give (S)-tert-butyl 2-(5-(4'-(2-((S)-1-(tert-butoxycarbonyl)pyrrolidin-2-yl)-1H-imidazol-5-yl)biphenyl-4-yl)-1H-imidazol-2-yl)-4-methyl-2H-pyrrole-1(5H)-carboxylate (intermediate 25) (0.60 g, yield: 46%) as a light brown solid. ES LC-MS m/z=637 (M+H)+.

Intermediate 26: (S)-tert-butyl 2-(5-(4'-(2-((S)-1-(tert-butoxycarbonyl)pyrrolidin-2-yl)-1H-imidazol-5-yl)biphenyl-4-yl)-1H-imidazol-2-yl)-4-ethyl-2H-pyrrole-1(5H)-carboxylate

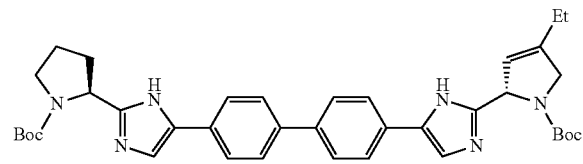 [SMILES: CCC1=C[C@@H](c2ncc(-c3ccc(-c4ccc(-c5cnc([C@@H]6CCCN6C(=O)OC(C)(C)C)[nH]5)cc4)cc3)[nH]2)N(C(=O)OC(C)(C)C)C1]

To a solution of (S)-2-(2-(4'-(2-((S)-1-(tert-butoxycarbonyl)pyrrolidine-2-carbonyloxy)acetyl)biphenyl-4-yl)-2-oxoethyl) 1-tert-butyl 4-ethyl-2H-pyrrole-1,2(5H)-dicarboxylate (intermediate 23) (0.30 g, 0.434 mmol) in dioxane (3 mL) and DMF (3 mL) was added ammonium acetate (0.50 g, 6.51 mmol). The mixture was heated to 110° C. under nitrogen for 16 hours. The mixture was diluted with ethyl acetate (15 mL), washed with water, brine, dried over Na2SO4, concentrated and to give (S)-tert-butyl 2-(5-(4'-(2-((S)-1-(tert-butoxycarbonyl)pyrrolidin-2-yl)-1H-imidazol-5-yl)biphenyl-4-yl)-1H-imidazol-2-yl)-4-ethyl-2H-pyrrole-1(5H)-carboxylate (intermediate 26) (112 mg, yield: 40%) as a yellow solid. ES LC-MS m/z=651 (M+H)+.

Intermediate 27: (S)-tert-butyl 2-(5-(4'-(2-((S)-1-(tert-butoxycarbonyl)pyrrolidin-2-yl)-1H-imidazol-5-yl)biphenyl-4-yl)-1H-imidazol-2-yl)-4-cyclopropyl-2H-pyrrole-1(5H)-carboxylate

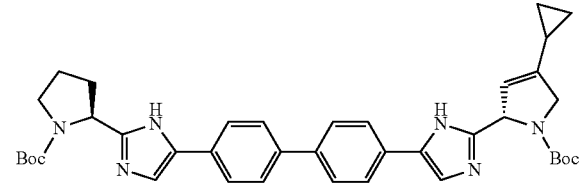 [SMILES: CC(C)(C)OC(=O)N1CC(C2CC2)=C[C@H]1c1ncc(-c2ccc(-c3ccc(-c4cnc([C@@H]5CCCN5C(=O)OC(C)(C)C)[nH]4)cc3)cc2)[nH]1]

To a solution of (S)-2-(2-(4'-(2-((S)-1-(tert-butoxycarbonyl)pyrrolidine-2-carbonyloxy)acetyl)biphenyl-4-yl)-2-oxoethyl) 1-tert-butyl 4-cyclopropyl-2H-pyrrole-1,2(5H)-dicarboxylate (intermediate 24) (1.69 g, 2.4 mmol) in dioxane (15 mL) and DMF (15 mL) was added ammonium acetate (1.85 g, 24 mmol). The mixture was heated to 110° C. under an atmosphere of nitrogen for 16 hours. The mixture was diluted with ethyl acetate (40 mL), washed with water, brine, dried over Na2SO4, concentrated and purified to give (S)-tert-butyl 2-(5-(4'-(2-((S)-1-(tert-butoxycarbonyl)pyrrolidin-2-yl)-1H-imidazol-5-yl)biphenyl-4-yl)-1H-imidazol-2-yl)-4-cyclopropyl-2H-pyrrole-1(5H)-carboxylate (intermediate 27) (0.33 g, yield: 22%) as a yellow solid. ES LC-MS m/z=663 (M+H)+.

Intermediate 32: (S)-tert-butyl 2-(5-(4'-(2-((S)-1-(tert-butoxycarbonyl)pyrrolidin-2-yl)-1H-imidazol-5-yl)biphenyl-4-yl)-1H-imidazol-2-yl)-4-ethylidenepyrrolidine-1-carboxylate

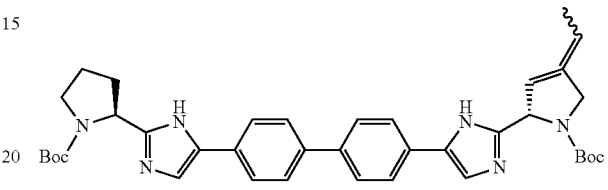

To a solution of (S)-2-(2-(4'-(2-((S)-1-(tert-butoxycarbonyl)pyrrolidine-2-carbonyloxy)acetyl)biphenyl-4-yl)-2-oxoethyl) 1-tert-butyl 4-ethylidenepyrrolidine-1,2-dicarboxylate (intermediate 31) (0.565 g, 0.818 mmol) in dioxane (6 mL) and DMF (6 mL) was added ammonium acetate (0.946 g, 12.3 mmol). The mixture was heated to 110° C. under nitrogen for 16 hours, then diluted with ethyl acetate (40 mL), washed with water, brine, dried over Na2SO4, concentrated and purified to yield (S)-tert-butyl 2-(5-(4'-(2-((S)-1-(tert-butoxycarbonyl)pyrrolidin-2-yl)-1H-imidazol-5-yl)biphenyl-4-yl)-1H-imidazol-2-yl)-4-ethylidenepyrrolidine-1-carboxylate (intermediate 32) (182 mg, yield: 34%) as a yellow solid. ES LC-MS m/z=651 (M+H)+.

Intermediate 28: 2-((S)-4-methyl-2,5-dihydro-1H-pyrrol-2-yl)-5-(4'-(2-((S)-pyrrolidin-2-yl)-1H-imidazol-5-yl)biphenyl-4-yl)-1H-imidazole

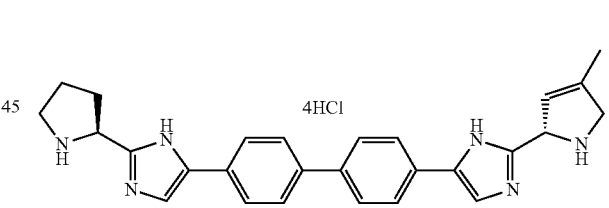

To a solution of (S)-tert-butyl 2-(5-(4'-(2-((S)-1-(tert-butoxycarbonyl)pyrrolidin-2-yl)-1H-imidazol-5-yl)biphenyl-4-yl)-1H-imidazol-2-yl)-4-methyl-2H-pyrrole-1(5H)-carboxylate (intermediate 25) (0.6 g, 0.94 mmol) in dioxane (6 mL) was added a solution of 4N HCl in dioxane (4.7 mL) at 5° C. The mixture was stirred at room temperature for 5 hours. The resulting solid was filtered and washed with petroleum ether/ethyl acetate (1:1, v/v) to give 2-((S)-4-methyl-2,5-dihydro-1H-pyrrol-2-yl)-5-(4'-(2-((S)-pyrrolidin-2-yl)-1H-imidazol-5-yl)biphenyl-4-yl)-1H-imidazole (Intermediate 28) (0.5 g, yield: 93%) as a yellow solid. $^{1}$H NMR (300 MHz, CD3OD) δ ppm 8.13-8.14 (m, 2H), 7.91-8.02 (m, 8H), 6.08 (s, 1H), 5.80 (s, 1H), 5.22-5.28 (m, 1H), 4.20-4.30 (m, 2H), 3.62-3.68 (m, 2H), 2.62-2.76 (m, 2H), 2.43-2.44 (m, 1H), 2.29-2.32 (m, 1H), 2.08 (s, 3H). ES LC-MS m/z=437 (M+H)+.

Intermediate 29: 2-((S)-4-ethyl-2,5-dihydro-1H-pyrrol-2-yl)-5-(4'-(2-((S)-pyrrolidin-2-yl)-1H-imidazol-5-yl)biphenyl-4-yl)-1H-imidazole

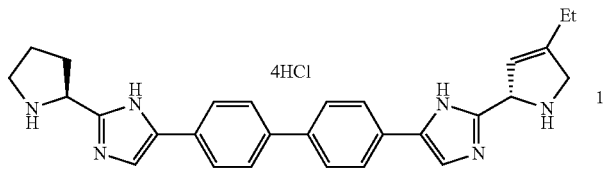

To a solution of (S)-tert-butyl 2-(5-(4'-(2-((S)-1-(tert-butoxycarbonyl)pyrrolidin-2-yl)-1H-imidazol-5-yl)biphenyl-4-yl)-1H-imidazol-2-yl)-4-ethyl-2H-pyrrole-1(5H)-carboxylate (intermediate 26) (0.171 g, 0.248 mmol) in dioxane (4 mL) was added a solution of 5.5N HCl in dioxane (2.5 mL) at 0° C. The mixture was stirred at room temperature for 20 hours. The resulting mixture was concentrated to give 2-((S)-4-methyl-2,5-dihydro-1H-pyrrol-2-yl)-5-(4'-(2-((S)-pyrrolidin-2-yl)-1H-imidazol-5-yl)biphenyl-4-yl)-1H-imidazole (Intermediate 29) (0.121 g, yield: 83%) as a brown solid. ES LC-MS m/z=451 (M+H)+.

Intermediate 30: 2-((S)-4-cyclopropyl-2,5-dihydro-1H-pyrrol-2-yl)-5-(4'-(2-((S)-pyrrolidin-2-yl)-1H-imidazol-5-yl)biphenyl-4-yl)-1H-imidazole

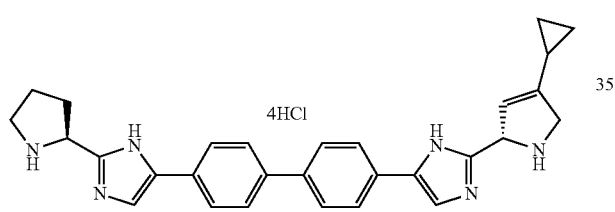

To a solution of (S)-tert-butyl 2-(5-(4'-(2-((S)-1-(tert-butoxycarbonyl)pyrrolidin-2-yl)- 1H-imidazol-5-yl)biphenyl-4-yl)-1H-imidazol-2-yl)-4-cyclopropyl-2H-pyrrole-1(5H)-carboxylate (intermediate 27) (0.161 g, 0.243 mmol) in dioxane (3 mL) was added a solution of 5N HCl in dioxane (2 mL) at 10° C. The mixture was stirred at room temperature for 16 hours. The resulting mixture was concentrated to give 2-((S)-4-cyclopropyl-2,5-dihydro-1H-pyrrol-2-yl)-5-(4'-(2-((S)-pyrrolidin-2-yl)-1H-imidazol-5-yl)biphenyl-4-yl)-1H-imidazole (Intermediate 30) (0.134 g, yield: 91%) as a light brown solid. ES LC-MS m/z=463 (M+H)+.

Intermediate 33: 2-((S)-4-ethylidenepyrrolidin-2-yl)-5-(4'-(2-((S)-pyrrolidin-2-yl)-1H-imidazol-5-yl)biphenyl-4-yl)-1H-imidazole

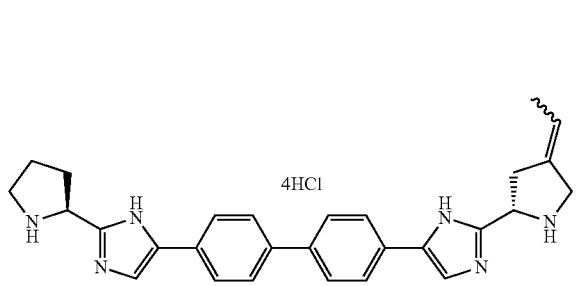

To a solution of (S)-tert-butyl 2-(5-(4'-(2-((S)-1-(tert-butoxycarbonyl)pyrrolidin-2-yl)-1H-imidazol-5-yl)biphenyl-4-yl)-1H-imidazol-2-yl)-4-ethylidenepyrrolidine-1-carboxylate (intermediate 32) (0.180 g, 0.276 mmol) in dioxane (0.5 mL) was added a solution of 2N HCl in dioxane (3 mL) at 10° C. The mixture was stirred at room temperature for 16 hours. The resulting mixture was concentrated to give 2-((S)-4-ethylidenepyrrolidin-2-yl)-5-(4'-(2-((S)-pyrrolidin-2-yl)-1H-imidazol-5-yl)biphenyl-4-yl)-1H-imidazole (Intermediate 33) (0.118 g, yield: 72%) as a yellow solid. ES LC-MS m/z=451 (M+H)+.

Example 9

(1-{(S)-2-[5-(4'-{2-[(S)-1-((R)-2-Methoxycarbonylamino-3-methyl-butyryl)-4-methyl-2,5-dihydro-1H-pyrrol-2-yl]-3H-imidazol-4-yl}-biphenyl-4-yl)-1H-imidazol-2-yl]-pyrrolidine-1-carbonyl}-2-methyl-propyl)-carbamic acid methyl ester

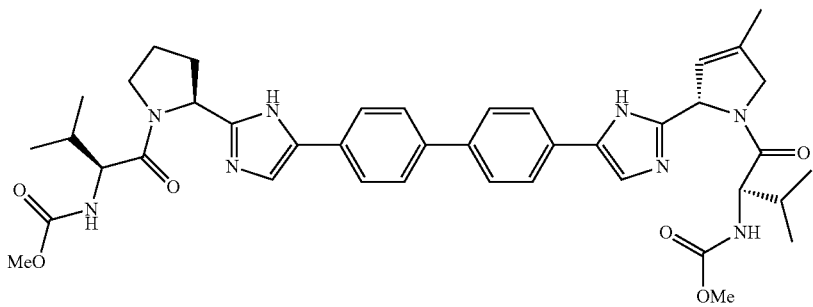 [SMILES: COC(=O)N[C@H](C(=O)N1CCC[C@H]1c1ncc(-c2ccc(-c3ccc(-c4cnc([C@@H]5C=C(C)CN5C(=O)[C@H](NC(=O)OC)C(C)C)[nH]4)cc3)cc2)[nH]1)C(C)C]

A solution of N-[(methyloxy)carbonyl]-L-valine (49.3 mg, 0.282 mmol), HATU (139 mg, 0.367 mmol), DIPEA (109 mg, 0.846 mmol) and DMF (0.9 mL) was added to 2-((S)-4-methyl-2,5-dihydro-1H-pyrrol-2-yl)-5-(4'-(2-((S)-pyrrolidin-2-yl)-1H-imidazol-5-yl)biphenyl-4-yl)-1H-imidazole (intermediate 28) (82 mg, 0.141 mmol). After 10 minutes at room temperature, the mixture was added water (20 mL) and extracted with ethyl acetate (20 mL×2). Combined organic phase was washed with aqueous saturated NaHCO₃ (10 mL), brine (10 mL), dried over Na₂SO₄, concentrated and purified by flash chromatography (DCM:methanol:Et₃N=15:1:0.05) to give (1-{(S)-2-[5-(4'-{2-[(S)-1-((R)-2-Methoxycarbonylamino-3-methyl-butyryl)-4-methyl-2,5-dihydro-1H-pyrrol-2-yl]-3H-imidazol-4-yl}-biphenyl-4-yl)-1H-imidazol-2-yl]-pyrrolidine-1-carbonyl}-2-methyl-propyl)-carbamic acid methyl ester (Example 9) (28 mg, yield: 27%) as a yellow solid. $^1$H NMR (300 MHz, CD$_3$OD) δ ppm 7.61-7.72 (m, 8H), 7.30-7.32 (m, 2H), 5.85 (d, J=1.8 Hz, 1H), 5.54 (s, 1H), 5.18-5.22 (m, 1H), 4.58-4.73 (m, 2H), 4.26 (d, J=7.5 Hz, 1H), 4.18 (d, J=7.8 Hz, 1H), 3.86-4.07 (m, 2H), 3.67 (s, 6H), 2.02-2.36 (m, 6H), 1.92 (s, 3H), 0.91-1.02 (m, 12H). ES LC-MS m/z=751 (M+H)+.

Example 10

(1-{(S)-2-[5-(4'-{2-[(S)-4-Ethyl-1-((R)-2-methoxy-carbonylamino-3-methyl-butyryl)-2,5-dihydro-1H-pyrrol-2-yl]-3H-imidazol-4-yl}-biphenyl-4-yl)-1H-imidazol-2-yl]-pyrrolidine-1-carbonyl]-2-methyl-propyl)-carbamic acid methyl ester

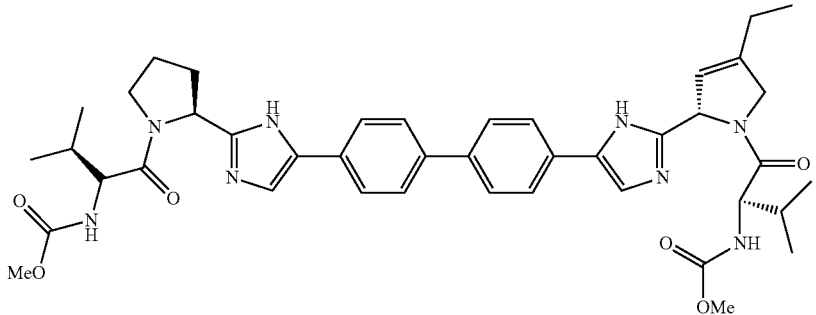

A solution of N-[(methyloxy)carbonyl]-L-valine (88 mg, 0.503 mmol), HATU (248 mg, 0.653 mmol), DIPEA (195 mg, 1.506 mmol) and DMF (1.7 mL) was added to 2-((S)-4-methyl-2,5-dihydro-1H-pyrrol-2-yl)-5-(4'-(2-((S)-pyrrolidin-2-yl)-1H-imidazol-5-yl)biphenyl-4-yl)-1H-imidazole (intermediate 29) (150 mg, 0.251 mmol). The reaction solution was stirred at room temperature for 10 minutes and diluted with water (20 mL), extracted with ethyl acetate (20 mL×2). The organic layers were combined and washed with saturated NaHCO$_3$ aqueous (10 mL), brine (10 mL), dried over Na$_2$SO$_4$, concentrated and purified by flash chromatography (DCM:methanol:Et$_3$N=15:1:0.05) to give (1-{(S)-2-[5-(4'-{2-[(S)-4-Ethyl-1-((R)-2-methoxycarbonylamino-3-methyl-butyryl)-2,5-dihydro-1H-pyrrol-2-yl]-3H-imidazol-4-yl}-biphenyl-4-yl)-1H-imidazol-2-yl]-pyrrolidine-1-carbonyl}-2-methyl-propyl)-carbamic acid methyl ester (Example 10) (49 mg, yield: 26%) as a yellow solid. $^1$H NMR (300 MHz, CD$_3$OD) δ ppm 7.59-7.76 (m, 8H), 7.28-7.33 (m, 2H), 5.87 (s, 1H), 5.53 (s, 1H), 5.18-5.22 (m, 1H), 4.64-4.70 (m, 2H), 4.26 (d, J=7.5 Hz, 1H)), 4.20 (d, J=7.8 Hz, 1H), 3.86-4.07 (m, 2H), 3.67 (s, 6H), 2.00-2.34 (m, 8H), 1.15-1.22 (m, 3H), 0.90-1.03 (m, 12H). ES LC-MS m/z=765 (M+H)+.

Example 11 methyl[(1S)-1-({(2S)-2-[4-(4'-{2-[(2S)-4-cyclopropyl-1-((2S)-3-methyl-2-{[(methyloxy)carbonyl]amino}butanoyl)-2,5-dihydro-1H-pyrrol-2-yl]-1H-imidazol-4-yl}-4-biphenylyl)-1H-imidazol-2-yl]-1-pyrrolidinyl}carbonyl)-2-methylpropyl]carbamate

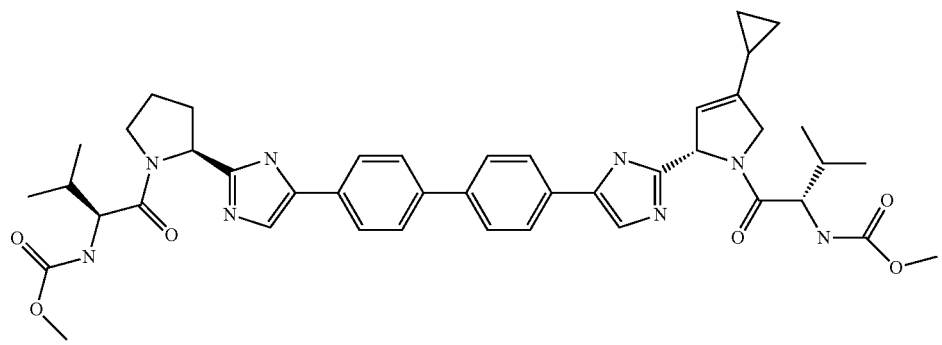 [SMILES: COC(=O)N[C@H](C(=O)N1CC(C2CC2)=C[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C]

A solution of N-[(methyloxy)carbonyl]-L-valine (86 mg, 0.493 mmol), HATU (216 mg, 0.568 mmol), DIEA (192 mg, 1.482 mmol) and DMF (1.7 mL) was added to 2-((S)-4-cyclopropyl-2,5-dihydro-1H-pyrrol-2-yl)-5-(4'-(2-((S)-pyrrolidin-2-yl)-1H-imidazol-5-yl)biphenyl-4-yl)-1H-imidazole (intermediate 30) (150 mg, 0.247 mmol). The solution was stirred at room temperature for 10 minutes and diluted with water (20 mL), extracted with ethyl acetate (20 mL×2). The organic layers were combined and washed with saturated NaHCO$_3$ aqueous (10 mL), brine (10 mL), dried over Na$_2$SO$_4$, concentrated and purified by pre-TLC (DCM:methanol:Et$_3$N=15:1:0.05) to give (1-{(S)-2-[5-(4'-{2-[(S)-4-Cyclopropyl-1-((R)-2-methoxycarbonylamino-3-methyl-butyryl)-2,5-dihydro-1H-pyrrol-2-yl]-3H-imidazol-4-yl}-biphenyl-4-yl)-1H-imidazol-2-yl]-pyrrolidine-1-carbonyl}-2-methyl-propyl)-carbamic acid methyl ester (Example 11) (29 mg, yield: 15%) as a yellow solid. $^1$H NMR (300 MHz, CD$_3$OD) δ ppm 7.60-7.77 (m, 8H), 7.30-7.33 (m, 2H), 5.84 (s, 1H), 5.50 (s, 1H), 5.18-5.22 (m, 1H), 4.61-4.65 (m, 2H), 4.26 (d, J=7.5 Hz, 1H), 4.17 (d, J=8.1 Hz, 1H), 3.88-4.00 (m, 2H), 3.66 (s, 6H), 1.99-2.35 (m, 6H), 1.58-1.62 (m, 1H), 0.65-1.07 (m, 16H). ES LC-MS m/z=777 (M+H)+.

Example 12

(1-{(S)-2-[5-(4'-{2-[(S)-4-Ethylidene-1-(2-methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-2-methyl-propyl)-carbamic acid methyl ester

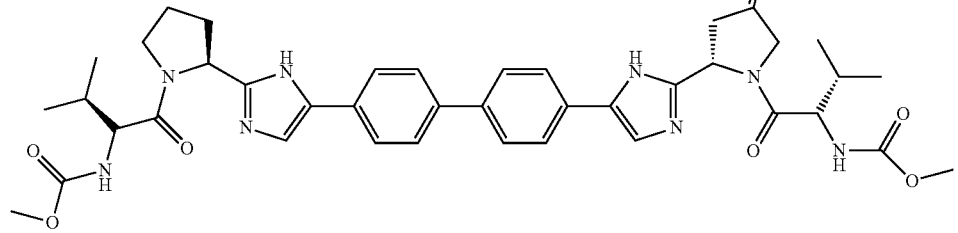

A solution of N-[(methyloxy)carbonyl]-L-valine (27 mg, 0.154 mmol), HATU (76 mg, 0.200 mmol), DIPEA (60 mg, 0.462 mmol) and DMF (0.50 mL) was added to 2-((S)-4-ethylidenepyrrolidin-2-yl)-5-(4'-(2-((S)-pyrrolidin-2-yl)-1H-imidazol-5-yl)biphenyl-4-yl)-1H-imidazole (intermediate 33) (46 mg, 0.077 mmol). The solution was stirred at room temperature for 10 minutes and diluted with water (20 mL), extracted with ethyl acetate (20 mL×2). The organic layers were combined and washed with saturated NaHCO$_3$ aqueous (10 mL), brine (10 mL), dried over Na$_2$SO$_4$, concentrated and purified by pre-TLC (DCM:methanol:Et$_3$N=15:1:0.1) to give (1-{(S)-2-[5-(4'-{2-[(S)-4-Ethylidene-1-(2-methoxycarbonylamino-3-methyl-butyryl)-pyrrolidin-2-yl]-3H-imidazol-4-yl}-biphenyl-4-yl)-1H-imidazol-2-yl]-pyrrolidine-1-carbonyl}-2-methyl-propyl)-carbamic acid methyl ester (Example 12) (11 mg, yield: 20%) as a yellow solid. $^1$H NMR (300 MHz, CD$_3$OD) δ ppm 7.64-7.82 (m, 8H), 7.32-7.37 (m, 2H), 5.53-5.55 (m, 1H), 5.36-5.44 (m, 1H), 5.18-5.22 (m, 1H), 4.53-4.71 (m, 2H), 4.26 (d, J=7.8 Hz, 2H), 3.88-4.13 (m, 2H), 3.74 (s, 6H), 3.02-3.05 (m, 1H), 2.79-2.83 (m, 1H), 2.06-2.39 (m, 6H), 1.67-1.76 (m, 3H), 0.87-1.05 (m, 12H). ES LC-MS m/z=765 (M+H)+.

Protocol for Testing and Data Analysis of Compounds in the HCV Replicon Assay

Compounds were assayed for activity against HCV using the genotype 1a and 1b subgenomic replicon model systems. Stable cell lines bearing the genotype 1a and 1b replicons were used for screening of compounds. Both replicons are bicistronic and contain the firefly luciferase gene. The ET cell line is stably transfected with RNA transcripts harboring a I$_{389}$luc-ubi-neo/NS3-3'/ET replicon with firefly luciferase-ubiquitin-neomycin phosphotransferase fusion protein and EMCV-IRES driven NS3-5B polyprotein containing the cell culture adaptive mutations (E1202G; T1280I; K1846T) (Krieger at al, 2001 and unpublished). The genotype 1a replicon is a stable cell line licensed from Apath LLC, modified to contain the firefly luciferase gene. The cells were grown in DMEM, supplemented with 10% fetal calf serum, 2 mM Glutamine, Penicillin (100 IU/mL)/Streptomycin (100 μg/mL), 1× nonessential amino acids, and 250-500 μg/mL G418 ("Geneticin"). They were all available through Life Technologies (Bethesda, Md.). The cells were plated at 0.5× 10$^4$ cells/well in 384 well plates containing compounds. The final concentration of compounds ranged between 0.03 pM to 50 μm and the final DMSO concentration of 0.5-1%.

Luciferase activity was measured 48 hours later by adding a Steady glo (Promega, Madison, Wis.). Percent inhibition of replication data was plotted relative to no compound control. Under the same condition, cytotoxicity of the compounds was determined using cell titer glo (Promega, Madison, Wis.). EC50s were determined from a 10 point dose response curve using 3-4-fold serial dilution for each compound, which spans a concentration range >1000 fold. BioAssay determines the level of inhibition for each compound by normalizing cross-talk corrected plate values against the negative (low or background, cells with no compound present) and positive (high DMSO, no cells) controls to determine Percent Inhibition:

$$100 * \left(1 - \frac{\text{(Cross-talk corrected value} - \text{Compound Positive Control Mean)}}{\text{DMSO Negative Control Mean} - \text{Compound Positive Control Mean}}\right)$$

These normalized values are exported to EC$_{50}$ where they are plotted against the molar compound concentrations using the standard four parameter logistic equation:

$$y = A + \frac{B - A}{1 + \left[\frac{10^x}{10^c}\right]^D}$$

Where:

A=minimum y D=slope factor

B=maximum y x=$\log_{10}$ compound concentration [M]

C=$\log_{10} EC_{50}$ pEC$_{50}$=−C

As shown below, the tested compounds tested were found to inhibit the activity of the replicon with pEC$_{50}$>5.

|  | 1A pEC50 | 1B pEC50 |
| --- | --- | --- |
| example 1 | 8.8 | 11.46 |
| example 9 | 10.8 | 11.11 |
| example 10 | 10.5 | 11.22 |
| example 11 | 10.9 | 11.33 |
| example 12 | 10.8 | 11.36 |

FORMULATION EXAMPLES

The following are representative pharmaceutical formulations containing a compound of the present invention.

Example 1

Tablet Formulation

The following ingredients are mixed intimately and pressed into single scored tablets.

| Ingredient | Quantity per tablet, mg |
| --- | --- |
| Compound | 400 |
| Cornstarch | 50 |
| Croscarmellose sodium | 25 |
| Lactose | 120 |
| Magnesium stearate | 5 |

Example 2

Capsule Formulation

The following ingredients are mixed intimately and loaded into a hard-shell gelatin capsule.

| Ingredient | Quantity per tablet, mg |
| --- | --- |
| Compound | 200 |
| Lactose, spray-dried | 148 |
| Magnesium stearate | 2 |

Example 3

Suspension Formulation

The following ingredients are mixed to form a suspension for oral administration.

| Ingredient | Amount |
| --- | --- |
| Compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.0 g |
| Sorbitol (70% solution) | 13.0 g |
| Veegum K (Vanderbilt Co.) | 1.0 g |
| flavoring | 0.035 mL |
| colorings | 0.5 mg |
| distilled water | q.s. to 100 mL |

Example 4

Injectable Formulation

The following ingredients are mixed to form an injectable formulation.

| Ingredient | Quantity per tablet, mg |
| --- | --- |
| Compound | 0.2 mg-20 mg |
| sodium acetate buffer solution, 0.4M | 2.0 mL |
| HCl (IN) or NaOH (IN) | q.s. to suitable pH |
| water (distilled, sterile) | q.s. to 20 mL |

Example 5

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Quantity per tablet, mg |
| --- | --- |
| Compound | 500 mg |
| Witepsol ® H-15 | balance |

What is claimed is:

1. A compound selected from the group consisting of

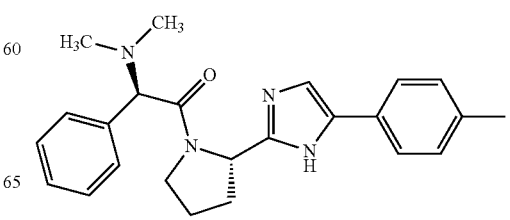

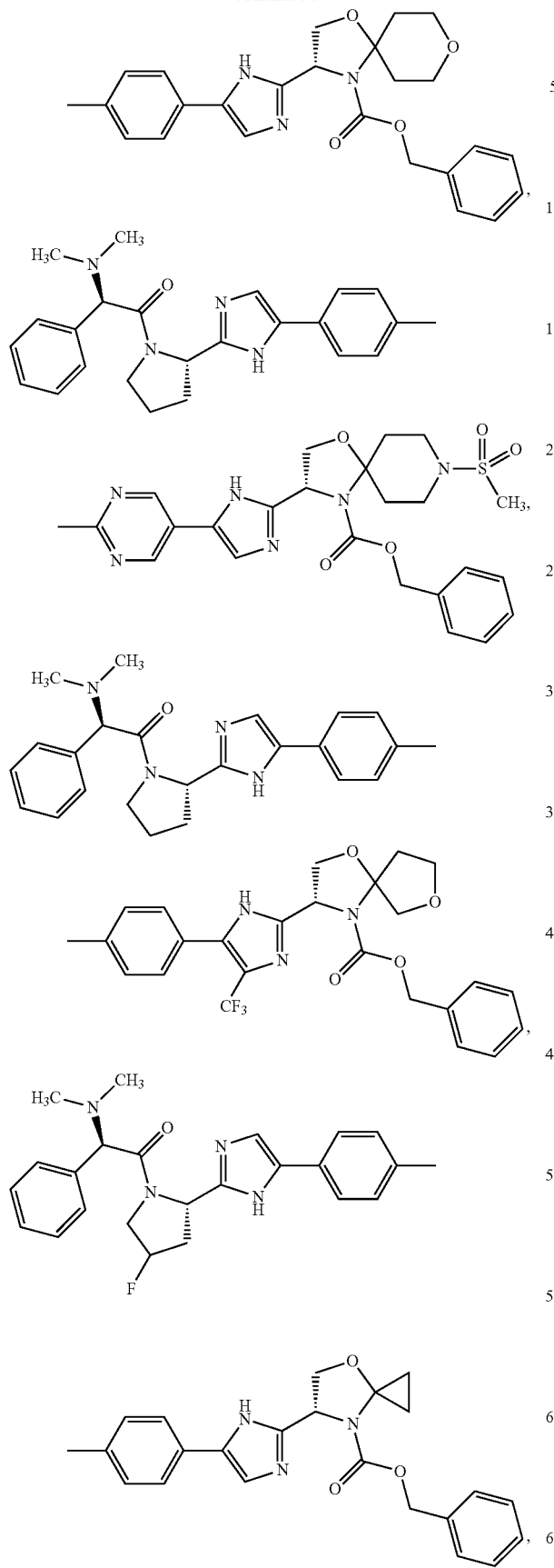
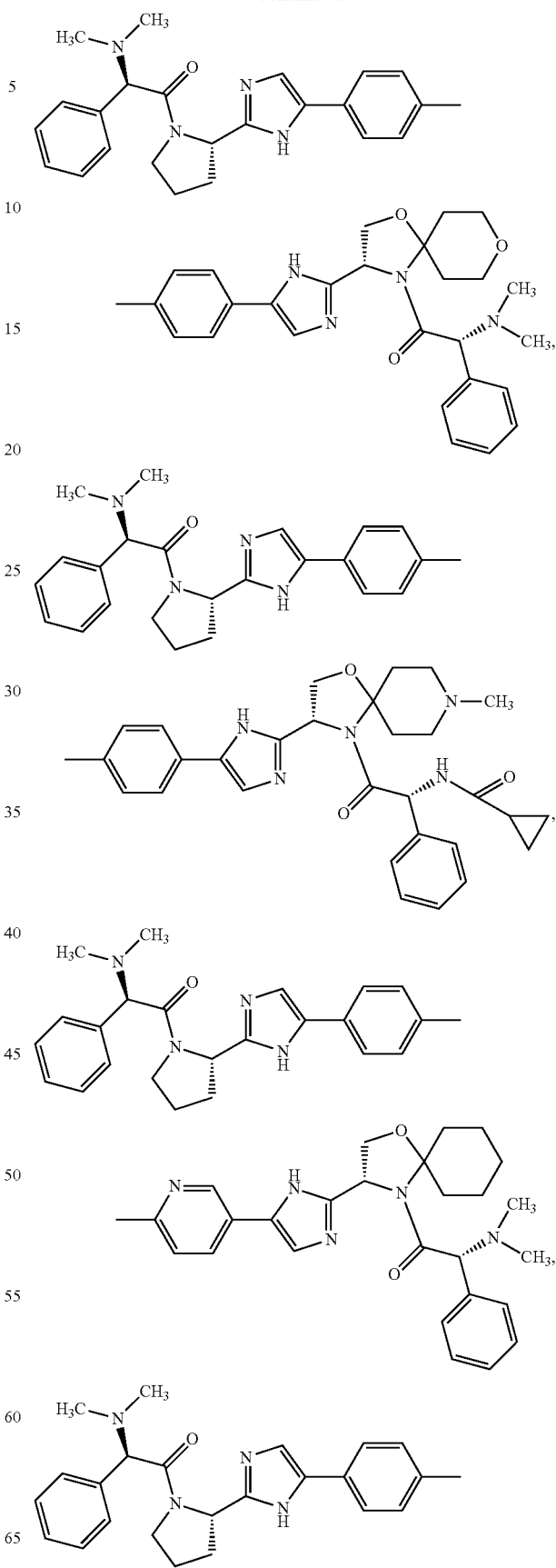

77
-continued
78
-continued
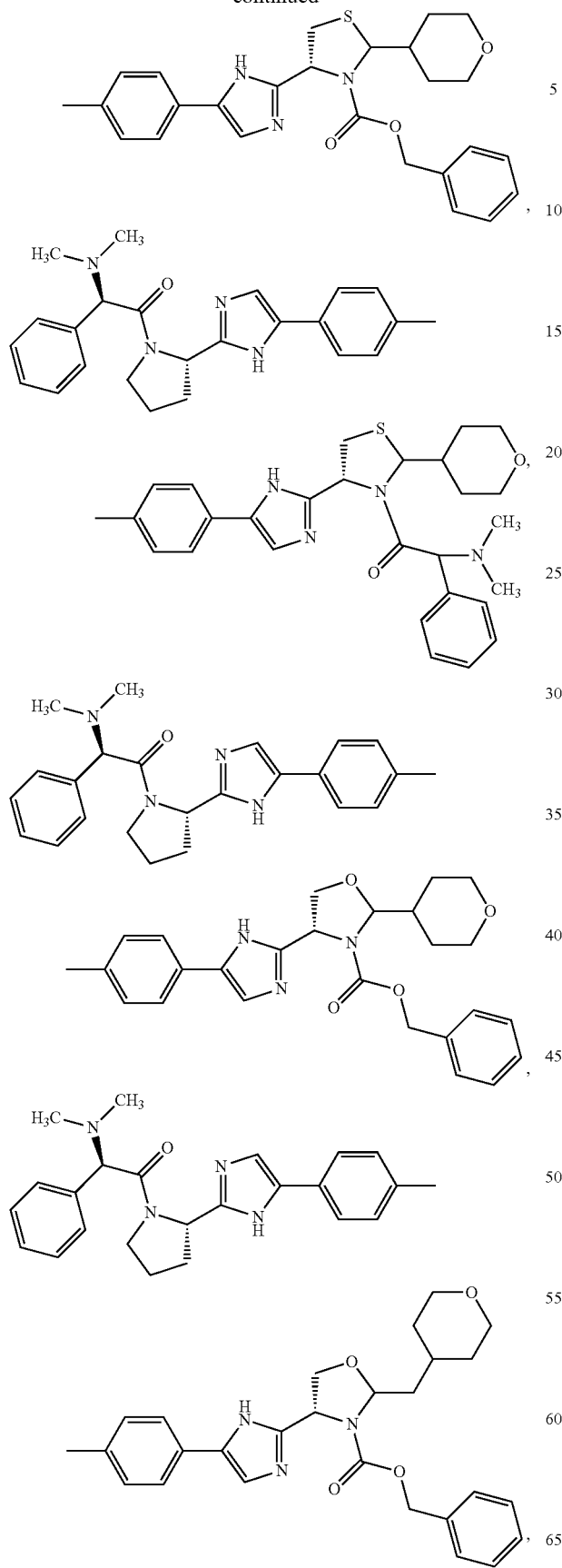
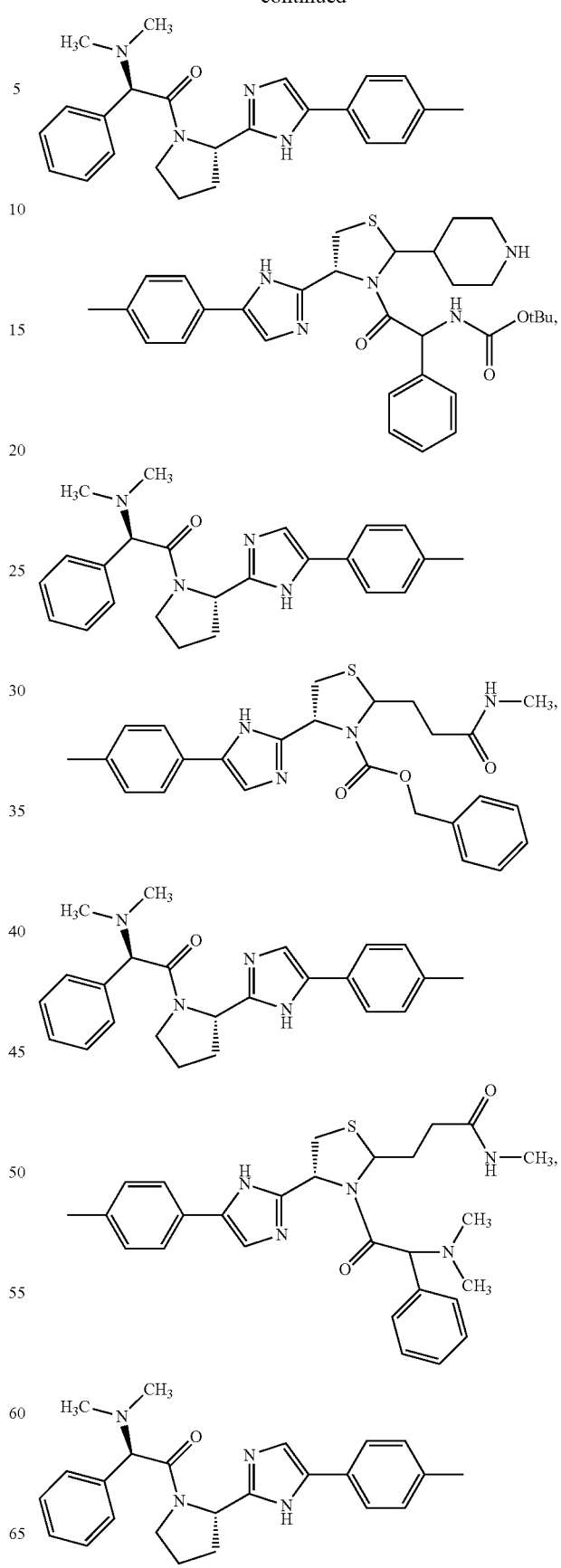

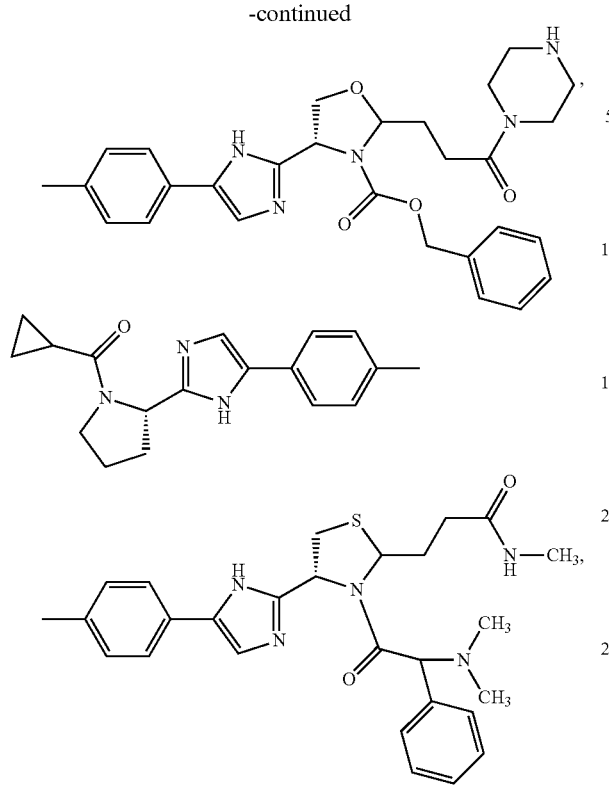
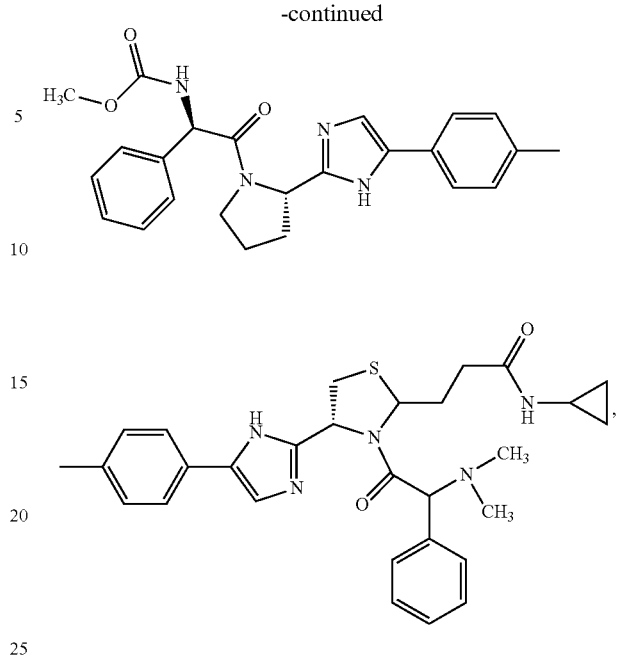
and pharmaceutically acceptable salts thereof.
2. A composition comprising a therapeutically effective amount of a compound of claim 1 and a pharmaceutically acceptable carrier.
3. A compound selected from the group consisting of
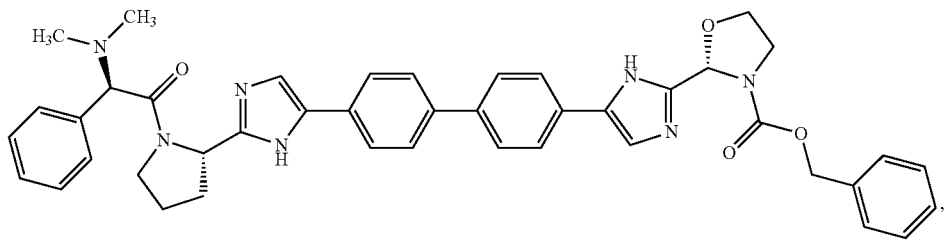
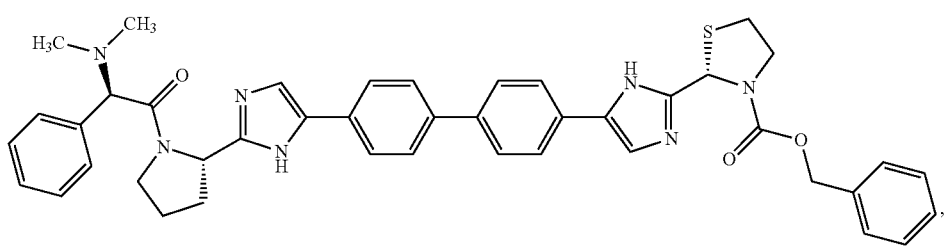
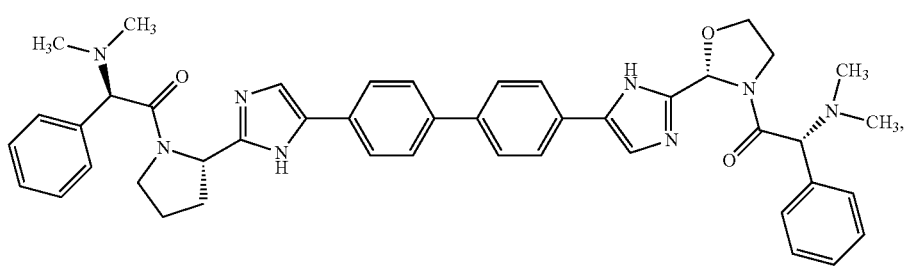

-continued
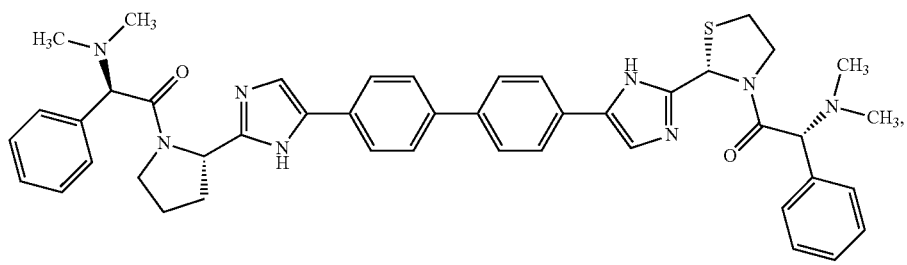
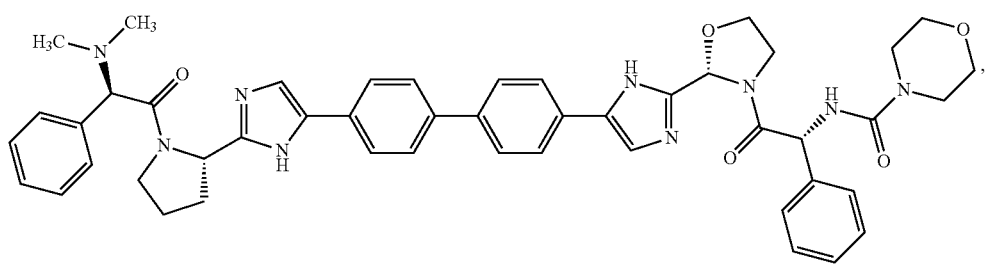
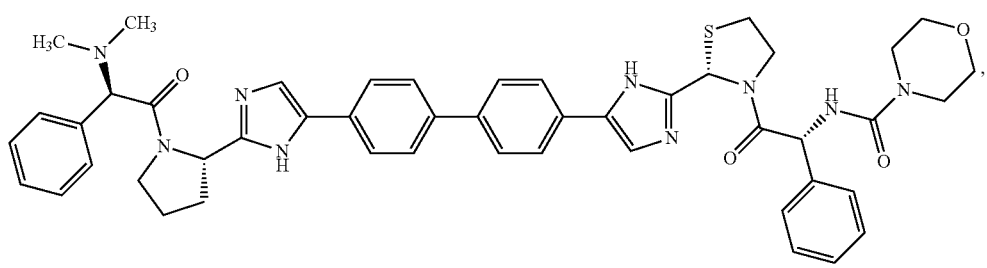
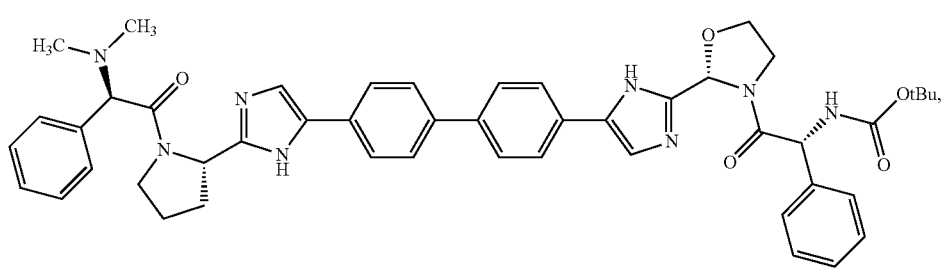
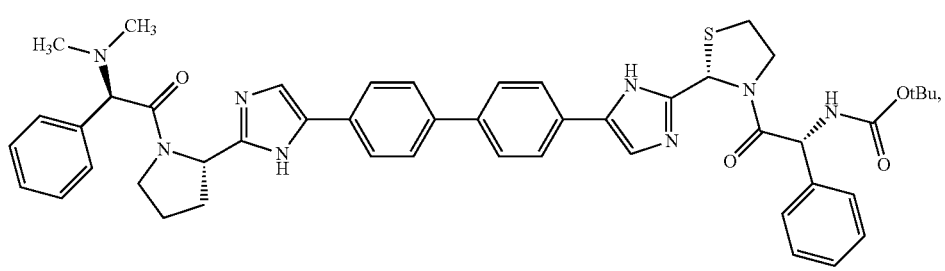
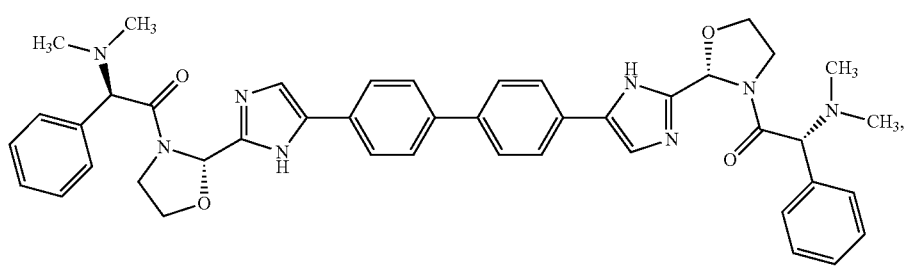

-continued
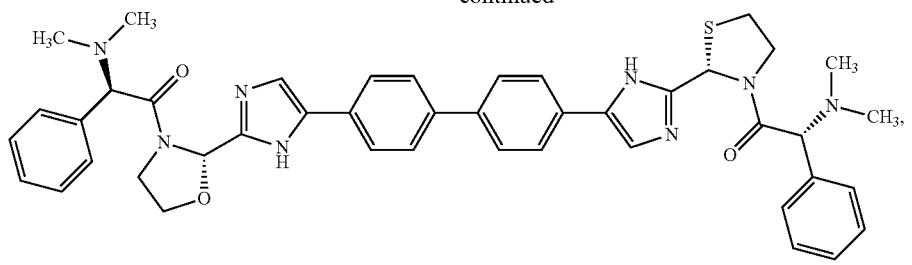
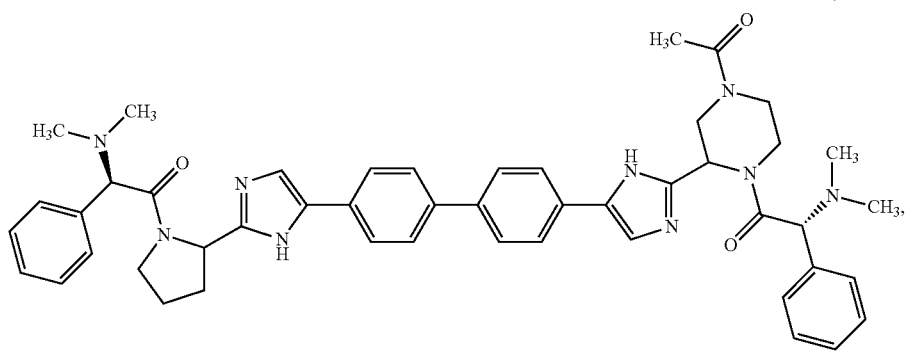
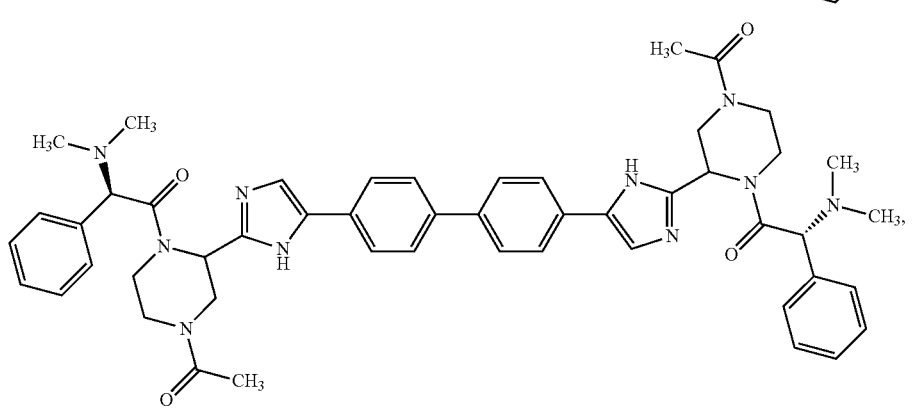
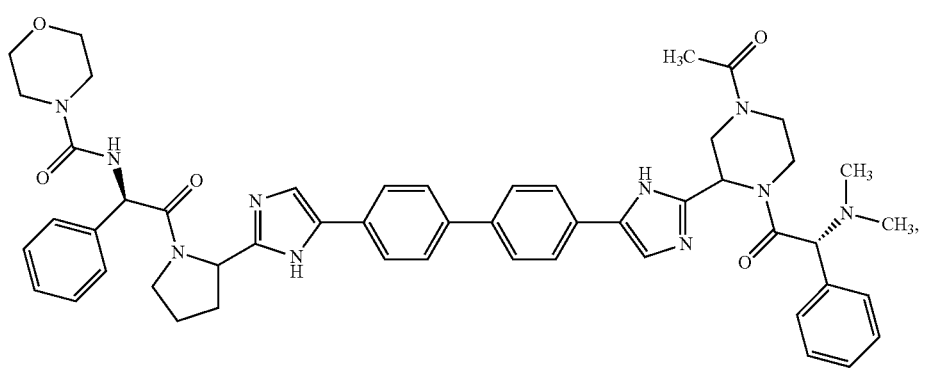
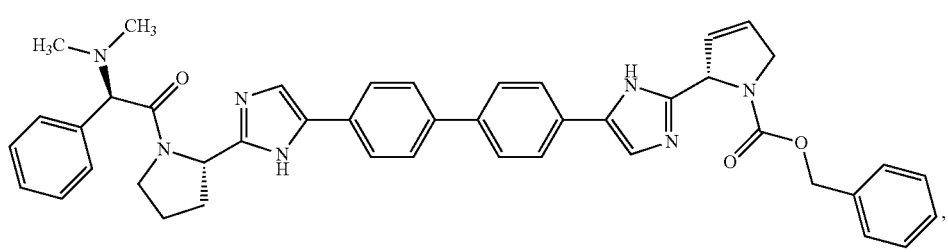

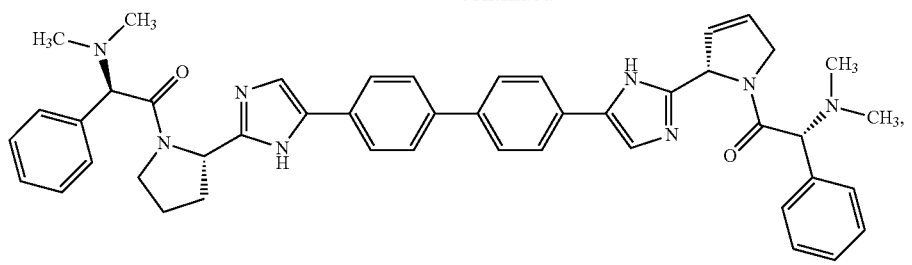
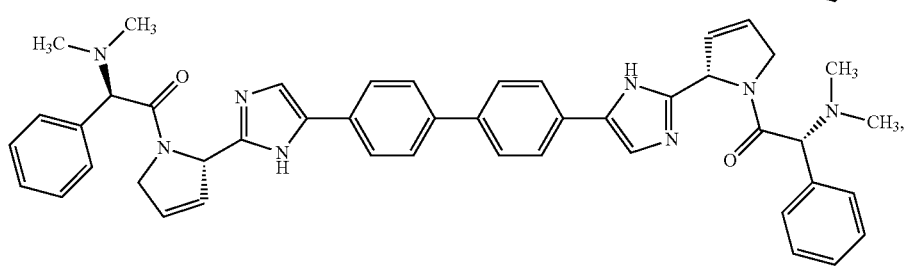
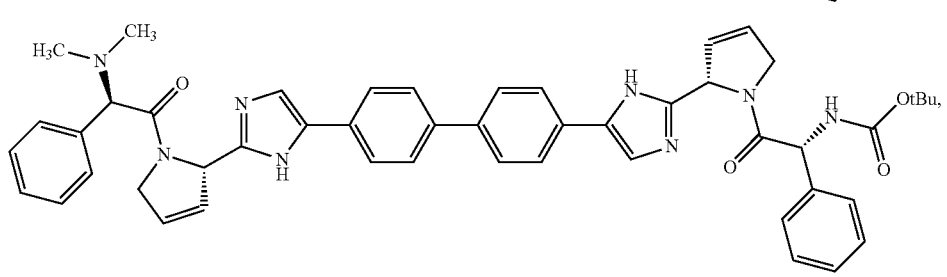
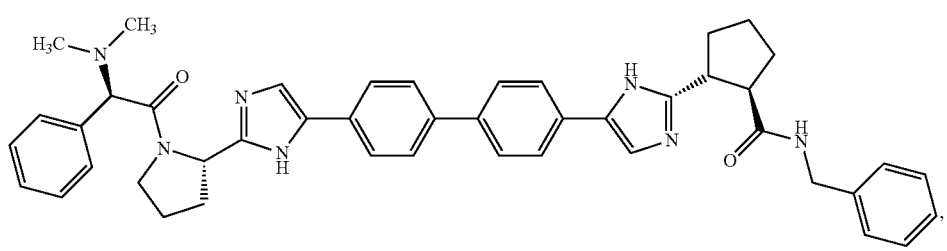
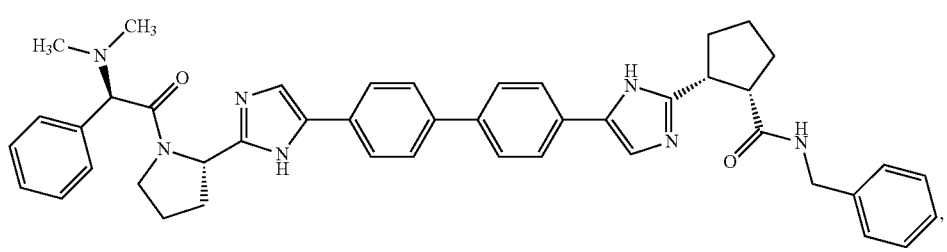
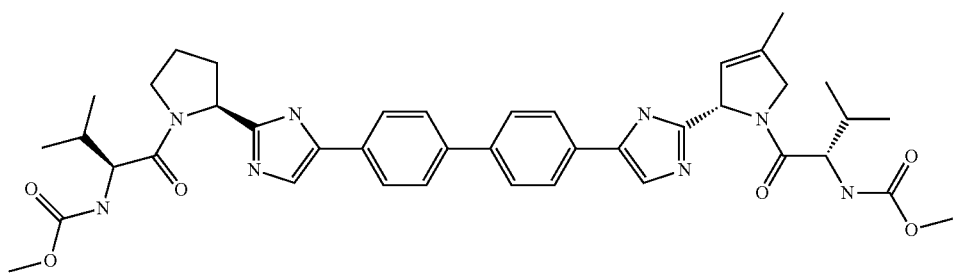

-continued
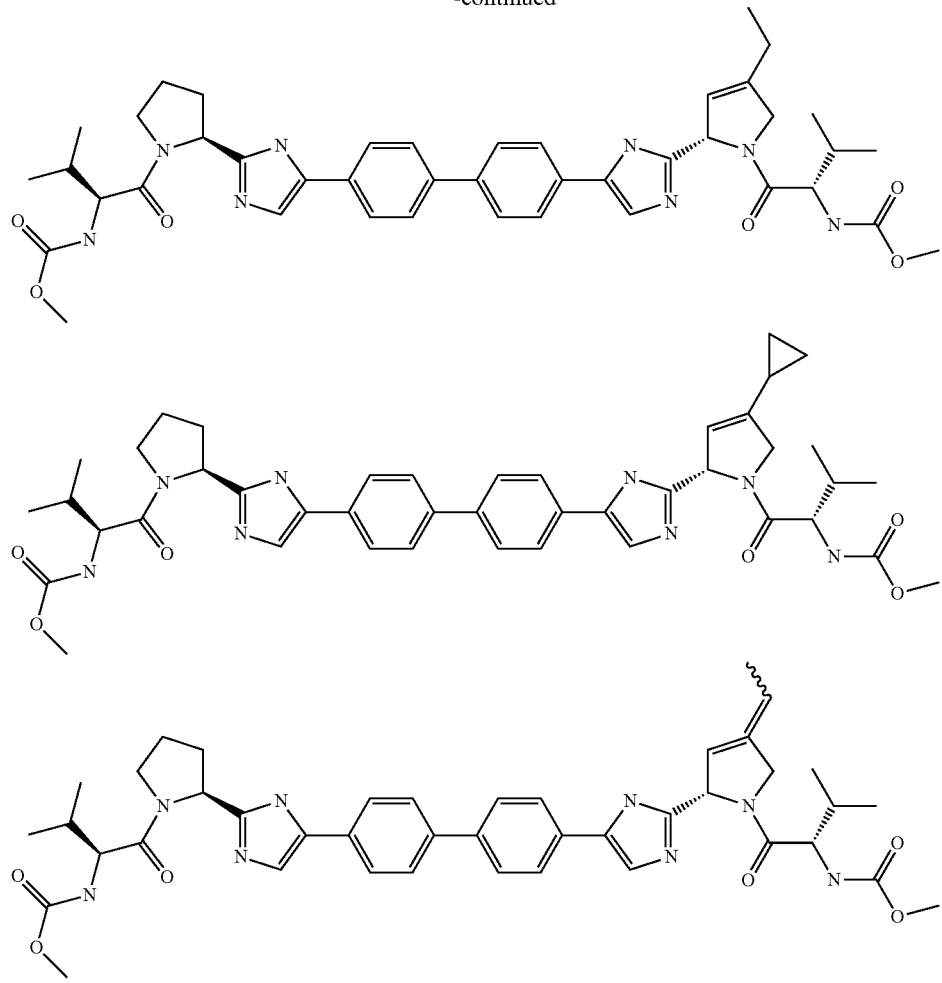
and pharmaceutically acceptable salts thereof.
4. A composition comprising a therapeutically effective amount of a compound of claim 3 and a pharmaceutically acceptable carrier.
* * * * *